(12) United States Patent
Zanuzoski

(10) Patent No.: US 9,934,366 B1
(45) Date of Patent: Apr. 3, 2018

(54) MEDICINE MANAGEMENT AND IDENTIFICATION SYSTEM AND KIT

(71) Applicant: Francie M. Zanuzoski, Lakewood, WA (US)

(72) Inventor: Francie M. Zanuzoski, Lakewood, WA (US)

( * ) Notice: Subject to any disclaimer, the term of this patent is extended or adjusted under 35 U.S.C. 154(b) by 20 days.

(21) Appl. No.: 15/344,492

(22) Filed: Nov. 4, 2016

(51) Int. Cl.
| G06F 19/00 | (2018.01) |
| B42D 15/00 | (2006.01) |
| G09F 3/02 | (2006.01) |
| G06Q 50/24 | (2012.01) |
| G06Q 50/22 | (2018.01) |

(52) U.S. Cl.
CPC ........ *G06F 19/3462* (2013.01); *G06F 19/322* (2013.01); *B42D 15/00* (2013.01); *G06F 19/3456* (2013.01); *G06Q 50/22* (2013.01); *G06Q 50/24* (2013.01); *G09F 2003/0272* (2013.01)

(58) Field of Classification Search
CPC .. G06F 19/3462; G06F 19/322; G06F 19/324; G06F 19/326; G06Q 50/22; G06Q 50/24
See application file for complete search history.

(56) References Cited

U.S. PATENT DOCUMENTS

| 3,456,373 | A | 7/1969 | Epton |
| 3,716,935 | A | 2/1973 | Friederichs |
| 4,242,823 | A | 1/1981 | Bruno |
| 5,102,169 | A | 4/1992 | Mayfield |
| 5,261,702 | A | 11/1993 | Mayfield |
| 5,568,890 | A | 10/1996 | Magee et al. |
| 5,806,670 | A | 9/1998 | Harlan |
| 5,996,822 | A | 12/1999 | Hopkins |
| 6,169,707 | B1 | 1/2001 | Newland |
| 6,361,130 | B1 | 3/2002 | Kardy |
| 7,240,793 | B2 * | 7/2007 | McBain ............ A61J 1/03 206/232 |
| 7,320,483 | B2 | 1/2008 | Eippert |

(Continued)

OTHER PUBLICATIONS

Cardinal Bag Supplies, Product: Prescription Medication Bag Standard Lock Travel Case, Nov. 4, 2016, 1 page, Amazon.com at https://www.amazon.com/Prescription-Medication-Bag-Standard-Travel/dp/B00JV598Y4, US.

(Continued)

*Primary Examiner* — Victoria P Shumate
*Assistant Examiner* — Jonathan Durant
(74) *Attorney, Agent, or Firm* — Patentpending, PLLC; Elizabeth Reilly

(57) ABSTRACT

Aspects of the disclosure relate to a medicine management and identification system including a portable rigid ferromagnetic substrate, a periodic daily event color-code sheet, a plurality of medicine exemplar containers, one or more malleable substrates, a medicine management cabinet, a mounting platform, an actual medicine product daily organizer, a mobile communications device, a medicine management notebook, for the management and identification of a plurality of actual medicine products of one or more medical regimens of a specific patient. Another aspect of the disclosure includes a medicine management and identification kit, and a medicine management and identification method.

38 Claims, 39 Drawing Sheets

(56) References Cited

U.S. PATENT DOCUMENTS

| | | |
|---|---|---|
| 7,555,875 B2 | 7/2009 | Kim |
| 7,793,785 B2 | 9/2010 | Keffeler et al. |
| 7,917,375 B2 | 3/2011 | Ohmura et al. |
| 7,926,850 B1 | 4/2011 | Muncy et al. |
| 8,151,980 B2 | 8/2012 | DeMartino |
| 8,336,917 B2 | 12/2012 | Doiron |
| 8,392,220 B2 | 3/2013 | Knowlton et al. |
| 8,517,478 B2 | 8/2013 | Diemel |
| 8,550,248 B1 | 10/2013 | Busen |
| 8,550,578 B2 | 10/2013 | Brink |
| 8,805,572 B2 | 8/2014 | Kim |
| 8,860,560 B2 | 10/2014 | Kim |
| 9,271,898 B2 | 3/2016 | Flynn |
| 9,290,302 B2 | 3/2016 | Horn |
| 2005/0029156 A1 | 2/2005 | Girzaitis |
| 2005/0205439 A1* | 9/2005 | Stafford .............. A61J 7/04 206/232 |
| 2006/0070895 A1* | 4/2006 | Khawaja ............. A61J 7/04 206/223 |
| 2007/0262683 A1 | 11/2007 | Creed |
| 2009/0295260 A1 | 12/2009 | Brink |
| 2010/0133963 A1 | 6/2010 | Brink |
| 2012/0008847 A1 | 1/2012 | Coe |
| 2013/0069510 A1 | 3/2013 | Wexler |
| 2013/0205628 A1* | 8/2013 | Nance .............. G09F 3/00 40/638 |
| 2013/0220850 A1 | 8/2013 | Wingate, III |
| 2013/0264352 A1* | 10/2013 | Hagadorn ............. B42D 15/00 221/1 |
| 2013/0345859 A1* | 12/2013 | Omura .............. A61J 3/00 700/231 |
| 2014/0346939 A1 | 11/2014 | Rickman |
| 2015/0048100 A1* | 2/2015 | Dickie .............. A61J 7/0481 221/1 |
| 2016/0042150 A1 | 2/2016 | Moloughney |

OTHER PUBLICATIONS

ULINE, Product Laser Printable Magnetic Sheets—8 1/2 x 11", Nov. 4, 2016, 1 page, ULINE at https://www.uline.com/Product/Detail/S-19175/Warehouse-Signs/Laser-Printable-Magnetio-Sheets-8-1-2-x-11?pricode=WY863&gadtype=pla&id=S-19175&gclid=Cj0KEQjw4_DABRC1tuPSpqXjxZwBEiQAhMlp69_WMToG34cyLKXtiBtvv54UMX4D6FNtYUul4w5ra6saAnnq8P8HAQ&gclsro=aw.ds, US.

Americover, 12 mil Antimicrobial Poly by Tuff Scrim, Nov. 4, 2016, 1 page, at http://www.americover.com/12_mil_antimicrobial_poly_999_prd1.htm, US.

* cited by examiner

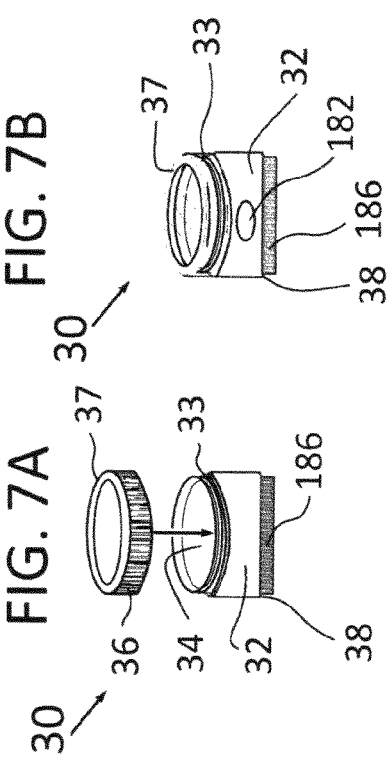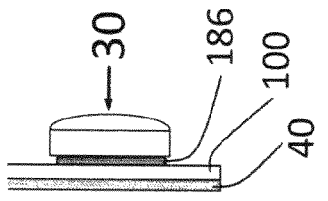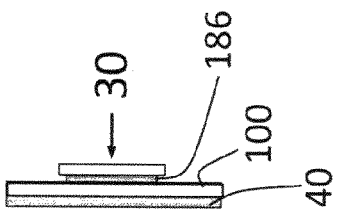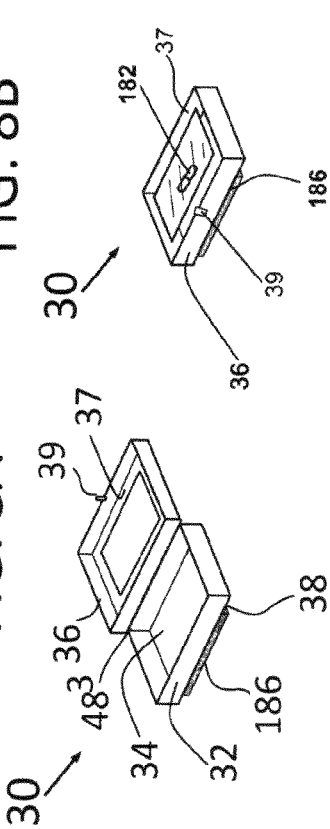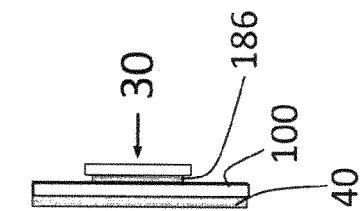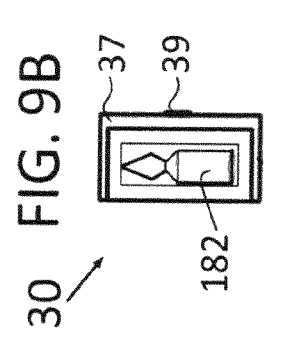

FIG. 10A

| | MEDICINE MANAGEMENT AND IDENTIFICATION INSTRUCTIONS | | |
|---|---|---|---|
| | STEPS | | 26 |
| | PERIODIC DAILY EVENT COLOR – CODE SHEET | | |
| 28 — 22 — | PERIODIC DAILY EVENT | COLOR | 24 |
| $28^1$ — $22^1$ — | First Periodic Daily Event | First Preselected Color | $24^1$ |
| $28^2$ — $22^2$ — | Second Periodic Daily Event | Second Preselected Color | $24^2$ |
| $28^3$ — $22^3$ — | Third Periodic Daily Event | Third Preselected Color | $24^3$ |
| $28^4$ — $22^4$ — | Fourth Periodic Daily Event | Fourth Preselected Color | $24^4$ |
| $28^5$ — $22^5$ — | Fifth Periodic Daily Event | Fifth Preselected Color | $24^5$ |

| | MEDICINE MANAGEMENT AND IDENTIFICATION INSTRUCTIONS | | |
|---|---|---|---|
| | STEPS | | 26 |
| | PERIODIC DAILY EVENT COLOR – CODE SHEET | | |
| 28 — 22 — | PERIODIC DAILY EVENT | COLOR | 24 |
| $28^1$ — $22^1$ — | BREAKFAST | YELLOW | $24^1$ |
| $28^2$ — $22^2$ — | LUNCH | ORANGE | $24^2$ |
| $28^3$ — $22^3$ — | DINNER | GREEN | $24^3$ |
| $28^4$ — $22^4$ — | BEDTIME | BLUE | $24^4$ |
| $28^5$ — $22^5$ — | AS NEEDED | PURPLE | $24^5$ |

20

| Periodic Daily Event Labels | | |
|---|---|---|
| First Periodic Daily Event | Breakfast | Breakfast |
| Second Periodic Daily Event | Lunch | Lunch |
| Third Periodic Daily Event | Dinner | Dinner |
| Fourth Periodic Daily Event | Bedtime | Bedtime |
| Fifth Periodic Daily Event | As Needed | As Needed |

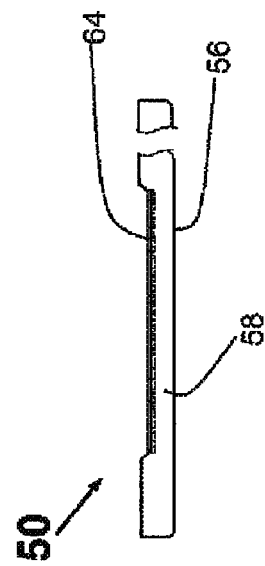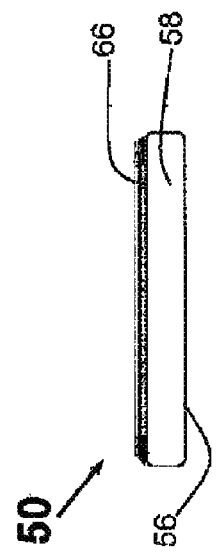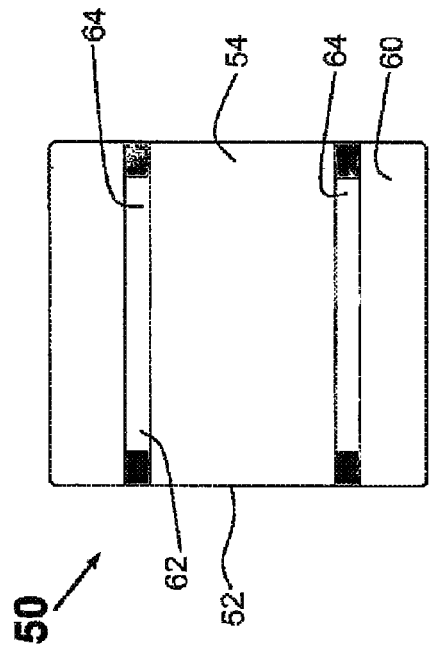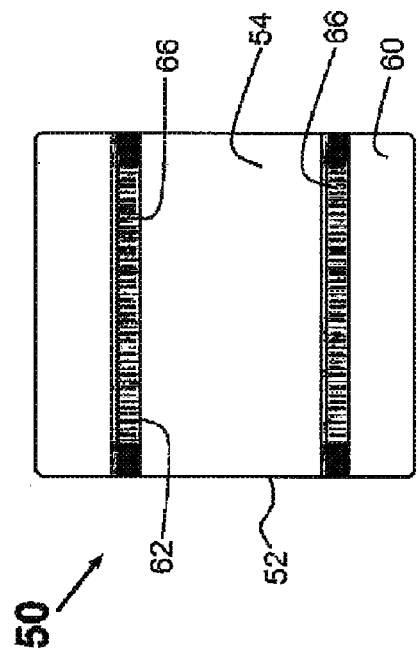

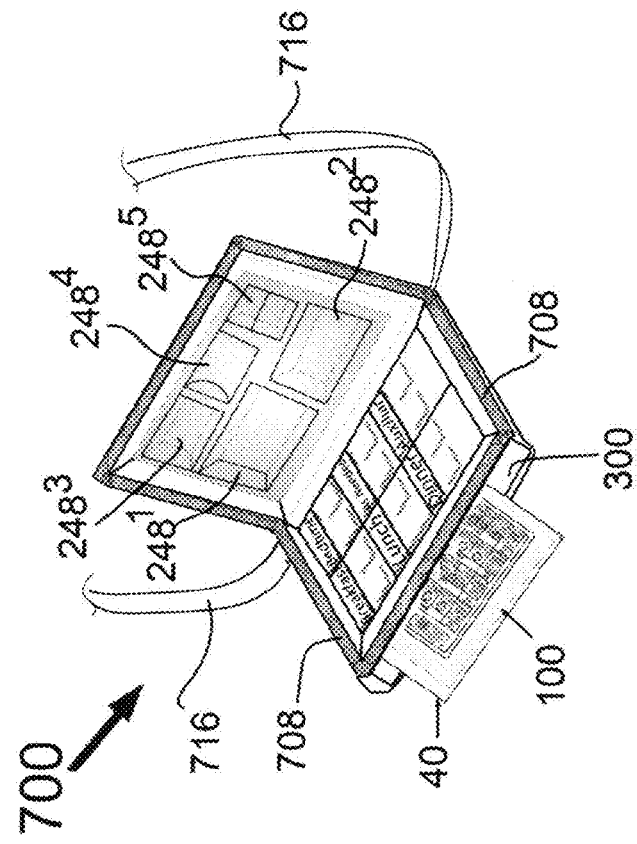
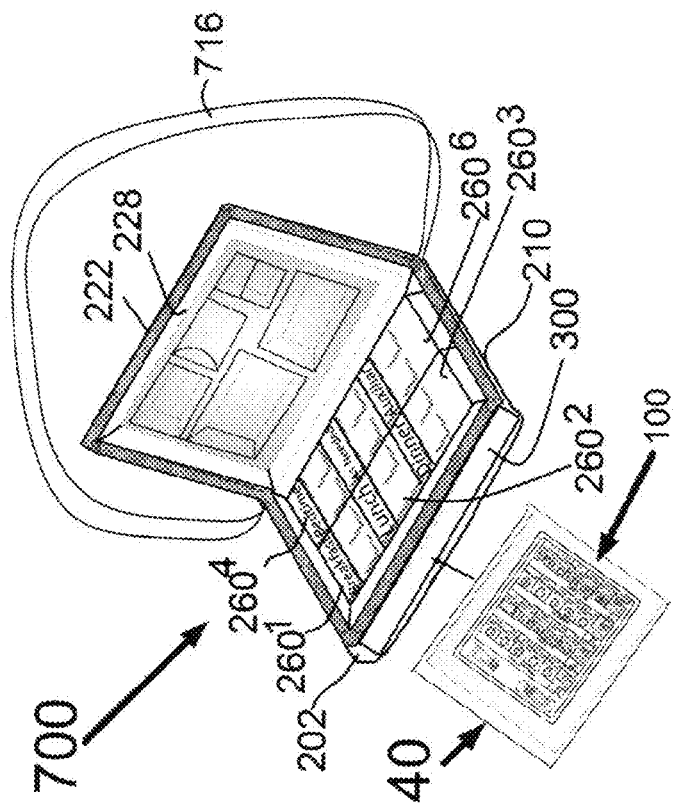

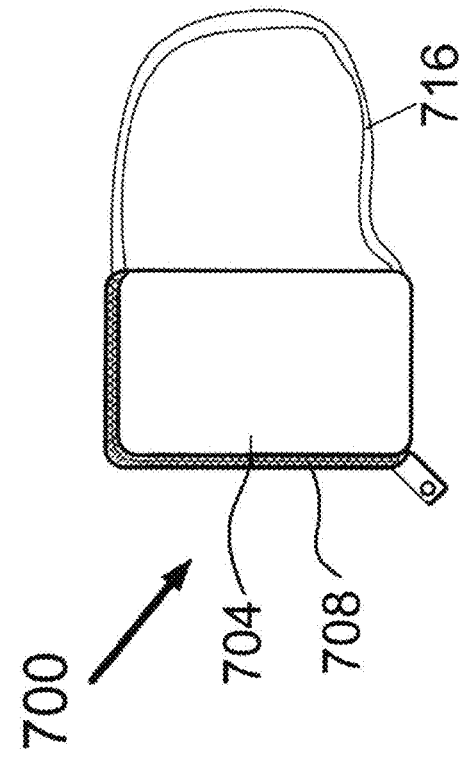
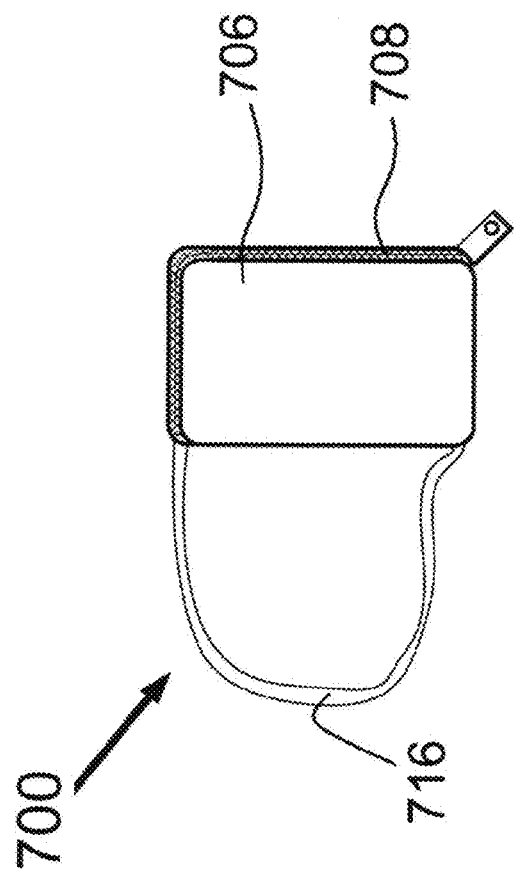

MEDICINE MANAGEMENT AND IDENTIFICATION SYSTEM AND KIT

FIELD OF THE INVENTION

The embodiments of the present invention relate to a medication management and identification system including exemplars of actual medicine products of a specific patient's medicine regimen where the exemplars are contained within a medicine exemplar container removably attached to a medicine management chart including associated information related to the actual medicine products, and removably attached to drawers within a medicine management cabinet, a daily medicine management organizer, a medicine management notebook, a mobile communication device for taking and storing current images of the medicine management charts for enabling a user, patient, caregiver, medical practitioner to keep medicine regimens of the specific patient up-to-date, correctly identify the actual medicine products for the specific patient, the time to administer the actual medicine products, and the reason for taking the actual medicine products by the specific patient, digital archive the medical management charts for the specific patient, the history of the specific patient's medicine regimen, and prevent against mismanagement of multiple medications and incorrect administration of the actual medicine products to the specific patient.

BACKGROUND

Medicine cabinets are known that allow the storage of many different types of medicine simultaneously. However, there is a need for a medicine management and identification system that identifies what different types of medicines look like and maintains the different types of medicines in an easy to access format and an easy replaceable format. Additionally, there is a need for a medicine management and identification system that is free-standing, portable and provides a record of previously taken medications selected from a plurality of prescribed medications.

It is known that a major problem in the dispensation of medication, for every medical personal, non-medical personal, or untrained medical personal, is often dispensed in error because the patient, care giver, or team of care givers, or untrained non-medical person or medical person is not familiar with what the actual prescribed medicine looks like in its appearance, including size, shape, color and smell. In addition, the medical personal, non-medical personal, or untrained medical personal, may not have immediate access to a physician's guide to look up what a particular drug looks like.

Patients frequently do not know or reasonably forget what their individual medications look like. Further, patient frequently forget to take daily timed medication on time, if at all, or alternatively misuse or overdose in the taking of medication. Medication compliance, also, typically drops off to less than fifty percent compliance when three or more different doses of medications are required on a daily basis. There are many medical conditions which critically rely upon the careful administration of drugs such as in the areas of cancer drug regimes, anti-coagulation, seizures, diabetes, narcotics, anti-biotics and cardiac medications.

The Mayo Clinic reports that nearly 70% of American people are on at least one drug, and 20% of American people are on 5 or more prescription drugs. The Washington Post, Nov. 28, 2015, reported 60% of Americans taking prescription drugs and nearly 3 in 5 take a prescription drug, up markedly since the year 2000 due to anti-depressants, treatment for high cholesterol and diabetes.

Accordingly, many different medicine managing devices have been invented to assist the patient and the care giver in taking medication in a prescribed scheduled manner. Such devices include pillboxes having a plurality of compartments, each of which include a closeable cover which can be identified with a dispensing system implementing calendaring features, for example, a different day of the week, a different time of day, or a specific date. In use of such a medicine managing device, the patient or care giver can retrieve the correct medicine from the identifiable compartment and accordingly administer the medicine to the patient. The patient or care giver, subsequently can record that the medicine was administered by the patient, or by the care giver, and that the patient ingested the medicine, the date, time, if taken with food, liquid, and quantity.

Most modern medicine managing devices require the patient, or a care giver to be familiar with the dispensation of the prescribed medicine or supplement with knowledge of challenging medical language used to identify the medicine including medical abbreviations, name brands, generic brands, together with most importantly, what the medicine actually looks like, for example the specifications of a pill, including its color, shape, size, odor; or an ampule; a patch, an emolument, and the like. Therefore, these medicine managing medicine devices implement an apparatus that is not reliably implemented by the variety of users, patients, care givers, or family members that may need to administer the medicine to the patient. Accordingly, the patient is administered the incorrect medicine.

In addition, the user, patient, or care-giver is unfamiliar with the ideal time to dispense the medicine to the patient or misplaces a prescription issued by the physician recording the frequency, time, and dosage of the medicines, along with what to take with or not to take with the dispensation of the particular medicine by itself or in combination with another drug.

It is known to many family members and care givers of loved ones that the patient may stop speaking during treatments and therapies for cancer, especially, beloved patients that are undergoing care in a hospice environment. Even more, it is known to many family ones and caregivers that the patient will lose her/his hearing partially, or completely. The modern medicine management devices do not provide a means for the patient to communicate to the family member that she/he can recognize the correct pill to be taken at the prescribed time or that the patient can point to a correct pill or ampule communicating that she/he is requesting a dosage of prescribed medicine to relieve pain.

Thus, there is a need for a personalizable medicine management system and kit for identifying actual medicine and/or supplement exemplars of the particular prescribed medicine and/or supplement for a specific patient and indication associated information so as to visually correlate the actual medicine and/or supplement with the associated information.

It is apparent that embodiments for medication organizers have been provided in the related art, which are adapted to be used by people prescribed a variety of medications by a medical practitioner. Furthermore, even though these embodiments may be suitable for the specific individual purposes to which they address, nevertheless, they would not be suitable for the purposes of the embodiments of the present invention as hereto fore described, namely a medical management system and kit personalized for a specific patient identifying actual medicine and/or supplement exemplars and indicating associated information so as to visually correlate the actual medicine and/or supplement exemplar with the associated information.

SUMMARY

In view of the above, the Applicant has tackled the problem of improving the known solutions for implementing up-to-date management of a plurality of medications for a specific patient, archiving medicine management charts of the specific patient, patient identification, medical practitioner identification, actual medicine product identification, management, and storing thereof in the exemplary embodiments of a medicine management and identification system, method, and kit personalized for a specific patient.

Thus, an object of the embodiments of the present invention is to provide a medicine management and identification system, a medicine management and identification kit, and a medicine management and identification method, for identifying actual medicine and/or supplement exemplars and indicating associated information so as to visually correlate the actual medicine and/or supplement exemplar with the associated information, which avoids the disadvantages of the known related art of administering an incorrect medication to a patient.

This summary is not an extensive overview intended to delineate the scope of the subject matter that is described and claimed herein. The summary presents aspects of the subject matter in a simplified form to provide a basic understanding thereof, as a prelude to the detailed description that is presented below. Neither this summary nor the following detailed description purports to define or limit the invention; the invention is defined only by the claims.

In use the medical management and identification system is adapted for use with a periodic daily event color-code chart, implemented together with a medicine manager chart, a periodic daily event color-code sheet, a medicine management cabinet, a mounting platform, an actual medicine product daily organizer, labels, and a mobile communications device, to ensure the correct management and identification of multiple medications to be administered to a specific patient.

The medicine manager chart provides a visual display of associated information about each of a plurality of medicines and/or supplements prescribed in a medicine regimen by a medical practitioner, collectively referred to actual medicine products, for the general health of the patient or for a diagnosed malady of the specific patient.

It is known, when the specific patient is diagnosed with a malady a prescribed medicine regimen including a plurality of different actual medicine products, for example, prescribed medicines, supplements including vitamins, the actual medicine products. The specific patient receives the prescribed medicine in a medicine container from a pharmacist, along with a printed copy of a medicine regimen of the various plurality of prescribed medicines including associated information regarding the prescribed medicines and/or supplements including pharmaceutical name, trade name, generic name, dosage, time of administration, mal effects, and combinations with other medications and/or food.

The medicine management and identification system is configured to allow for removably and/or movably attaching medicine exemplar containers containing an exemplar of each of the actual medicine products upon the medicine management chart and upon the raised front walls of each of the drawers housed within the medicine cabinet for enabling a visual identification of each of the actual medicine products.

The medicine exemplar container includes a transparent body and sealing cap sealable lid for enabling the user, patient, care giver, and/or medical practitioner to view the exemplar within the medicine exemplar container and to place an exemplar of the prescribed medicine for a particular patient, and for removing the exemplar and replacing it with a different exemplar of the exemplar of the medicine as needed.

Briefly stated, an object of the embodiment of the disclosure is to provide a personalizable medicine management and identification system for identifying correctly actual medicine products by means of the exemplar contained therewithin the medicine exemplar container and having the ability to remove and replace the exemplar of the actual medicine product when the actual medicine product is no longer prescribed to the specific patient and/or the actual medicine product prescribed has changed. In addition, the medicine management and identification system provides a means to indicate and change keep current the associated information related to each of the actual medicine products prescribed to the specific patient by means of preprinted labels removably attached to the medicine management chart including the name, dosage, method of administration, and dosage of each of the actual medicine products in the specific patient's medicine regime. In addition, the medical reason for taking the actual medicine product is provided by means of preprinted labels removably attached to the medicine management chart.

The embodiment of the subject matter of the present invention relates to a medicine manager system including a visual exemplar of an actual medicine product and/or supplement contained in a medicine exemplar container which is removably attachable to a medicine management chart and in a remote medicine exemplar container removably attached to a drawer within a medicine management cabinet to enable correctly identifying pills or supplements when multiple medications or supplements are prescribed and stored for a specific patient to enable the prevention of incorrectly administering an incorrect actual medicine product or supplement to a patient.

The exemplar of the actual medicine product contained therewithin the medicine exemplar container is displayed on the medicine management chart where associated information which is personalized to the specific patient's medical regimen is, also, displayed so that a patient, user, caretaker, medical practitioner can correctly correlate the identification of the actual medicine product, the time to administer or take the actual medicine product, the dosage of the actual medicine product, the reason the actual medicine product is taken, and the reason for taking the actual medicine product. The medicine manager system and kit includes a color coded scheme associated with periodic daily events of the specific patient's day at which time the specific patient is prescribed to take.

The medicine management and identification system is, also, provided as a kit in accordance with an embodiment of the disclosure. The medicine management and identification system is, also, provided as a method in accordance with an embodiment of the disclosure.

The novel medicine management and identification system solves a problem that users, patients, caregivers, family members, medical practitioners are challenged with when challenged with the task of managing and identifying a plurality of actual medicine products, including supplements for a specific patient prescribed by one or more medical practitioners. The user, patient, caregiver, family member, medical practitioner are not always coordinated in their care and treatment towards the specific patient, thereby confusing the specific patient which can cause potential adverse drug interactions. It is not uncommon for a specific patient to have a plurality of prescription medications and supplements for different ailments and conditions, without any single prescriber knowing the entire medical regimen being administered to the specific patient.

The medicine management and identification system, kit and method solves this problem by providing a central medicine management and identification system that can be positioned in a central location within the specific patient's home, the administration of the plurality of actual medicine products are organized by periodic daily events of the specific patient's day. The medicine manager chart, in one aspect, provides the correct visual identification of each of the actual medicine products to be administered to the patient and in another aspect provides a visual known medical reason for administering the actual medicine product to the specific patient, and a correct identification of the specific patient, and a correct identification of the medical practitioner of the specific patient.

The medicine management and identification system is easy to use by the user, the patient, family members, care givers, and medical practitioners. The medicine management and identification system can be easily manipulated when changes in the specific patient's medicine management chart need to be made indicative of changes in the specific patient's medical regimen, including dosages, new medications, discontinuing old medications, etc. In addition, the medicine management and identification system provides proper storage of the plurality of actual medicine products and auxiliary products.

The novel features considered characteristic of the embodiments of the present invention are set forth in the appended claims solves this problem. The embodiments of the present invention, however, both as to their construction and to their method of operation together with additional objects and advantages thereof will be best understood from the following description of the specific embodiments when read and understood in connection with the accompanying figures of the drawing.

BRIEF DESCRIPTION OF THE DRAWINGS

For a fuller understanding of the nature and advantages of the embodiments of the present invention, as well as the preferred mode of use thereof, reference should be made to the following detailed description, read in conjunction with the accompanying drawings. In the drawings, like reference numerals designate like or similar steps or components.

FIG. 7A is a perspective view of a medicine exemplar container having a circular configuration, according to an embodiment of the disclosure.

FIG. 7B is a perspective view of the medicine exemplar container of FIG. 7A having an exemplar of an actual medicine product contained therewithin, according to an embodiment of the disclosure.

FIG. 7C is a side perspective view of the medicine exemplar container of FIG. 7B.

FIG. 8A is a perspective view of a medicine exemplar container having a rectangular configuration, according to an embodiment of the disclosure.

FIG. 8B is a perspective view of the medicine exemplar container of FIG. 8A having an exemplar of an actual medicine product contained therewithin, according to an embodiment of the disclosure.

FIG. 8C is a side perspective view of the medicine exemplar container of FIG. 8B.

FIG. 9A is top planar view of a medicine exemplar container having an elongated rectangular configuration, according to an embodiment of the disclosure.

FIG. 9B is a top planar view of the medicine exemplar container of FIG. 9A having an ampule contained therewithin, according to an embodiment of the disclosure.

FIG. 10A is a front planar view of a periodic daily event color-code sheet, according to an embodiment of the disclosure.

FIG. 10B is a front planar view of a periodic daily even color-code sheet of FIG. 10A showing a color corresponding to a periodic daily event of the day, according to an embodiment of the disclosure.

FIG. 15A is a top planar view of a mounting platform showing two recessed U-channels, according to an embodiment of the disclosure.

FIG. 15B is a side perspective view of one of the recessed U-channel platform of FIG. 15A, according to an embodiment of the disclosure.

FIG. 16A is a top perspective view of a platform showing two raised U-channels, according to an embodiment of the disclosure.

FIG. 16B is a side perspective view of one of the raised U-channels of FIG. 16A, according to an embodiment of the disclosure.

FIG. 35A is a perspective view of a mini-medicine management cabinet and a medicine management chart, according to an embodiment of the disclosure.

FIG. 35B is a perspective view of the mini-medicine management cabinet and the medicine management chart of FIG. 35A, according to an embodiment of the disclosure.

FIG. 35C is a front perspective view of the mini-management cabinet of FIG. 35A in a closed position, according to an embodiment of the disclosure.

FIG. 35D is a rear perspective view of the mini-management cabinet of FIG. 35A in a closed position, according to an embodiment of the disclosure.

DETAILED DESCRIPTION

Figure 1:
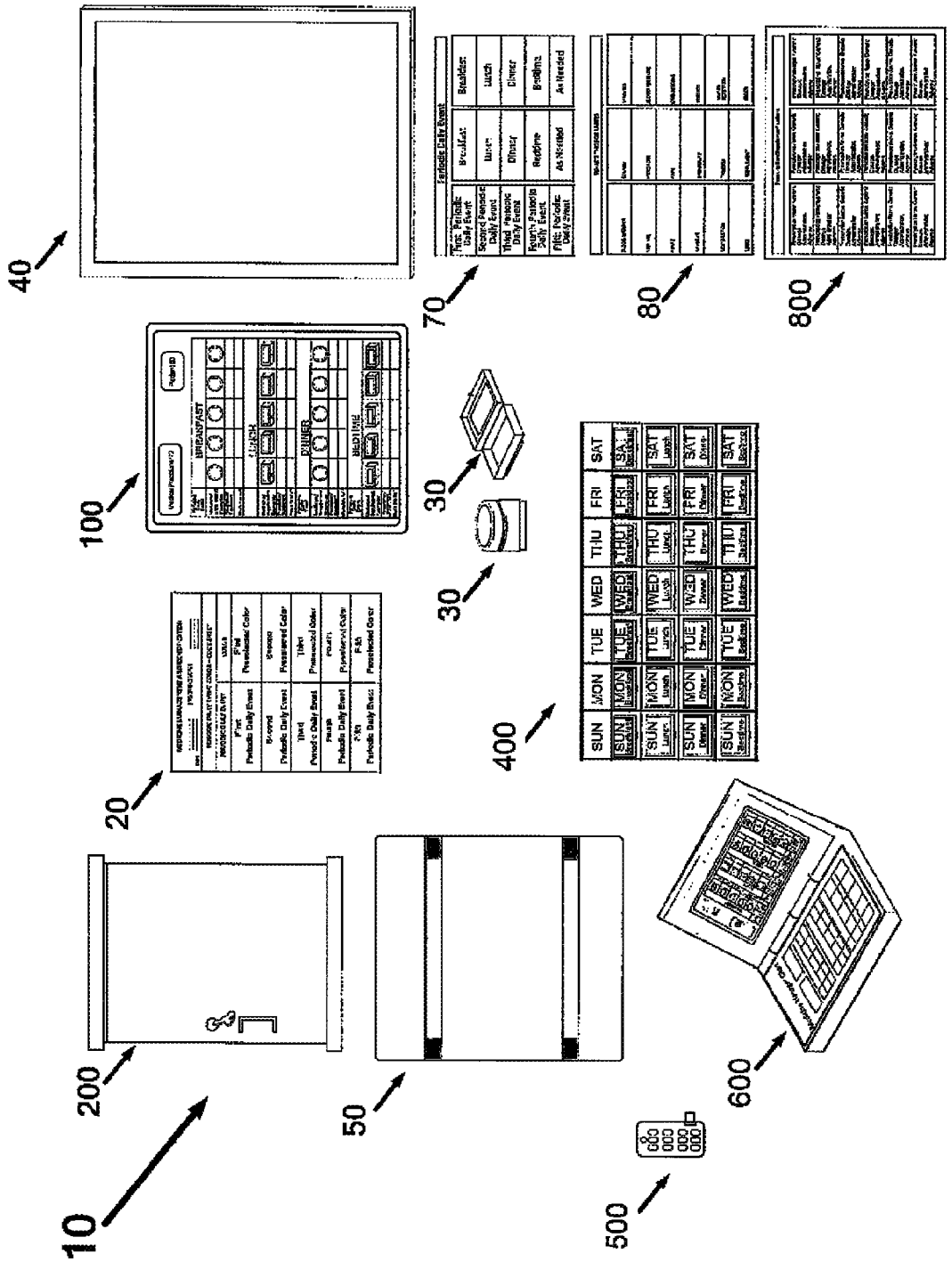
FIG. 1 is a illustrative view of a medicine management and identification system in accordance with an embodiment of the disclosure.

In the following, a solution according to exemplary and non-limitative embodiments of a medicine management and identification system, method, and kit will be presented and described in detail. The enemy of managing a plurality of medications of actual medicine products is a bad memory, lack of knowledge of what the actual medicine product looks like, variable places for storing the plurality of medications of actual medicine products, lack of information of the reason for administering the plurality of medications to the patient, one or more medical regimens for the specific patient, and variable caretakers, family members, and medicine practitioners managing the plurality of medications of actual medicine products. For the purpose of promoting an understanding of the principles of the disclosure herein, reference will be made to the embodiments illustrated in the drawings and specific language will be used to describe the same. It will, nevertheless, be understood that no limitation of the scope of the disclosure is thereby intended; any alterations and further modifications of the described or illustrated embodiments and any further applications of the principles of the disclosure as illustrated therein are contemplated as would normally occur to one skilled in the art to which the disclosure relates. All limitations of scope should be determined in accordance with and as expressed in the claims.

Referring now to FIGS. 1-38 in which like numeral indicate like parts, and particularly FIGS. 1-38, are illustrative views of a medicine management and identification system, method, and kit, according to embodiments of the present disclosure. Referring to FIG. 1 the medical management and identification system 10 includes a portable rigid magnetic board 40, a periodic daily event color-code sheet 20, one or more medicine management charts 100, a medicine management cabinet 200, a plurality of medicine exemplar containers 30, a mounting platform 50, an actual medicine product daily organizer 400, a mobile communication device 500, and a medicine management notebook 600, and one or more sheets of preprinted periodic daily event labels 70, one or more sheets of preprinted What's this for? labels 80, one or more sheets of Prescription/Supplement labels 800.

The present disclosure is directed to identifying and managing a plurality of medications of actual medicine products 180 to be administered to a specific patient for one or more medical regimens of the specific patient for use by a user, patient, caregiver, medical practitioner. The patient in an embodiment of the disclosure can be an elder patient, an adult patient, a child patient, a newborn patient, and a pet animal. With specific reference to FIGS. 1, 2, 3, 6, 14, 18A, and 24, a portable rigid magnetic board 100 is used to support a medicine management chart 100 when the medicine management and identification system 10 is in use by a user, a patient, a care giver, or a medical practitioner. The term user can be used to identify the user, the patient, the care giver, family member, or the medical practitioner.

Figure 14:
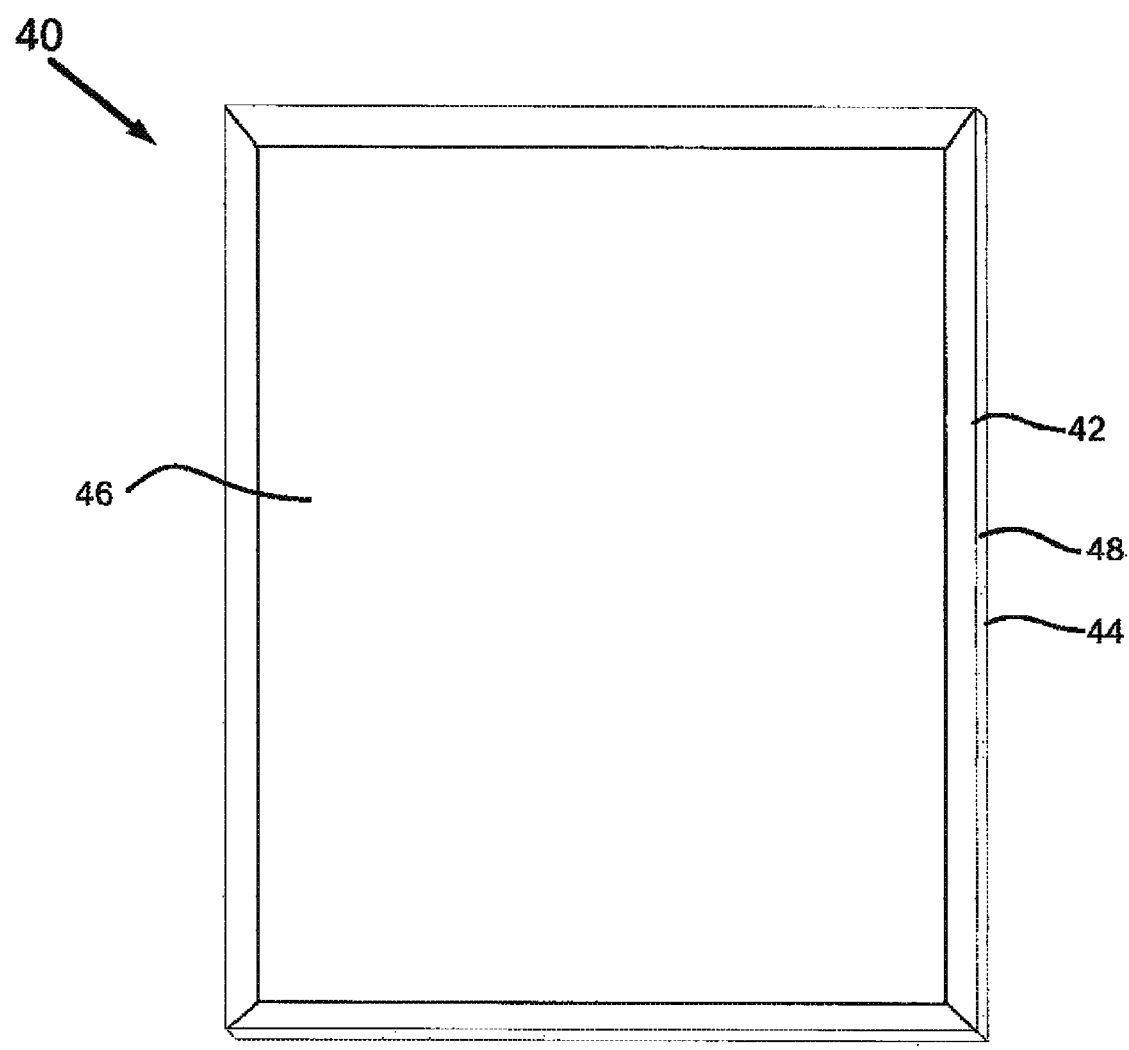
FIG. 14 is a front planar view of a portable rigid magnetic board, according to an embodiment of the disclosure.

As shown in FIG. 14, a portable rigid ferromagnetic substrate 42 is adapted and operable to act as a portable rigid magnetic board 40 so as to receive and retain medicine exemplar containers 30 having a mateable mounting magnet 186 of a plurality of mateable mounting magnets 186 for enabling removably attaching the medicine manager chart 100 thereupon the portable rigid magnetic board 40 so that the associated information 184 therein the medicine management chart 100 can be received, retained, displayed, ascertained, and viewed by the user.

FIG. 14 illustrates the portable rigid magnetic board 40 which implements the display of the medicine management chart 100. The portable rigid ferromagnetic substrate 42 includes two layers, a first layer including a thin washable exterior surface 46 supported by a second layer including a ferromagnetic layer 48, wherein the ferromagnetic layer 48 is magnetically attractable so as to receive and removably attach one or more of the plurality of mateable mounting magnets 186, and a magnetic flux is passable therethrough the thin washable exterior surface 46 so that the portable rigid ferromagnetic substrate 42 acts as a portable rigid magnetic board 40 for enabling the display of the medicine management chart 100. The portable rigid ferromagnetic substrate 42 and the ferromagnetic layer are supported by a rear rigid mounting board 44.

Figure 17:
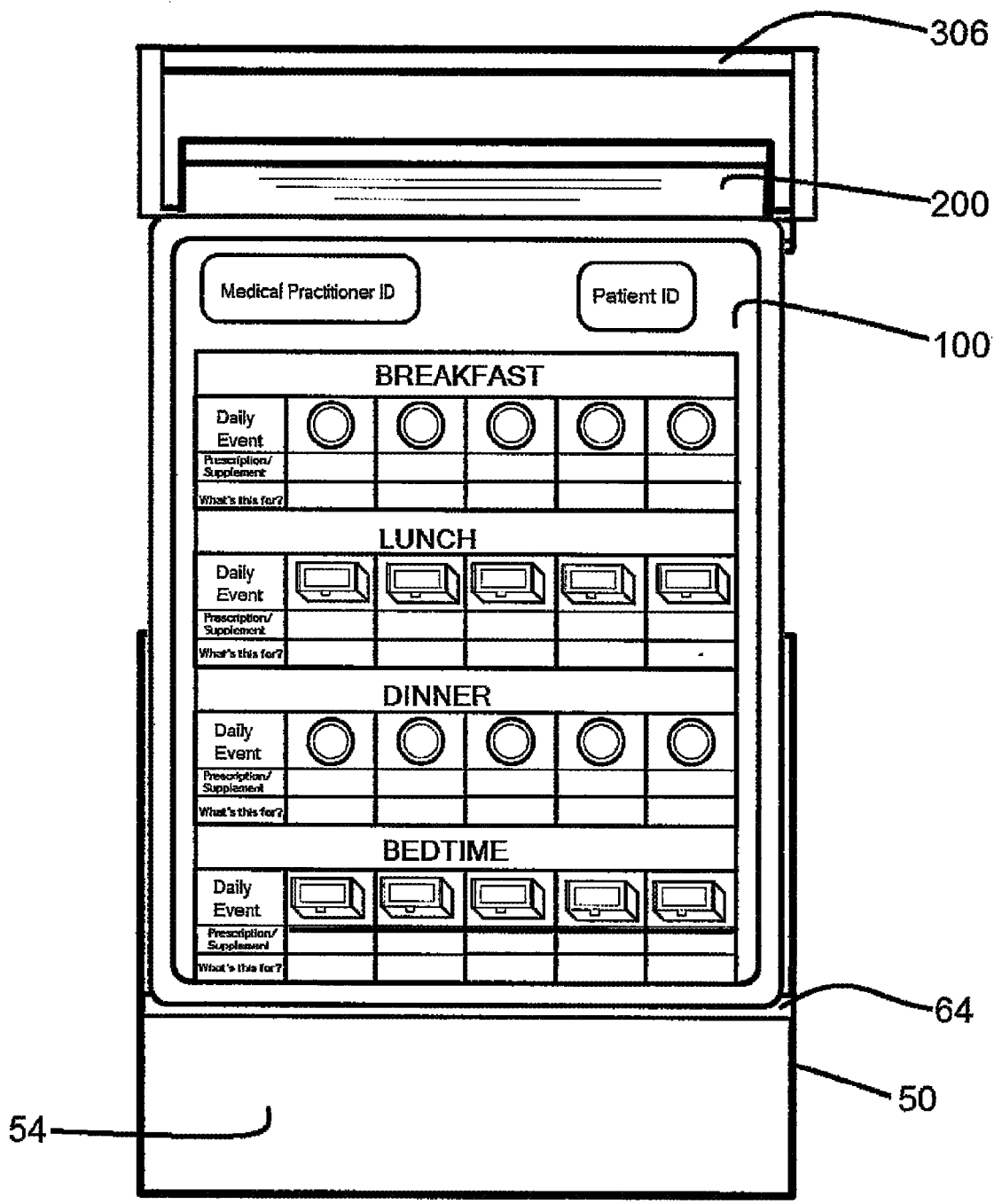
FIG. 17 is a front perspective view of a medicine management chart supported by the mounting platform, according to an embodiment of the disclosure.
Figure 18A:
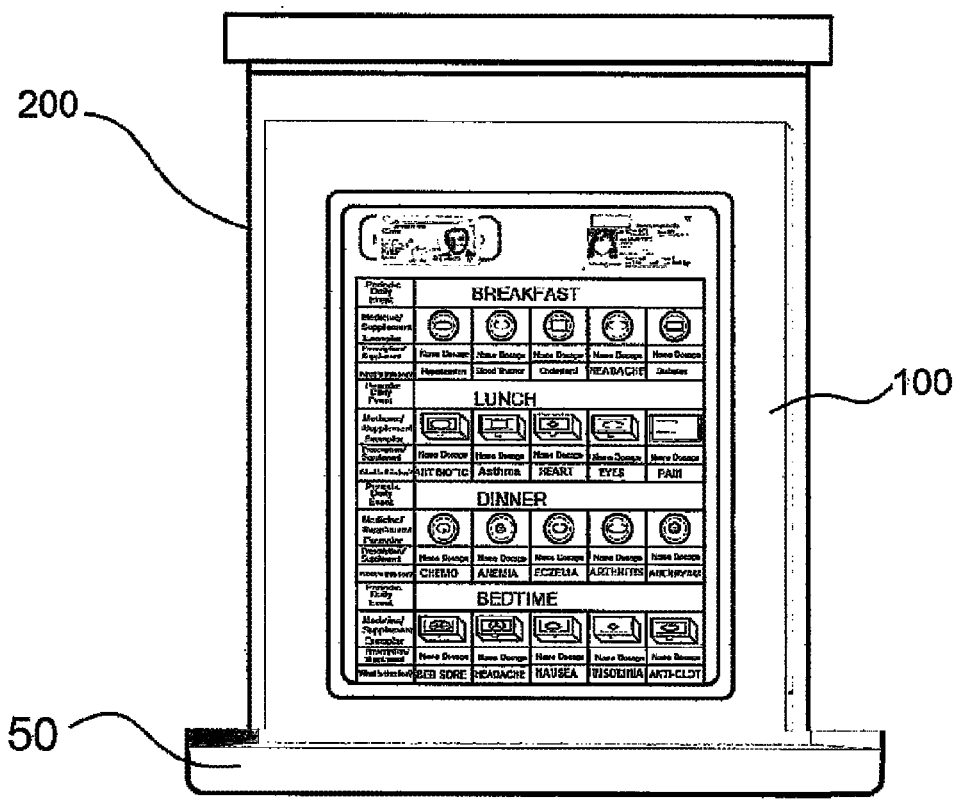
FIG. 18A is a front perspective view of a medicine management chart in use, according to an embodiment of the disclosure.
Figure 24:
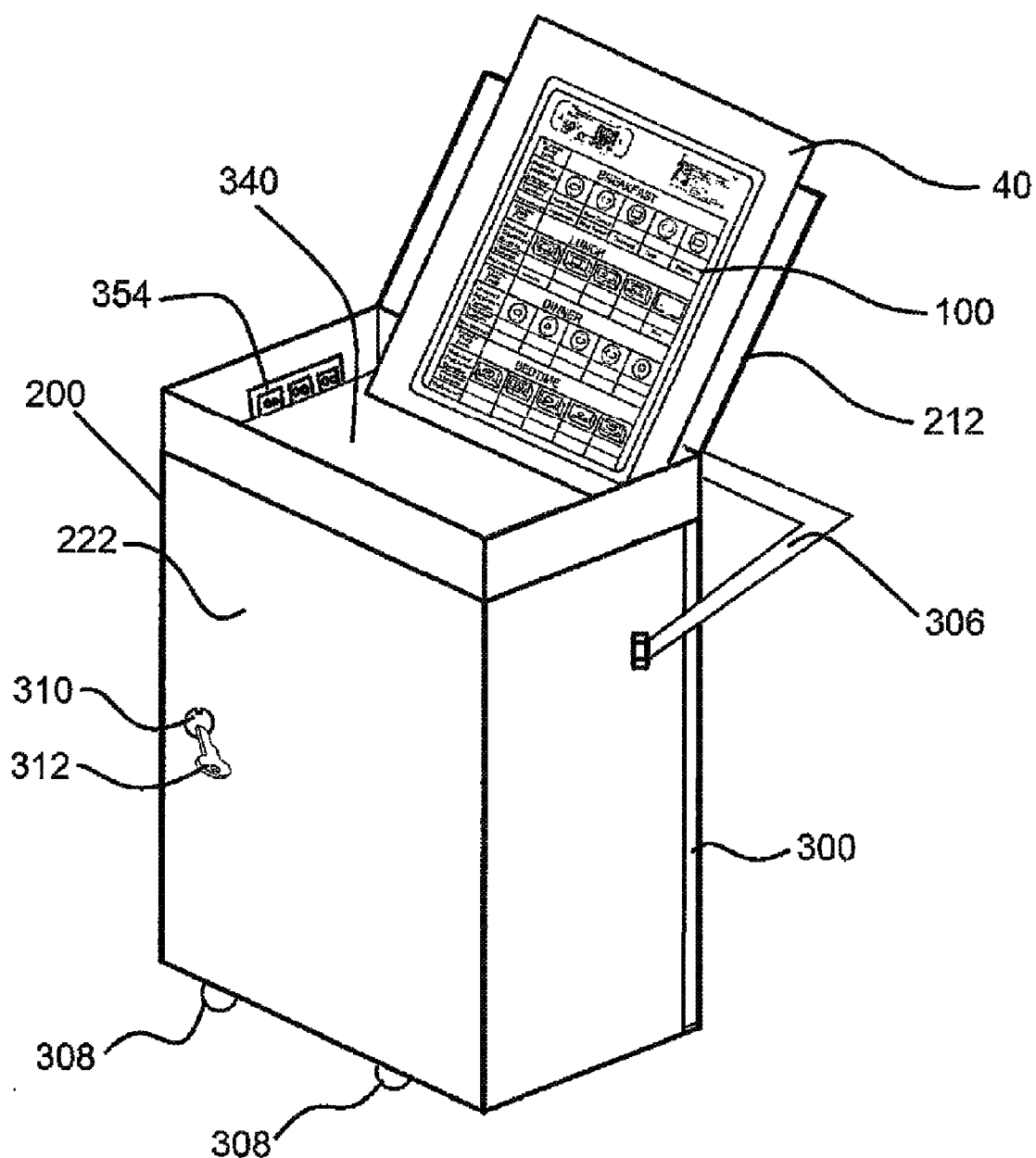
FIG. 24 is a side perspective view of a medicine management cabinet showing a medicine management chart displayed against an open top wall of a medicine management cabinet, according to an embodiment of the disclosure.
Figure 25:
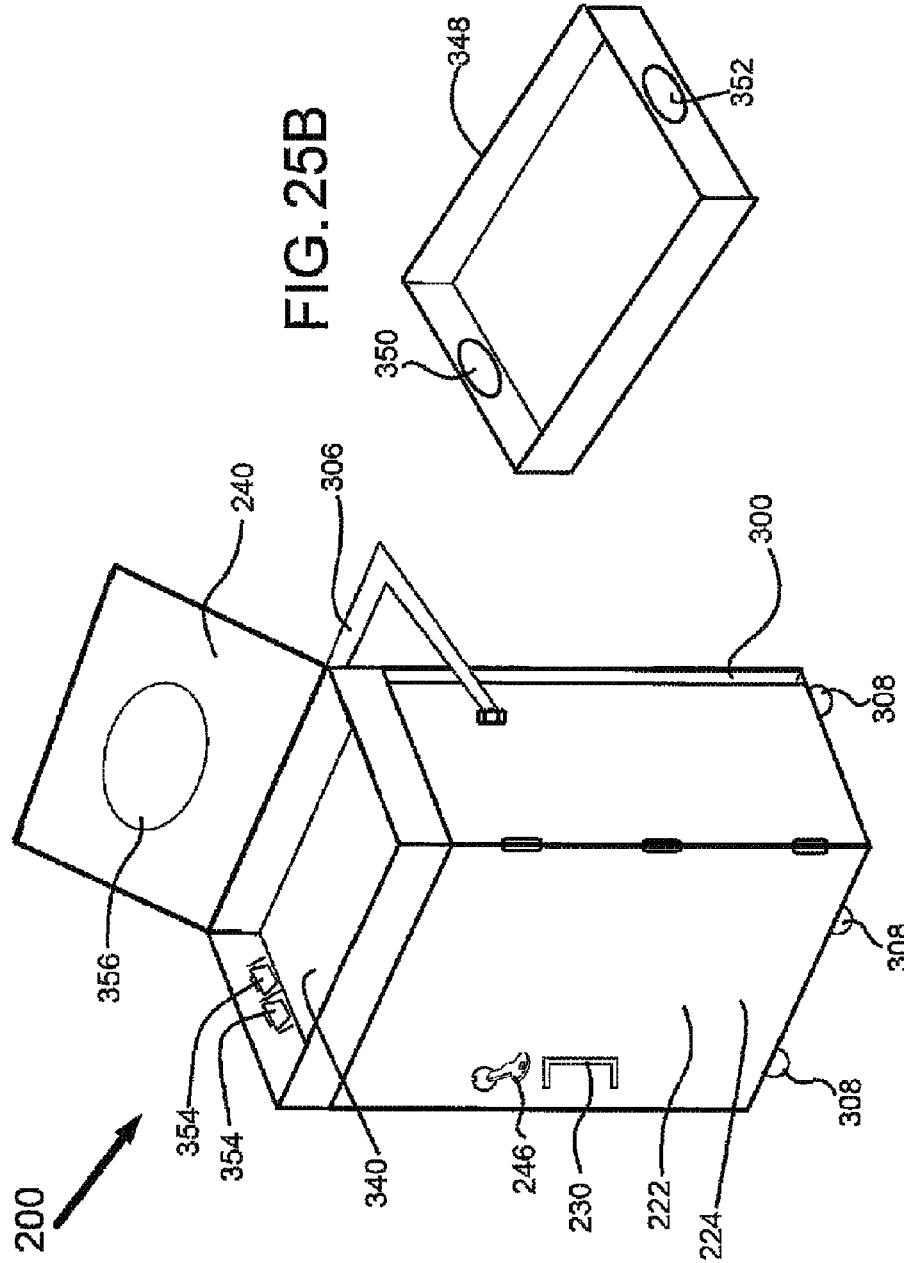
FIG. 25A is a perspective view of a top open region and a mirror of the medicine management cabinet, according to an embodiment of the disclosure.
FIG. 25B is a perspective view of a medicine management cabinet showing a removable tray of a medicine management cabinet, according to an embodiment of the disclosure.
Figure 26:
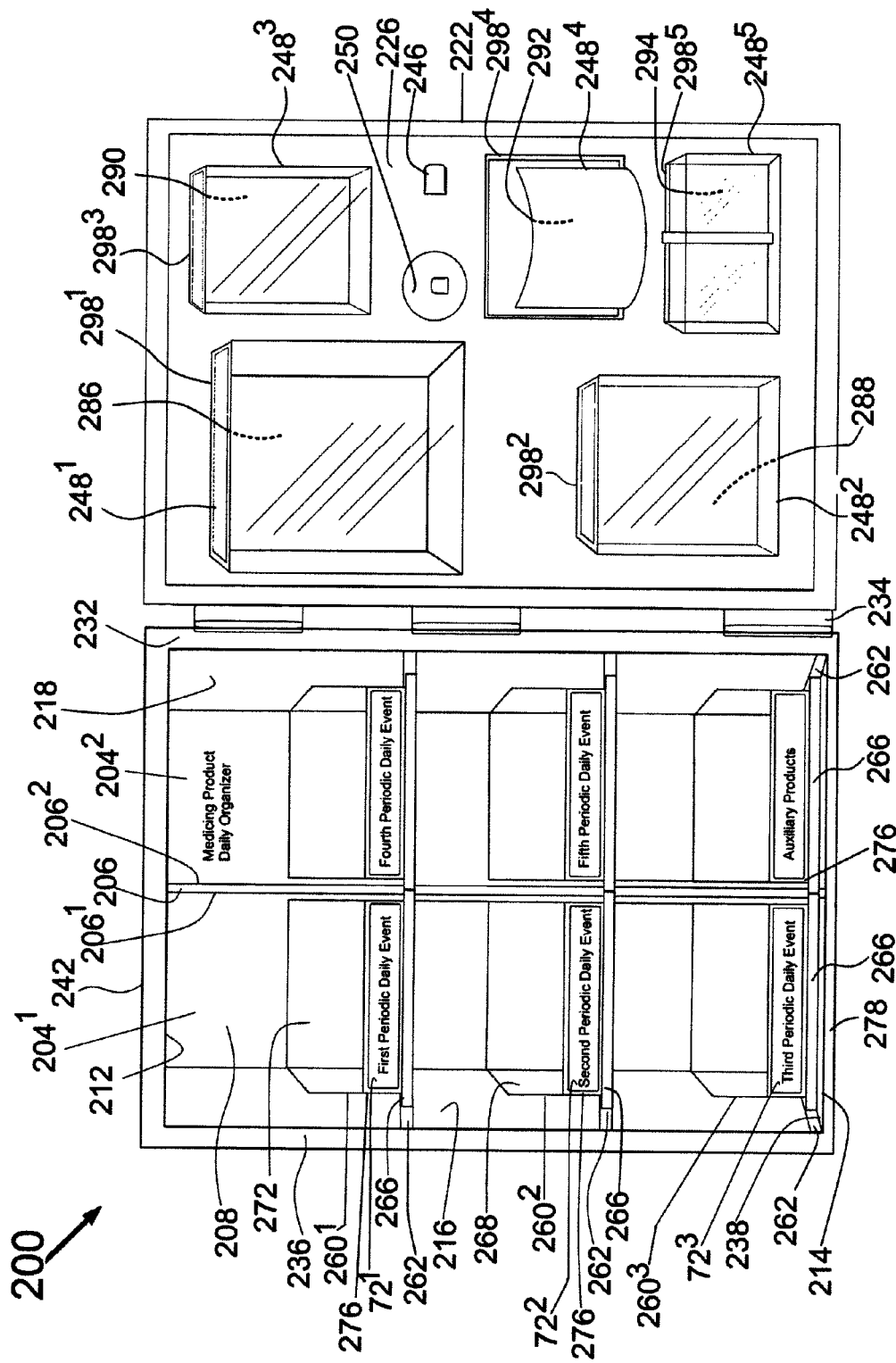
FIG. 26 is a front perspective view of a medicine management cabinet in the open position, according to an embodiment of the disclosure.

FIGS. 17, 18A, and 24, illustrates the medicine manager chart 100 removably attached to the portable rigid magnetic board 40. As shown, the medicine manager chart 100 in use is removably attached to the portable rigid magnetic board 40 by use of one or more medicine exemplar containers 30, whereon a mateable mounting magnet 186 is attached to the one or more medicine exemplar containers 30, and the portable rigid magnetic board 40 having the medicine management chart 100 removably attached thereon is leaned against the medicine management cabinet 200 while the medicine management cabinet 200 is generally placed on top of the mounting platform 50. The portable rigid magnetic board includes a length ($l^2$), a width ($w^2$), and a thickness ($t^2$). In the exemplary embodiment of the disclosure the portable rigid magnetic board includes the length ($l^2$) of about 22½ inches, a width ($w^2$) of about 17.00 inches, and a thickness ($t^2$) of about ¾ inches.

Figure 22:
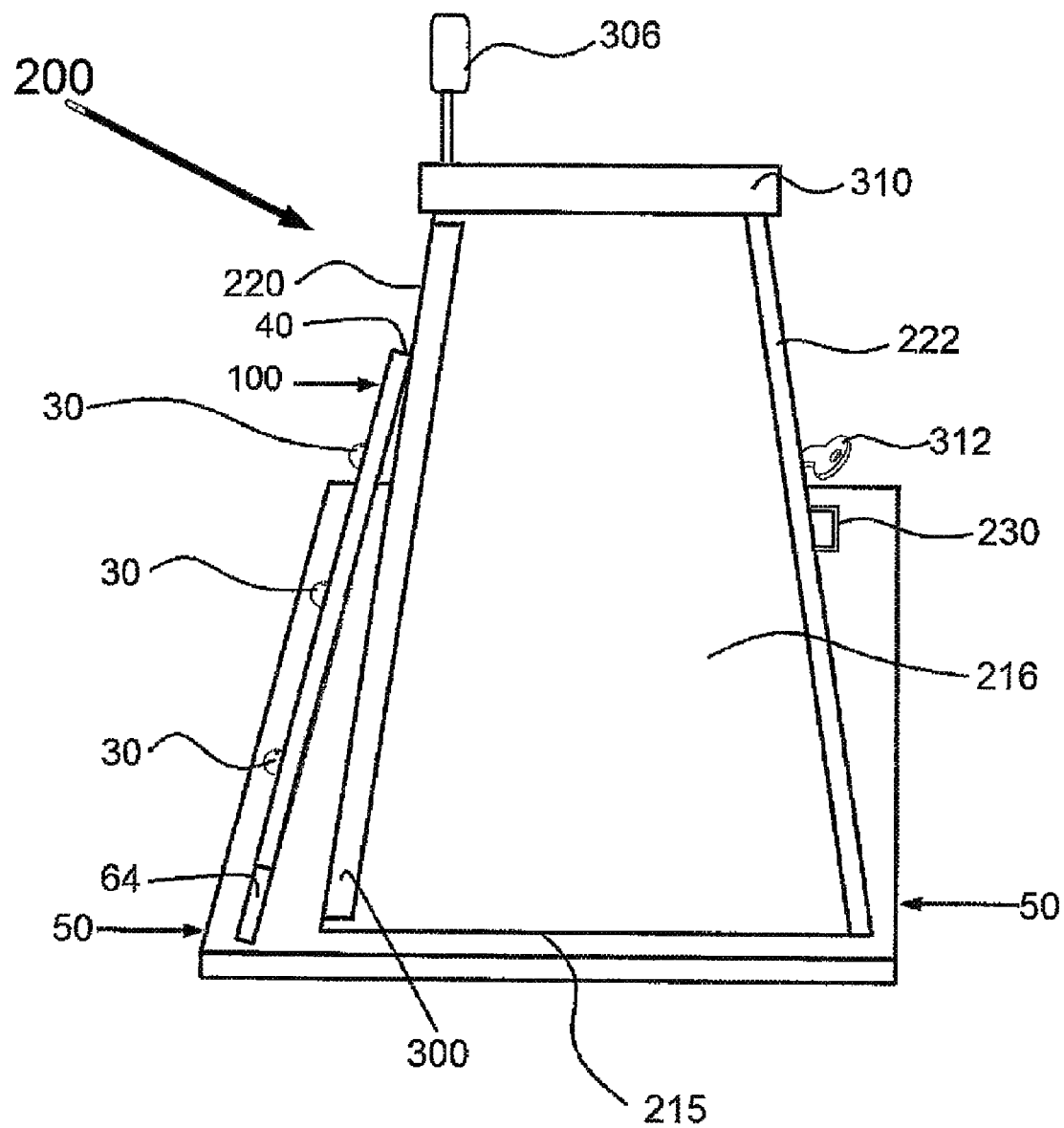
FIG. 22 is a side perspective view of the medicine management cabinet of FIG. 21 in use with a medicine management chart, according to an embodiment of the disclosure.

FIGS. 1, 15A-15B, and 16A-16B, illustrate the mounting platform 50. FIGS. 17, 18A, and 22, illustrate the mounting platform 50 implemented with the medicine management chart 100. The mounting platform 50 provides a supporting means and a displaying means to the portable rigid magnetic board 40 when in use with the medicine management chart 100 releasably attached thereon the portable rigid magnetic board 40. The mounting platform 50 enables against the portable rigid magnetic board 40 sliding downwards away from a medicine management cabinet 200 due to gravitational force.

As shown in FIGS. 1, 15A-15B, and 16A-16B, the mounting platform 50 includes a preformed body 52 and is typically manufactured from a rigid, durable material, including fiberglass, melamine, stainless steel, wood, plastic, metal, polymers, custom plastic from materials with built-in antimicrobial and antibacterial properties that help to resist the growth of bacteria, mold, mildew, fungi, viruses and other microbes, and any combination thereof ensuring the mounting platform 50 performs its intended function. It is beneficial that the mounting platform 50 be manufactured with a resilient material so that the mounting platform 50 can be cleaned without degradation during cleaning by conventional recognized methods such as the use of a base solution, or an acid solution.

In another embodiment of the disclosure the mounting platform 50 is manufactured from a malleable material including a silicone with fiberglass substrate. An example of the silicone with fiberglass substrate is Silpat.

The preformed body 52 of the mounting platform 50 includes a rectangular shape having a length (I), a width (w) and a thickness (t) that is selected with reference to a length and width of the medicine management cabinet 200 such that the medicine management cabinet readily fits upon the mounting platform 50. In an embodiment of the disclosure the mounting platform 50 includes a length (I) of about 23½ inches, having a width (w) of about 18.00 inches, and a thickness (t) of about ¾ inch. The mounting platform 50 in the exemplary embodiment is rigid and has a thickness such that the mounting platform 50 maintains its shape and form. The mounting platform 50 includes a top side 54 and a bottom side 56 and a solid interior portion 58. The top side 54 and the bottom side 56 each are encapsulated by an exterior surface 60.

Further, according to an exemplary embodiment of the disclosure, the mounting platform 50 is configured to be positioned beneath the medicine management cabinet 200 so that the mounting platform 50 extends beyond the size of the medicine management cabinet 200.

Referring to FIGS. 15A-15B and 16A-16B, according to an embodiment of the disclosure, the mounting platform 50 includes a mounting means 62 integrally machined within the preformed body 52. More particularly, as shown in FIGS. 15A-15B, in an embodiment of the present disclosure, the mounting means 62 is one or more of recessed U-channels 64 integrally machined within the exterior surface 60 of the preformed body 52 adapted and operable for providing the portable rigid magnetic board 40 to be seated within the recessed U-channel 64 so that the portable rigid magnetic board 40 is prevented from sliding downwards due to the force of gravity. The one or more of the recessed U-channels 64 is configured to allow the portable rigid magnetic board 40 to be easily seated therein when in use for enabling the display of the medicine management chart 100 to the user, patient, caregiver, family member, medical practitioner.

In an embodiment of the disclosure, the recessed U-channel 64 can include a ferromagnetic material that is attracted to the portable magnetic board 40 to ensure for a secure positioning of the portable magnetic board 40 when the medicine management chart 100 is releasably attached thereon.

As shown in FIGS. 16A-16B, in an embodiment of the disclosure, the mounting means 62 is one or more of raised U-channels 66 integrally machined extending upward from the exterior surface 60 of the preformed body 52 of the mounting platform 50 adapted and operable for providing the portable rigid magnetic board 40 to be seated against the raised U-channel 66 so that the portable rigid magnetic board 40 is prevented from sliding downwards due to the force of gravity.

In an embodiment of the disclosure, the raised U-channel 66 can include a ferromagnetic material that is attracted to the portable magnetic board 40 to ensure for a secure positioning of the portable magnetic board 40 when the medicine management chart 100 is releasably attached thereon.

A periodic daily event color-code sheet 20, as shown in FIGS. 1, 10A and 10B, is provided as an integral part of the medicine management and identification system 10 and medicine management and identification kit 900, and medicine management and identification method 1100 to visually correlate a periodic daily event 22 of a day with a color 24, wherein the periodic daily event 22 of the day is preselected from a variety of different periodic daily events $22^{1-n}$ of the day, and the color 24 is preselected from a variety of different colors $24^1$-$24^n$ and to provide the user, patient, caregiver, family member, medical practitioner with instructions 26 for use of the medicine management and identification system 10.

The instructions 26 for use of the periodic daily event color-code sheet 20, are instructions 26 to be executed directly by the user, patient, caregiver, family member, medical practitioner to be implemented with the medicine management and identification system including the medicine management chart 100; the medicine management cabinet 200; and the actual medicine product daily organizer 400. The instructions 26 can include a preselected periodic daily event of the day, or time of day, preselected range of time during a day arranged in a chronological arrangement, and a preselected color-code associated with the preselected periodic daily event of the day, time of day, or range of time during a day arranged in the chronological arrangement.

As shown in FIGS. 10A-10B, in an exemplary embodiment of the disclosure, the periodic daily event color-code sheet 20 includes one or more color-coded rows $28^1$-$28^5$. Visually, each of the color-coded rows $28^1$-$28^5$ is completely shaded in a different color 24 of the variety of different colors $24^1$-$24^5$ and each row $28^1$-$28^5$ includes a viewing text of a periodic daily event 22 of a day preselected from the variety of different periodic daily events $22^1$-$22^5$ of the day preprinted thereon, for enabling for visually correlating each of the colors 24 of variety of different colors $24^1$-$24^5$ with the corresponding periodic daily events 22 of the day of the number of different daily events of the day $22^1$-$22^5$ preprinted thereon. Thereby, each of the variety of different colors $24^1$-$24^5$ with the periodic daily event of the day $22^1$-$22^5$ preprinted thereon visually identifies to the user, patient, caregiver, medical practitioner at which time of the day a specific patient is to be administered one or more of a multiple of actual medicine products 180 of a medicine regimen for the specific patient.

As known, the actual medicine product 180 of the multiple of actual medicine products 180 can be any type of actual medicine product 180, including, but not limited to, pills, pills in gel form, liquid medicine in ampules $182^4$, drops, ointments, salves, patches, needles, powders, oils, and vitamins, supplements, epi pens, tinctures, and the like.

Referring to FIGS. 10A-10B, in combination, a first row $28^1$ of the periodic daily event color-code sheet 20 includes a first color $24^1$ of the variety of different colors $24^1$-$24^n$ which is yellow $24^1$ and bears the viewing text$^1$ of a first periodic daily event of the day $22^1$, Breakfast $22^1$, depicting the first periodic daily event $22^1$ of the day the specific patient is to be administered actual medicine product 180 as implemented on the medicine management chart 100, explained in more detail, below. A second row $28^2$ of the periodic daily event color-code sheet 20 includes a second color $24^1$ of the variety of different colors $24^1$-$24^n$ which is orange $24^2$ and bears the viewing text$^2$ of a second periodic daily event of the day $22^2$, Lunch $22^2$, depicting the second periodic daily event of the day $22^2$ the specific patient is to be administered actual medicine product 180 as implemented on the medicine management chart 100. A third row $28^3$ of the periodic daily event color-code sheet 20 includes a third color $24^3$ of the variety of different colors $24^1$-$24^n$ which is green $24^3$ and bears the viewing text$^3$ of a third periodic daily event of the day $22^3$, Dinner $22^3$, depicting the third periodic daily event of the day $22^3$ the specific patient is to be administered actual medicine product 180 as implemented on the medicine management chart 100. A fourth row 284 of the periodic daily event color-code sheet 20 includes a fourth color $24^4$ which is blue $24^3$ and bears the viewing text$^4$ of a fourth periodic daily event of the day $22^4$, Bedtime $22^4$, depicting the third periodic daily event of the day $22^3$ the specific patient is to be administered actual medicine product 180 as implemented on the medicine management chart 100. A fifth row $28^5$ of the periodic daily event color-code sheet 20 includes a fifth color $24^5$ which is purple $24^5$ and bears the viewing text$^5$ of a fifth periodic daily event of the day $22^5$, As Needed $22^5$, depicting the periodic daily event of the day $22^5$ when a patient is to be administered actual medicine product 180. For example, here, the specific patient may need to take a pain pill, or ampule $182^4$ of pain medicine, when the patient is experiencing pain before the periodic daily event of the day 22 at which it was prescribed by the medical practitioner. The As Needed $22^5$ can be implemented on a medicine management chart 100 in another embodiment to the disclosure.

The periodic daily event color-code sheet 20 depictions control the colors $24^{1-5}$ and the periodic daily events $22^{1-5}$ of the day for other components of the medicine management and identification system 10. By way of example, the colors $24^{1-4}$, yellow $24^1$; orange $24^2$; green $24^3$; blue $24^4$; and the periodic daily events of the day $22^{1-4}$; Breakfast $22^1$; Lunch $22^2$; Dinner $22^3$; Bedtime $22^4$; are adopted onto the medicine management chart 100 for the specific patient, as shown in FIGS. 2, 3, 4, 5A-5E; and adopted onto the actual medicine product daily organizer 400, as shown in FIGS. 30A-30B, 31, and 32; and adopted onto the plurality of drawers $260^{1-6}$ within the medicine management cabinet 200, as shown in FIGS. 26, 27, 28, 29 and 37, each of which are explained in more detail, below.

In an embodiment of the disclosure, the periodic daily event color-code sheet 20 includes a fifth periodic daily event $22^5$, "As needed", associated with a fifth color $24^5$ which is purple $22^5$.

Commonly used color models are RGB (Red, Green, Blue), CMYK (Cyan, Magenta, Yellow, Black), and HSV (Hue, Saturation, Value). Any color model may be used, however, a YOGB (Yellow, Orange, Green, Blue, Purple) model is illustrated in the periodic daily event color-code sheet 20 for its simplicity and familiarity. The YOGBP color model is an additive color model in which another color may be added to the periodic daily event color-code sheet 20 depending on the number of periodic daily events at which time the specific patient is to be administered the actual medicine product 180 prescribed by his/her medical practitioner to reproduce a broad array of colors for implementation in the medical management chart 100 and the actual medicine product daily organizer 400.

The main purpose of the YOGBP color model implemented with the medicine management and identification system 10 is for the ease of sensing, remembering, representation, and display of images, and viewing text in the medicine management chart 100, an image of the medicine management chart captured by the mobile communications device 500, an application of the medicine management and identification system on a computing system.

A plurality of medicine exemplar containers 30 are implemented with the medicine management chart 100 and the one or more drawers 260 within the medicine management cabinet 200. The medicine exemplar containers 260 are used to contain therewithin an exemplar 182 of an actual medicine product 180 of one of the multiple actual medicine products 180 prescribed in the medicine regimen for the specific patient. The medicine exemplar container 260 is removably attached to the medicine management chart 100 and to the drawers 260 within the medicine management cabinet 200 via an attachment means providing a visual display or exemplars 182 of actual medicine products 180 such that the user, patient, caregiver, or medical practitioner can correctly identify the actual medicine product 180 to be administered to the specific patient at the correct periodic daily event of the day $22^{1-5}$.

Referring to FIGS. 7A-7C, 8A-8C, and 9A-9B the medicine exemplar container 30 is made of a transparent material for facilitating a visual correlation of the exemplar 182 contained therewithin each of the medicine exemplar containers 30 to the actual medicine product 180 the exemplar 182 exemplifies that is to be administered to the specific patient as indicated by associated information 184 displayed on the medicine management chart 100, the medicine management chart 100, described in more detail, below.

In an exemplary embodiment of the disclosure, the medicine exemplar container 30 is manufactured with a non-colored transparent material. In another embodiment of the medicine exemplar container 30 the transparent body 32 is manufactured with a transparent material that includes a clear color tint corresponding to the color $24^{1-5}$ indicative of the periodic daily event of the day $22^{1-5}$ that the color 24 is identified with as depicted on the periodic daily color code sheet 20 and, accordingly, depicted on the medicine management chart 100.

The medicine exemplar containers 30 are provided in a variety of shapes. As shown in FIGS. 7A-7C one or more of the medicine exemplar containers 30 of the plurality of medicine exemplar containers 30 are provided in a circular shape. As shown in FIGS. 8A-8C; and 9A-9B one or more of the medicine exemplar containers 30 of the plurality of medicine exemplar containers 30 are provided in a rectangular shape.

The medicine exemplar container 30 of the plurality of medicine exemplar containers 30 includes a transparent body 32 defining an interior cavity 34 and a transparent sealing cap 36 is adapted and operative to be read therethrough, the transparent sealing cap 36 is adapted for releasably sealing to the transparent body 32 via a sealing means 39 for enabling selectively receiving, containing and removing of the exemplar 182 identifying the actual medicine product 180 therewithin each of the medicine exemplar containers 30.

Figure 18B:
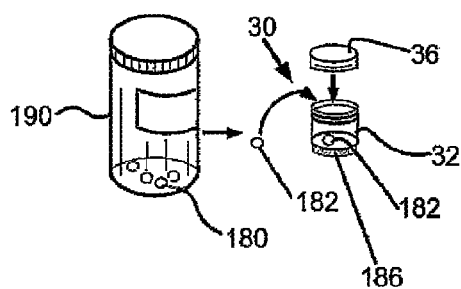
FIG. 18B is a perspective view of an actual medicine product container in use with a medicine exemplar container for use with the medicine management chart of FIG. 18A, according to an embodiment of the disclosure.
Figure 18C:
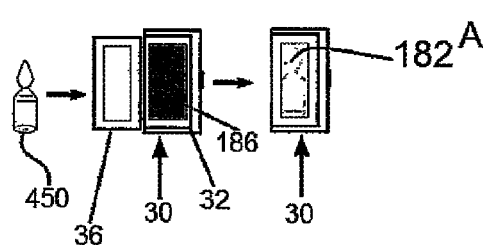
FIG. 18C is a perspective view of an ampule in use with a medicine exemplar container for use with the medicine management chart of FIG. 18A, according to an embodiment of the disclosure.
Figure 19:
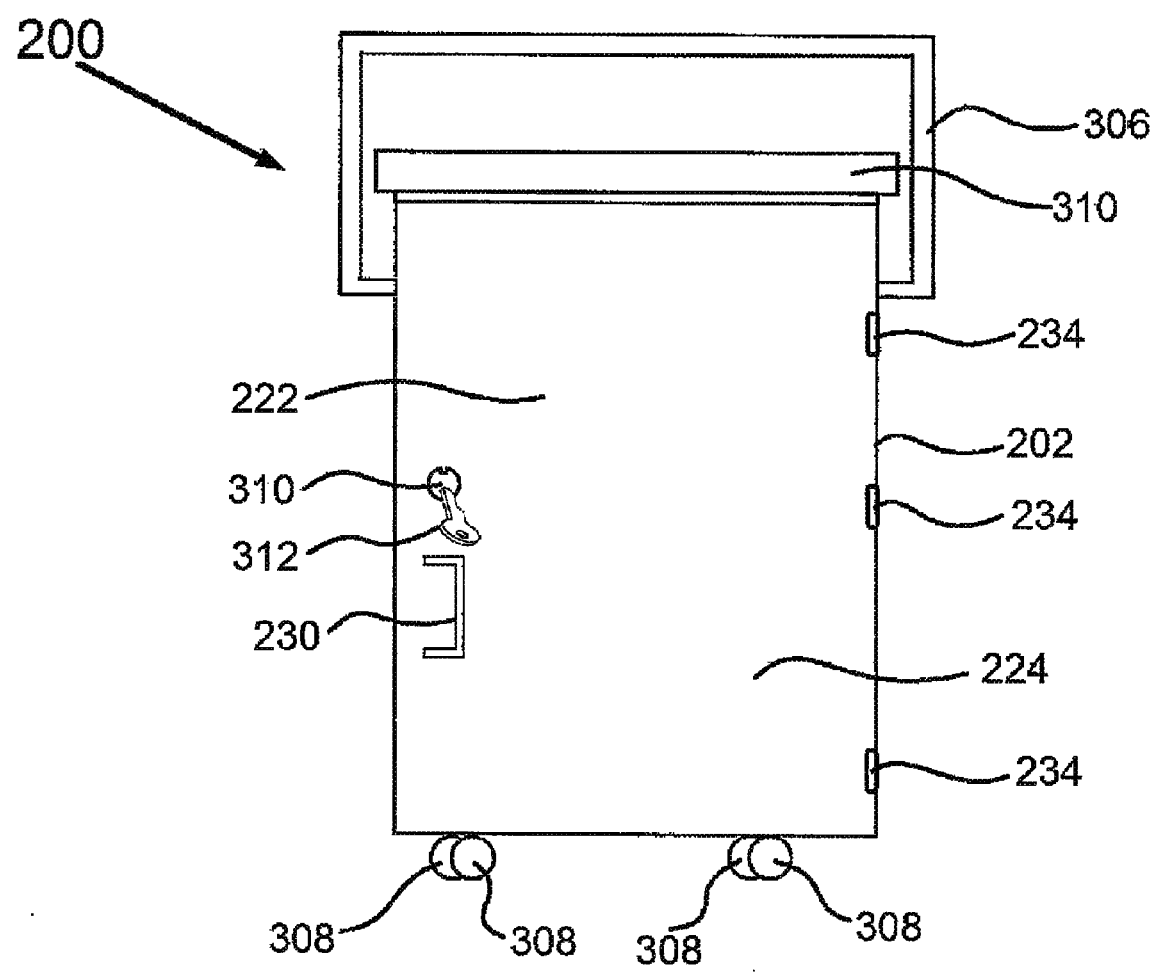
FIG. 19 is a front planar view of a medicine management cabinet, according to an embodiment of the disclosure.
Figure 20:
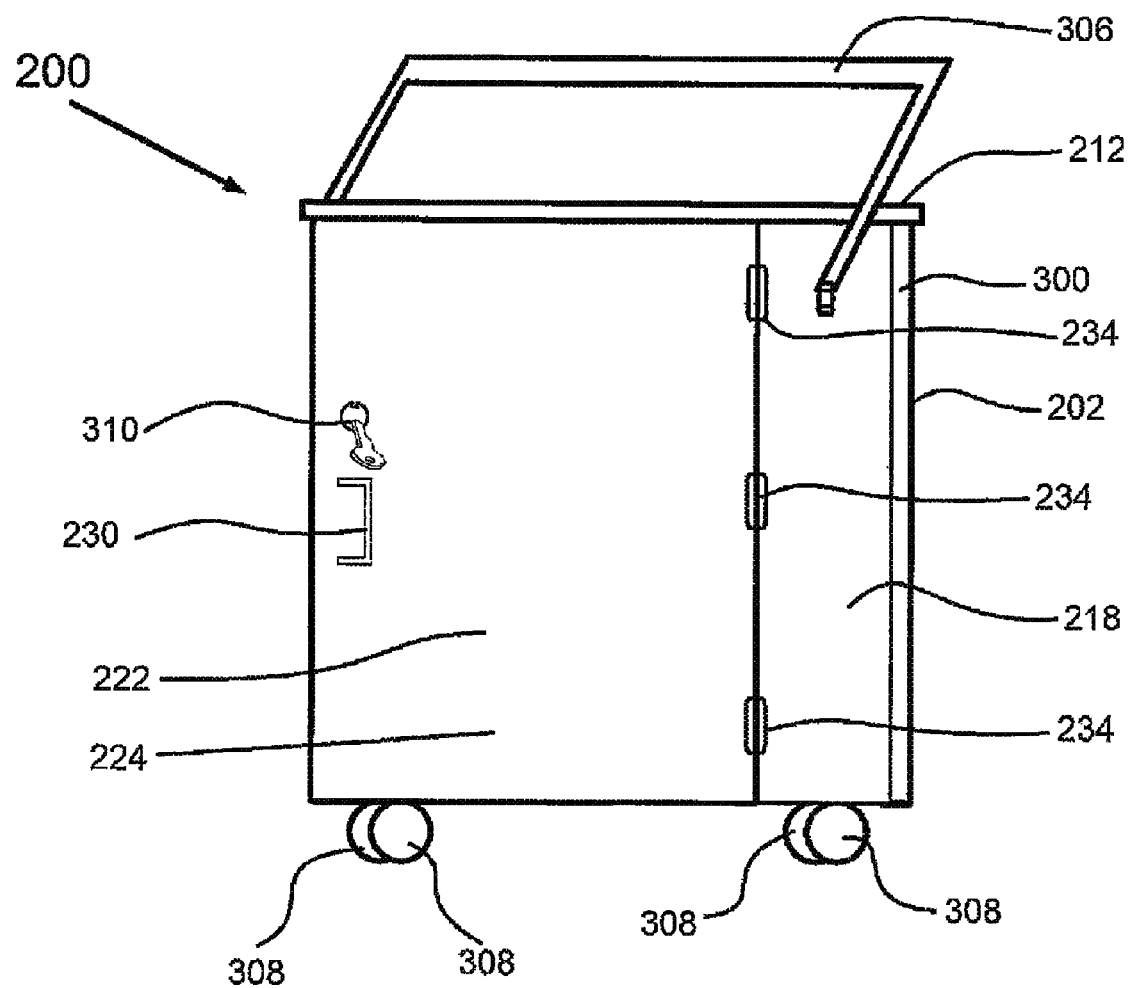
FIG. 20 is a side perspective view of the of a medicine management cabinet of FIG. 19, according to an embodiment of the disclosure.

The transparent sealable cap 36 is releasably sealable to the transparent body 32 to facilitate access to the interior cavity 34 of the medicine exemplar container 30 so that the user, patient, care giver, and/or medical practitioner can fill the medicine exemplar container 30, as shown in FIGS. 18A-18C, refill the medicine exemplar container 30, and empty the medicine exemplar container 30 when needed. For example, when the medicine regimen for the specific patient is changed or when an actual medicine product 180 is no longer prescribed for the specific patient the user, patient, caregiver, or medical practitioner can readily unseal the transparent sealable cap 36 from the transparent body 32 of the medicine exemplar container 30 and remove the exemplar 182 from therewithin the transparent body 32 and discard the now expired exemplar 182 or replace the expired exemplar with a new exemplar 182 of a newly prescribed actual medicine product 180 for the specific patient.

In one scenario the patient, care giver, family member, or medical clinician can place one exemplar 182 in the medicine exemplar container 30 and be able to remove the exemplar 182 when the actual medicine product 180 is no longer prescribed to the particular patient, or if the dosage of the actual medicine product 180 has changed and/or the patient, caregiver, family member, medical clinician needs to decrease or increase the amount of dosage of the actual medicine product 180 as prescribed in the specific patient's medicine regimen.

In an embodiment of the disclosure, the medicine exemplar container 30 is sized and shaped having the transparent body 32 having a circular shape including an interior cavity 34 dimensioned to contain one exemplar 182 of the plurality of actual medicine products 180 of the specific patient's medicine regimen. The depth of the interior cavity 34 is configured having a diameter and depth to receive the size of the exemplar 182 and allow for complete closure of the transparent sealing cap 36 having a mateable circular shape releasably sealed to the transparent body 32 of the medicine exemplar container 30.

As shown in FIGS. 7A-7C, the transparent body 32 of the medicine exemplar container 30 can include a sealing means including a threaded annular lip 33 that is rotatably engaged to a mateable threaded transparent sealing cap 36. As shown in FIGS. 8A-8C the transparent body 32 of the medicine exemplar container 30 wherein the sealing means for releasably sealing the transparent sealing cap 36 to the transparent body 32 of the medicine exemplar container 30 comprises one or more of the following: a threaded opening mechanism, a snap fit mechanism, a ferromagnetic mechanism, a hinge mechanism. The sealing means for releasably attaching the transparent sealing cap 36 to the transparent body 32 of the medicine exemplar container 30 can include any one of the following: a threaded opening mechanism 33 as shown in FIGS. 7A-7B, a hinge mechanism with snap lock 39, as shown in FIGS. 8A-8C and FIGS. 9A-9B, a snap fit mechanism (not shown), a ferromagnetic mechanism (not shown).

Those skilled in the art, in light of the present teachings, will recognize that the shape of the medicine exemplar container 30 can include any one of known geometric shapes including, circles, ovals, rectangles, triangles, trapezoid, or custom shapes to accommodate a variety of shapes and forms of actual medicine products prescribed for a particular patient.

The transparent body 32 includes the attachment means, one mateable mounting magnets 186 of a plurality of mateable mounting magnets 186 attached thereon an exterior flat base portion 38 of the transparent body 32 adapted and operable for removably attaching the medicine exemplar container 30 thereon the medicine management chart 100 when in use with the portable rigid magnetic board 40 and thereon a drawer 260 including a mateable mounting magnet 186 of the plurality of mateable mounting magnets 186, of the medicine management cabinet 200.

In the exemplary embodiment, the exterior flat base portion 38 of the transparent body 36 of the medicine exemplar container 30 can include a peelable adhesive membrane to adhere the mateable mounting magnet 186 thereon so that the medicine exemplar container 30 can be removably attached within each of the Prescriptions/Supplement tiles $128^{1-5}$, described in more detail below, of the medicine management chart 100 and to a drawer 260 within the medicine management cabinet 200.

The medicine exemplar container 30 is removably attached to the medicine manager chart 200 such that the medicine exemplar container 30 transparent sealing cap 36 is facing forward to the user, patient, care giver, and/or medical practitioner to facilitate visual viewing of the exemplar 182 of the actual medicine product 180 contained therewithin. Accordingly, the medicine exemplar container 30 is removably attached to the drawer 260 within the medicine management cabinet 200 such that the medicine exemplar container 30 transparent sealing cap 36 is facing forward to the user, patient, care giver, and/or medical practitioner to facilitate visual viewing of the exemplar 182 of the actual medicine product 180 contained therewithin.

In an exemplary embodiment, as shown in FIGS. 2-6 the medicine exemplar container 30 includes the transparent body 32 having a size and shape including the interior cavity 34 dimensioned to contain one exemplar 182 of the actual medicine product 180 and operable to removably attach within the Medicine/Supplement Exemplar tiles $126^{1-5}$ of the medicine management chart 100. The depth of the interior cavity 34 of the transparent body 32 is configured having a diameter and depth to receive the one exemplar 182 of the actual medicine product 180 of the plurality of actual medicine products 180 prescribed and allow for complete closure of the transparent sealing cap 36 releasably sealed via a sealing means 39 to the transparent body 32 of the medicine exemplar container 30.

In an embodiment of the disclosure, the transparent sealing cap 36 of the medicine exemplar container 30 further includes a peripheral rim 37, as shown in FIGS. 7A-7B.

The peripheral rim 37 is completely shaded in one of the colors $24^1$-$24^5$ preselected from the variety of different colors $24^1$-$24^5$ for enabling for visually correlating the color 24 with the corresponding periodic daily event 22 of the day of the number of different daily events of the day $22^1$-$22^5$, as depicted on periodic daily event color-code sheet 20 to visually identify at which time of the day the specific patient is to be administered one or more of a multiple of actual medicine products 180 of the medicine regimen for the specific patient. The color 24 of the variety of different colors $24^1$-$24^5$ include any one of the different colors $24^1$-$24^5$ as indicated by the periodic daily event color-code sheet 20 in the instructions 26: the first color $24^1$, yellow $24^1$, corresponds with the first periodic daily event of the day, Breakfast $22^1$; the second color $24^2$, orange $24^1$, corresponds to the second periodic daily event of the day $22^2$, Lunch $22^2$; the third color $24^3$, green, corresponds to the third periodic daily event of the day $22^3$, Dinner $22^3$; the fourth color $24^4$, blue $24^4$ corresponds to the fourth periodic daily event of the day $22^4$, Bedtime $22^4$; the fifth color $24^5$, purple $24^5$ corresponds to the fifth periodic daily event of the day $22^5$, As Needed $22^5$, for enabling for visually advising of the proper removable attachment of any one or more of the medicine exemplar containers 30 including a peripheral rim 37 completely color shaded in the color $24^{1-4}$ each to a corresponding Medicine/Supplements Exemplar tile $128^{1-5}$ within each of a periodic daily event matrix of tiles 106 completely shaded in the same color 24 within the medicine manager chart 100, and the corresponding drawer 260 having the same color 24 within the medicine management cabinet 200, and the corresponding row 414 of color shaded cubicles 406 completely shaded in the same color 24 within the actual medicine product daily organizer 400.

In an exemplary embodiment, the medicine exemplary container 30, the transparent body 32, and the transparent sealing cap 36 are manufactured with a non-color shaded transparent material. In another embodiment, the medicine exemplar container 30, the transparent body 32, and the transparent sealing cap 36 will remain clear so that the user can readily read therethrough, the transparent sealing cap 36.

In one embodiment of the present disclosure, the transparent body 32 is manufactured with a color shaded transparent material that includes the colors $24^{1-5}$ corresponding to the preselected colors $24^{1-5}$ of the periodic daily event of the day $22^{1-5}$ as identified on the periodic daily event color-code sheet 20, as identified above, for use with the medicine management chart 100 and the medicine management cabinet 200, and the actual medicine product daily organizer 400.

In use, the medicine exemplar container 30 includes a mateable mounting magnet 186 attached to the exterior flat base portion 38 of the transparent body 32 for enabling removably attaching the medicine exemplar container 30 to the medicine management chart when displayed against the portable rigid magnetic board 40. The transparent body 32 of the medicine exemplar container 30 can include any one of the colors $24^{1-5}$ associated with the periodic daily event color-code sheet 20 so as to visually correlate the medicine exemplar container 30 with a corresponding periodic daily event $22^{1-5}$ identified in the periodic daily event color-code sheet 20. Accordingly, the medicine exemplar container 30 having a color shaded transparent body 32 completely shaded with one of the variety of different colors $24^{1-5}$ is removably attached within the periodic daily event matrix of tiles of the same one color 24 of the variety of different colors $24^{1-5}$ and a remotely located medicine exemplary container 30 of the same one color of the variety of different colors $24^{1-5}$ can be removably attached to the drawer 260 of the same one color 24 of the variety of different colors $24^{1-5}$ within the medicine management cabinet 200.

In the exemplary embodiment it is preferred that the transparent sealing cap 36 is a colorless translucent material for facilitating visual observation of the contained exemplar 182 of the actual medicine product, for example, a pill, liquid medicine, or supplement, vitamin, ampule $182^4$, contained therewithin.

The transparent sealing cap 36 is adapted for releasable sealing to the transparent body 32 to enable opening the medicine exemplar container 30 to selectively open and close the medicine exemplar container 30 so that the user, patient, care giver, medical practitioner can keep the medicine management chart 100 current with the current medicine regimen of the specific patient and, accordingly, keep current the associated information 184 corresponding to the actual medicine product 180. In one scenario the patient, care giver, or medical clinician can place the exemplar 182 into the medicine exemplar container 30 and be able to remove the exemplar 182 when the actual medicine product 182 is no longer prescribed to the specific patient, or when a new actual medicine product 182 is prescribed in the medicine regimen for the specific patient.

In an embodiment of the disclosure, the medicine exemplar container 30 may include a hook and loop element on the exterior flat base portion 38 of the medicine exemplar container 30 to removably attach the medicine exemplar container 30 on a mateable hook and loop Medicine/Supplement Exemplar tile $126^{1-5}$ on the medicine management chart 100. Accordingly, the raised front wall 276 of each of the drawers 260 may include the mateable hook and loop to removably and/or movably attach the medicine exemplar container 30.

In another embodiment of the disclosure, the exterior flat base portion 38 of the medicine exemplar container 30 may include a peelable adhesive to removably attach the medicine exemplar container 30 onto the medicine management chart 100 and remotely positioned on the drawers 260 within the medicine management cabinet 200.

In an embodiment of the disclosure the medicine exemplar container 30 can include a perforated transparent sealing cap 189 including perforations 188 (not shown) for enabling transmission of ambient air from an external environment into the interior cavity 34 of the transparent body 32 of the medicine exemplar container 30.

It is important to note before a new exemplar 182 is placed in the medicine exemplar container 30, a current image 524 of the medicine management chart 100, now the prior medicine management chart 100 can be taken by the user, patient, caregiver, medical practitioner, with a mobile communications device 500, including a preinstalled camera 502, as described in more detail below. The mobile communications device 500 can store and archive the image 524 of the prior medicine management chart 100, and any consecutive prior medicine management charts 100 within the mobile communications device's 500 computing devices as a pre-stored record for the specific patient to be able to detect relative changes in medications against the patient's current health condition. In addition, the mobile communications device 500 can include a USB flash drive 504 for storing the images 524.

In addition, an image 524 of the specific patient is taken by the caregiver, family member, patient (selfie), medical practitioner, and printed. The printed image 524 of the specific patient can be placed in the medicine management notebook 600 along with the corresponding medicine management chart 100 of a specific date and time so that the user, patient, caregiver, medical practitioner can visually see the progress or deterioration of the specific patient during the medicine regimen depicted on the image 524 of the medicine management chart 100.

Those skilled in the art, in light of the present teachings, may recognize that the medicine exemplar container 30 may include a plurality of shapes and dimensions to accommodate a multiple number of exemplars 182 of actual medicine products 182 prescribed to the specific patient. The medicine exemplar container 30 can include a rectangular shape, square shape, oval shape, and a shape conforming to the particular physical properties of the exemplar 182 of the actual medicine product 180.

As known, the actual medicine product 180 can be any type of actual medicine product 180, including, but not limited to, pills, pills in gel form, liquid medicine in ampules $182^A$, drops, ointments, saves, patches, needles, powders, oils, and vitamins. The actual medicine product 180 may have one or more different shapes so it is an objective of the exemplary embodiment of the disclosure to provide a medicine exemplar container 30 in various shapes for enabling the containment of the exemplar of the actual medicine product 180 therewithin.

As shown in FIGS. 9A-9B, the medicine exemplar container 30 can be adapted for containing an exemplar 182 of an ampule $182^A$ such that the ampule exemplar $182^A$ is placed in the transparent body 32 of the medicine exemplar container 30 configured to receive the ampule exemplar $182^A$ and a transparent sealing cap 36 configured to releasably attach to the medicine exemplar container 30 for enabling for the selective opening and closing of the medicine exemplar container 30.

As shown in FIGS. 2, 3, 4, 5A-5E, and FIG. 6, the medicine manager chart 100 of the one or more of the medicine manager charts 100 provides a personalizable display of the embodiments of the present disclosure identifying actual medicine products 180 and identifying associated information 184 of a plurality of actual medicine products 180 prescribed in a medicine regimen for a specific patient, exemplars 30 of which are each contained therewithin the medicine exemplar containers 30 removably attached to the medicine manager chart 100 to be administered at a periodic daily event of a day $22^{1-5}$ to the specific patient. The medicine management chart 100, also, provides identification of the specific patient by means of a patient identification tile 104 and the specific patient's medical practitioner is identified in a medical practitioner tile 102, as described in more detail below, The medicine manager chart 100 allows the user to visually correctly identify and correctly correlate the exemplar 180 with associated information 184 about the actual medicine product 180 the exemplar 30 corresponds to, so as to visually facilitate a correlation of the actual medicine product 180 with the associated information 184 and allow for the correct management of the actual medicine product 180 to be administered to the specific patient at the correct periodic daily event 22 of the day. In addition, the periodic daily events $22^{1-5}$ of the day preprinted on the medicine management chart 100 at which time the actual medicine product 180 is to be dispensed to the specific patient is coded with the color 24 of the variety of different colors $24^{1-5}$, as ascertained from the periodic daily event color-code sheet 20 to facilitate the user's, patient's, caregiver's, and/or medical practitioner's association with the periodic daily event 22 of the day at which time the specific patient is to be administered the actual medicine product 180 with the corresponding preselected color 24.

The medicine manager chart 100 may be completed by the user, patient, caregiver, or the medical practitioner for use by the user, patient, caregiver, or the medical practitioner. A plurality of medicine manager charts 100 are provided with a variety of pre-selected periodic daily events $22^{1-5}$ of the day so as to allow the user to customize the implementation of the medicine management and identification system 10 for a specific patient having a prescribed medicine regimen including the preselected periodic daily events $22^{1-5}$.

Figure 3:
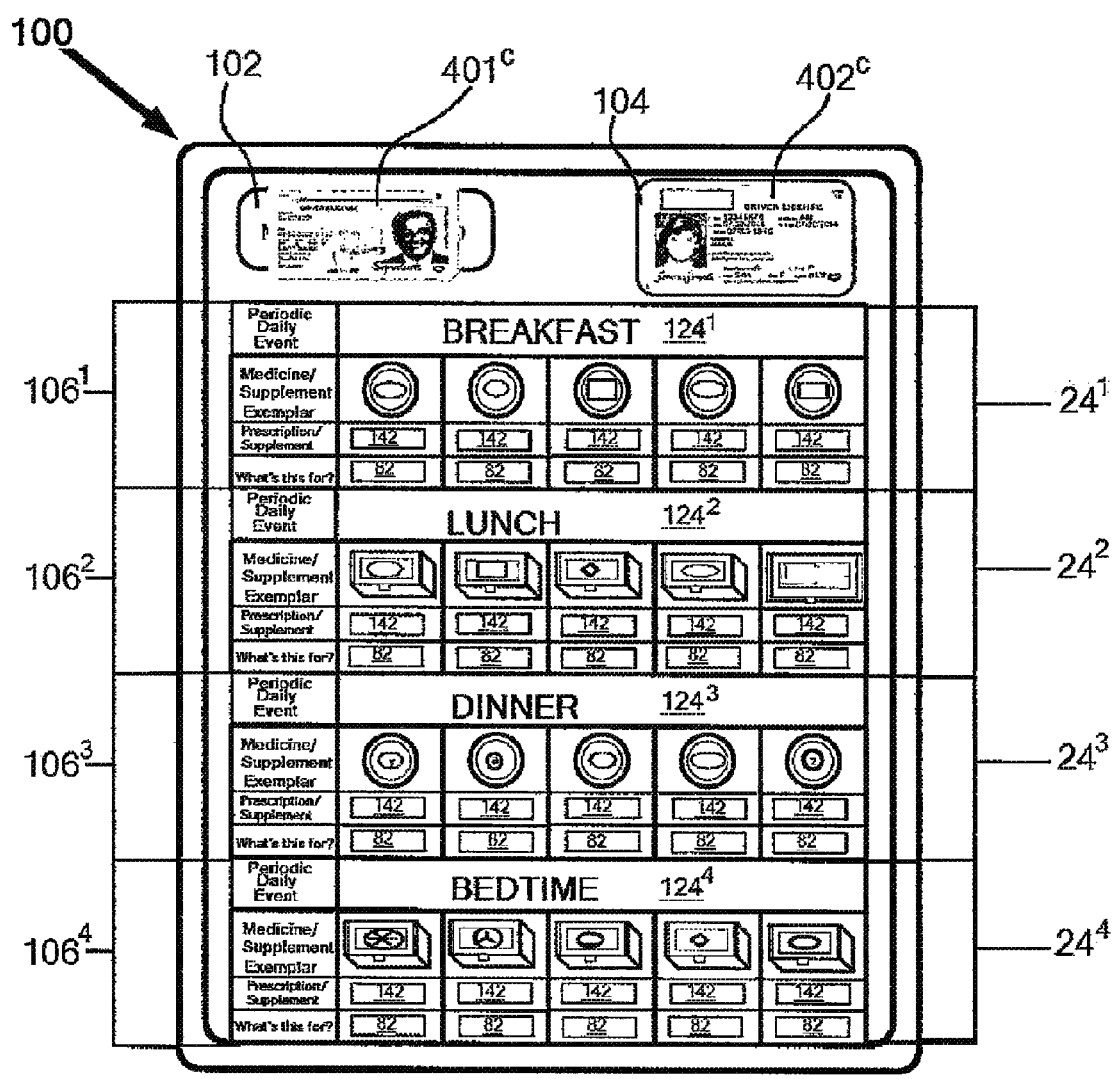
FIG. 3 is a front planar view of a medicine management chart, according to an embodiment of the disclosure.
Figure 4:
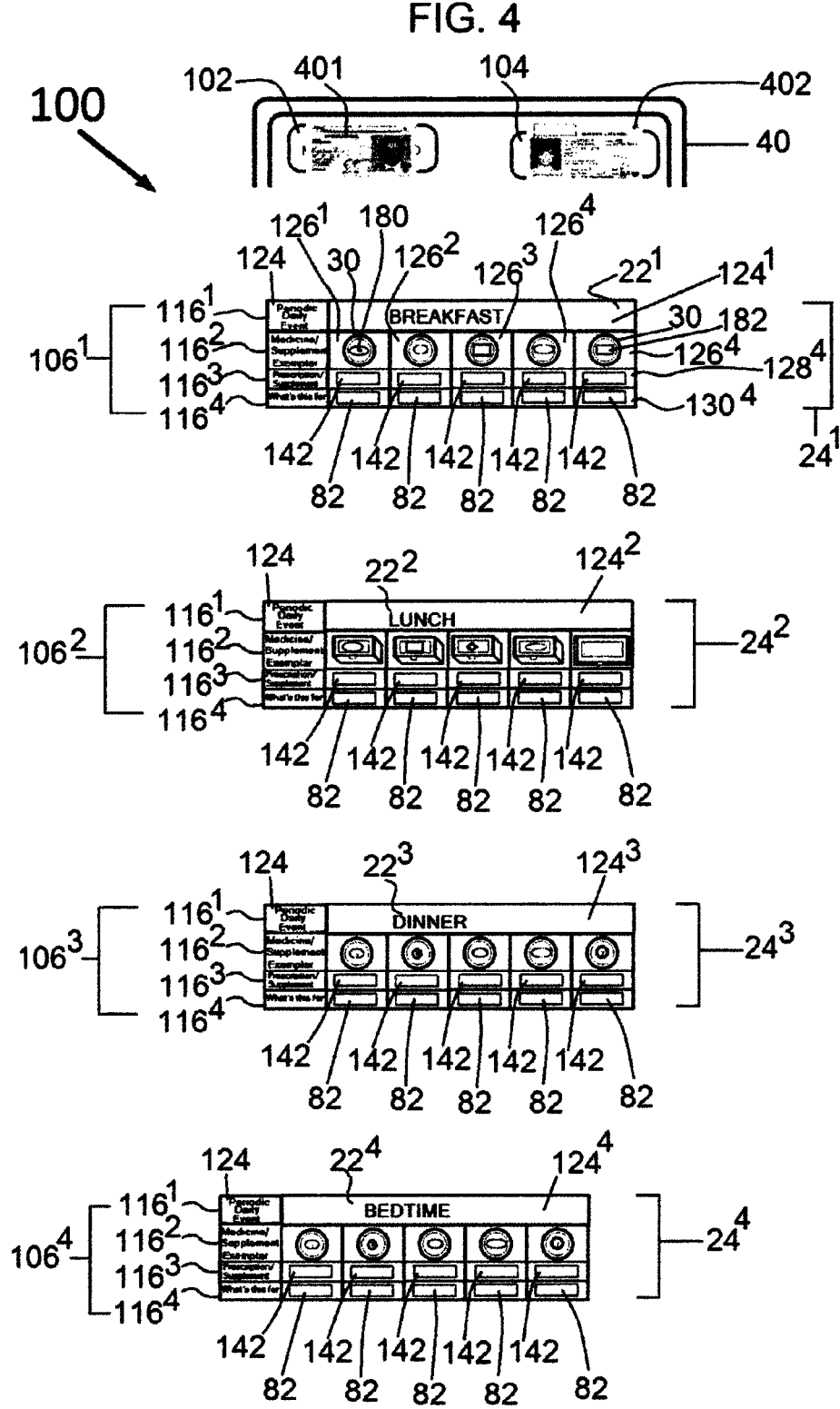
FIG. 4 is an exploded front perspective view of the medical management chart of FIG. 3, according to an embodiment of the disclosure.

As shown in FIGS. 3-4, the medicine identification chart 100 of the embodiments of the disclosure are implemented for identifying a specific patient identified in a patient identification tile 104, for identifying a medical practitioner in a medical practitioner tile 102 associated with the specific patient identified in a patient identification tile 104, for identifying actual medicine products 180 ascertained by the exemplars 30 contained therewithin each of the medicine exemplar containers 30, and indicating associated information 184 so as to visually correctly identify and correctly correlate the exemplar 30 with associated information 184 about the actual medicine product 180 the exemplar 30 corresponds to, so as to visually facilitate a correlation of the actual medicine product 180 with the associated information 184 and allow for the correct management and identification of the actual medicine product 180 to be administered to the specific patient at the correct periodic daily event of the day 22.

In an exemplary embodiment the medicine manager chart 100 is manufactured from a malleable material. The malleable material can be any one of the following malleable materials, paper, silicone, fiber glass with silicone, plastic film. The medicine manager chart 100 is implemented with the provision of the portable rigid magnetic board 40 positioned behind the medicine manager chart 100 such that the plurality of transparent medicine exemplar containers 30 removably attached thereon the medicine manager chart 100 and the plurality of periodic daily event matrices of tiles $106^{1-5}$ displaying the associated information 184 are operating thereon the front side 108 of the medicine manager chart 100.

Accordingly, one or more of the medicine exemplar containers 30 are removably attached to the front side 108 of the medicine manager chart 100 via a mateable mounting magnet 186 of a plurality of mateable mounting magnets 186, which are attracted to the portable rigid magnetic board 40.

The portable rigid magnetic board 40 can include a supporting means 42 to support the portable rigid magnetic board 40 in use with the medicine manager chart 100 removably attached thereon for facilitating the display of the medicine manager chart 100 to a user, patient, care giver, and/or medical practitioner. In an exemplary embodiment of the present invention the medicine manager chart 100 releasably attached to the portable rigid magnetic board 40 in combination is supported by the supporting means 50, the mounting platform 50, as shown in FIGS. 15A-15B, FIGS. 16A-16B, 17, 18A, 21, and 22, as described in more detail above. In another embodiment, the portable rigid magnetic board 100 includes a stand that enables the portable rigid magnetic board 40 to stand alone without the mounting platform 50. In another embodiment the portable rigid magnetic board 100 can be displayed on top of the medicine management cabinet 200.

The configuration of the medicine manager chart 100 can be best seen in FIGS. 2-5A-5E. In the exemplary embodiment of the disclosure, the medicine manager chart 100 has the front side 108 and an underside side 110. The medicine manager chart 100 is implemented for use in combination with the portable rigid magnetic board 40 and with the plurality of medicine exemplar containers 30 wherein each of the transparent medicine exemplar container 30 of the plurality of transparent exemplar containers 30 includes one of the plurality of the mateable mounting magnetics 186 attached to the flat base portion 38 of the transparent body 32, wherewith the mateable mounting magnet is attracted to the portable rigid magnetic board 40.

Each of the medicine manager charts 100 of the plurality of medicine manager charts 100 includes associated information 184 corresponding to each of the one or more of the multiple actual medicine products 180 of the specific patient's medicine regimen as exemplified by the exemplar 182 therewithin each of the medicine exemplar containers 30.

The medicine management chart 100 includes a plurality of the periodic daily event matrices of tiles $106^{1-5}$ preprinted upon the front side 108 of the medicine manager chart 100. Each of a periodic daily event matrix of tiles 106 of the plurality of periodic daily event matrices of tiles $106^{1-5}$ is completely color shaded with a different color 24 of the variety of different colors $24^{1-5}$ ascertained from the periodic daily event color-code sheet 20, bearing the viewing text of the periodic daily events $22^{1-5}$ preprinted thereon, headers $112^{1-5}$ preprinted thereon, daily event headers $124^{1-5}$ preprinted thereon, and bearing the associated information 184 of each of the exemplars 182 of the actual medicine products 180.

More particularly, the medicine manager chart 100 includes a malleable substrate generally having a rectangular shape having the front side 108 and the underside 110. The front side 108 includes a preprinted sheet depicting one or more identification tiles 102 and 104, and one or more vertical columns 114 and one or more horizontal rows 116 intersecting to form a plurality of periodic daily event matrices of tiles $106^{1-5}$ and including one or more periodic daily event matrix of tiles 106 of the plurality of periodic daily event matrices of tiles 106 arrayed in a chronological arrangement.

The medicine manager chart 100 is removably attached to the portable rigid magnetic board 40 by means of one or more of the plurality of medicine exemplar containers 30 having the mateable mounting means 186 attached thereon so that the medicine manager chart 100 assembles visually and operatively against the portable rigid magnetic board 40. Each of the transparent medicine exemplar containers 30 includes the mateable mounting magnets 186 of the plurality of mateable mounting magnets 186 attached thereon for enabling for the removable attachment of the medicine manager chart 100 to the portable rigid magnetic board 40. The underside 110 of the medicine manager chart 100 is a blank sheet.

Figure 2:
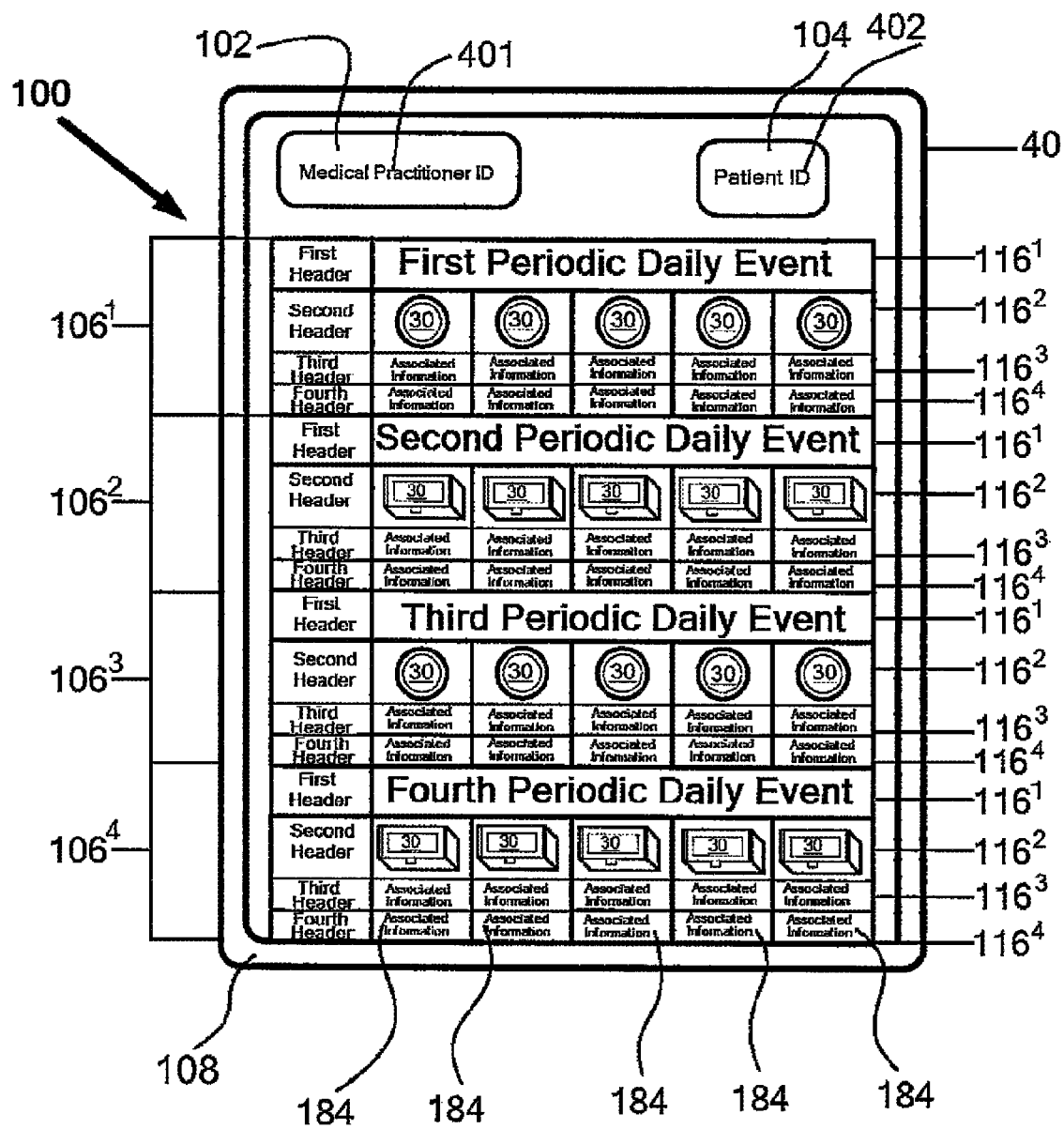
FIG. 2 is a front planar view of a medicine management chart, according to an embodiment of the disclosure.

Referring to FIGS. 2 and 3, a first of the one or more of the identification tiles 102 and 104, includes a medical practitioner identification tile 102 arranged horizontally a distance apart from a second of the one or more of the identification tiles 102 and 104, a patient identification tile 104. The medical practitioner identification tile 102 includes a preprinted viewing text[1], "Medical Practitioner ID" 401, preprinted thereon, and the patient identification tile 104 includes a preprinted viewing text[2], "Patient ID" 402, preprinted thereon.

The medical practitioner identification tile 102 includes an area[1] for removably attaching a medical practitioner identification card $401^C$. The medical practitioner identification card $401^C$ includes a mateable mounting magnets 186 of the plurality of mateable mounting magnets 186 for removably attaching the medical practitioner identification card $401^C$ thereon the medical practitioner identification tile 102. The medical practitioner identification tile 102 is configured to receive an identification card or business card of the medical practitioner associated with the specific patient and from whom the actual medicine products 180 are prescribed. The medical practitioner identification card $401^C$ can include the identification card of the medical practitioner, for example, driver's license, picture id, picture, the name of the medical practitioner and/or care giver, contact information, address, telephone emergency numbers, e-mail, and prescriptive information regarding the medical practitioner and/or care giver.

A second of the one or more of the identification tiles 102 and 104 includes the patient identification tile 104 for a specific patient associated with the implementation of the medicine management and identification system 10 and with the indicated medical practitioner identified by the medical practitioner identification card $401^C$, wherein the patient identification tile 104 includes an $area^2$ for removably attaching the patient identification card $402^C$ thereon. The patient identification card $402^C$ includes a mateable mounting magnet 186 of one of the plurality of mateable mounting magnets 186 for removably attaching the patient identification card $402^C$ thereon the patient identification tile 104. The patient identification tile 104 is configured to receive the patient identification card $402^C$ of the specific patient associated with the implemented medical management and identification system 10.

The patient identification card 120 can include the identification card of the patient, for example, driver's license, picture id, picture, a picture of the patient, the patient's date of birth, telephone number, e-mail, emergency contact information, and the like.

In an embodiment of the disclosure, a picture identification of the caregiver can be removably attached to the medicine management chart 100 positioned between medical practitioner identification card $401^C$ and the patient identification card $402^C$.

Immediately below, the Medical Practitioner Identification tile 102 and the Patient Identification tile 104 are the one or more of the periodic daily event matrices of tiles $106^{1-5}$ arranged in the chronological arrangement as depicted on the periodic daily event color-code sheet 20. In the exemplary embodiment shown in FIGS. 3-5E four periodic daily event matrices of tiles $106^{1-4}$ of the five periodic daily event matrices of tiles $106^{1-5}$ of the periodic daily event matrices of tiles 106 are shown. Each of the periodic matrix of tiles 106 is completely shaded in the color 24 of the variety of different colors $24^{1-5}$ bearing the corresponding periodic daily event 22 of the day preprinted thereon so as to visually facilitate the identification of the periodic daily event 22 of the day with the color 24 so as to visually alert the user, patient, caregiver, medical practitioner of the correct periodic daily event $22^{1-5}$ of the day to administer the actual medicine product to the specific patient.

Thereby, each of the periodic daily event matrix of tiles $106^{1-4}$ of the one or more periodic daily event matrices of tiles $106^{1-5}$ completely shaded in the color $24^{1-4}$ and bearing the periodic daily event $22^{1-4}$ of the day printed thereon as depicted in the periodic daily event color code sheet 20 being arrayed according to the time of the day so that each of the periodic daily event matrix of tiles $106^{1-4}$ are disposed in the chronological arrangement ascertained from the periodic daily event color-code sheet 20 preprinted thereon the medicine manager chart 100 is readily cognizable as representing a particular respective time of the day when the specific patient is to be administered a dosage of the actual medicine product 180.

Each periodic daily event matrix of tiles 106 includes rows $116^{1-4}$. Each of the rows $116^{1-4}$ is headed by a header tile 122 each including a header text to describe the associated information 184 included within the tiles of each of the rows $116^{1-4}$. A first header tile $122^1$ includes is a first header text, namely, Periodic Daily Event 124, forming a Periodic Daily Event header tile 124. Further, the first row $116^1$ includes a second tile $124^{1-4}$ horizontally adjacent to the Periodic Daily Event header tile 124, a second tile includes an $area^4$ bearing a preprinted viewing $text^4$ of a periodic daily event $22^{1-n}$ preprinted thereon forming a periodic daily event tile $124^{1-4}$ associated with the preselected color $24^{1-4}$ of the periodic daily event matrix of tiles $106^{1-4}$ as depicted in the periodic daily event color code sheet 20 indicating at which time the specific patient is to be administered a dosage 146 of the actual medicine products 180 cabined in the actual medicine product daily organizer 400.

A second header tile $122^2$ is a second header $112^2$ bearing a preprinted viewing text, Medicine/Supplement Exemplar, forming a Medicine/Supplement Exemplar header tile 126 which heads each of a second row $116^2$ of each of the periodic daily event matrix of tiles $106^{1-4}$. Each of the second rows $116^2$ include one or more of Medicine/Supplement Exemplar tiles $126^{1-5}$ therewithin, wherein each of the Medicine/Supplement Exemplar tiles $126^{1-5}$ includes an $area^4$ for removably attaching one of the plurality of medicine exemplar containers 30 containing an exemplar 182 therewithin of its corresponding actual medicine product 180 so as to visually correctly identify and correlate the actual medicine product 180 to be administered to the specific patient at the associated preselected periodic daily event 22 of the day.

A third header tile $122^3$ is a third header $112^3$ bearing a preprinted viewing text s, Prescriptions/Supplements 128, forming a Prescriptions/Supplements header tile 128 which heads each of a third row $116^3$ of each of the periodic daily event matrix of tiles $106^{1-5}$. Each of the third rows $116^3$ includes one or more of Prescription/Supplements tiles $128^{1-5}$. Each of the one or more of the Prescription/Supplements tiles $128^{1-5}$ is aligned to an adjacent Medicine/Supplement tile $126^{1-5}$ of the second row $116^2$. Each one or more of the Prescription/Supplements tiles $128^{1-5}$ includes an $area^5$ whose associated information 184 is one or more indicators 801 of the actual medicine product 180 identified by the exemplar 182 contained therewithin an adjacent medicine exemplar container 30 removably attached within each of an aligned adjacent Medicine/Supplement tiles $126^{1-5}$ of the second row $116^2$, and a corresponding medicine exemplar container 30 of the plurality of the medicine exemplar containers 30 remotely maintained within the medicine management cabinet 200, as explained in more detail below.

The one or more indicators 801 can include a pharmaceutical identification 804, or a prescription name, or a trade name, or a generic name, of the actual medicine product 180, a dosage 806, a time of administration 808, or adverse reactions 810 of the actual medicine product 180. The indicators 801 can be obtained from the medical practitioner at the time the specific patient is provided with the specific patient's medicine regimen.

Figure 12A:
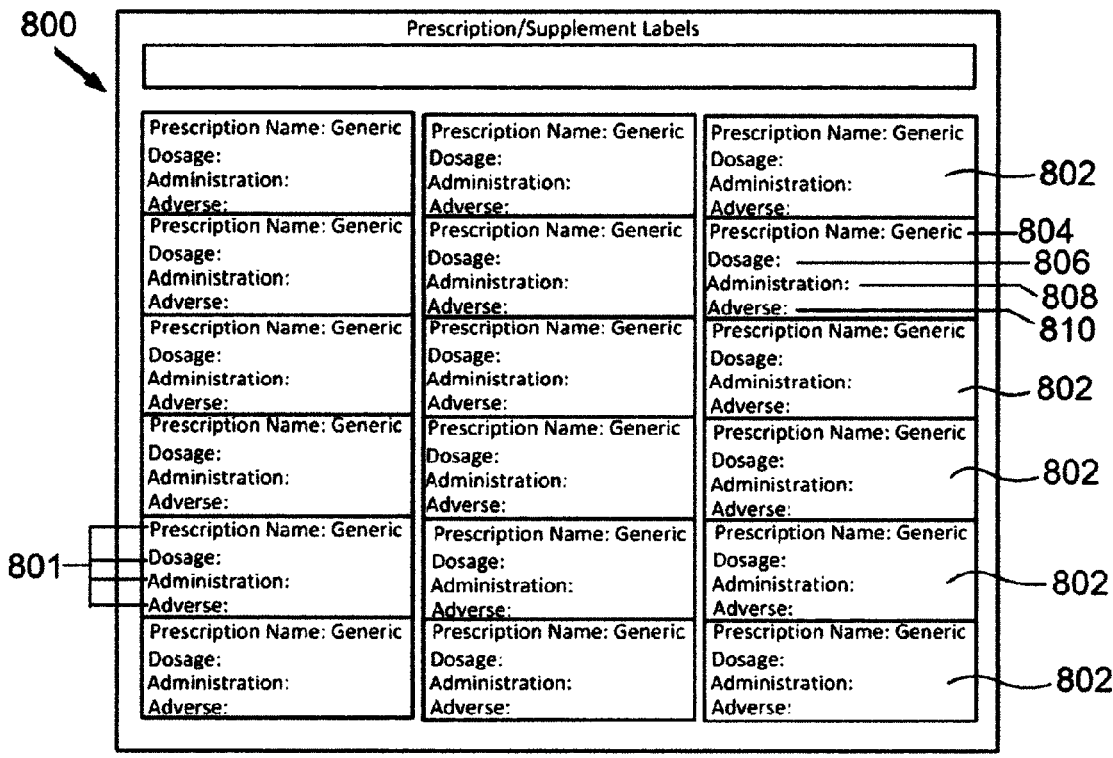
FIG. 12A is a front planar view of a sheet of Prescription/Supplement labels, according to an embodiment of the disclosure.
Figure 12B:
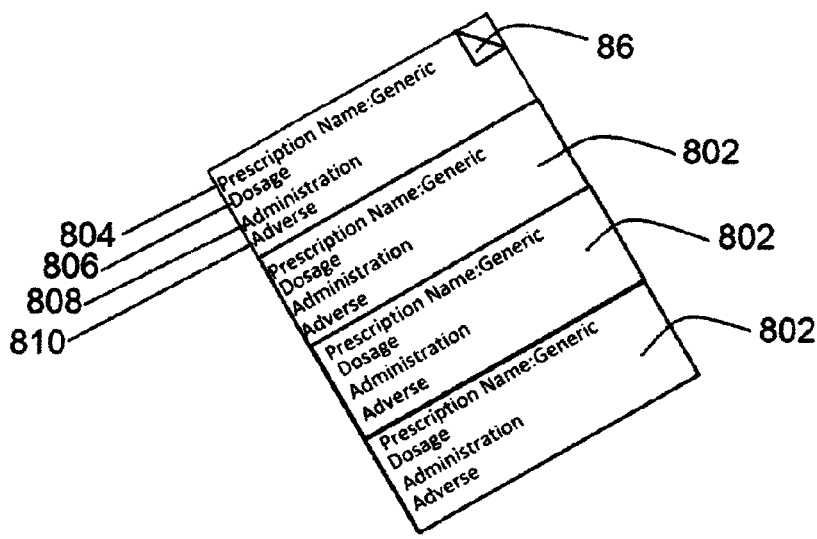
FIG. 12B is a perspective view of a row of Prescription/Supplement labels of FIG. 12A, according to an embodiment of the disclosure.

As shown in FIG. 12A, each of the indicators 140 for a particular actual medicine product 180 can be preprinted thereon a Prescription/Supplements label 802 wherein each Prescription/Supplements label 802 label includes an adhesive back having a peel-off membrane provided in a sheet of preprinted Prescription/Supplements labels 800 for use with the medicine management chart 100. The user, patient, caregiver, medical practitioner can adhere the Prescription/Supplements label 142 to each of the Prescription/Supplements tiles $128^{1-5}$ adjacently aligned to the medicine exemplar container 30 having the exemplar of the actual medicine product 180 contained therewithin and removably attached to the adjacently aligned Medicine/Supplement tile $126^{1-5}$ for enabling to visually correlate and identify the exemplar 182 contained therewithin the medicine exemplar container 30 of actual medicine product 180 with the pharmaceutical identification 804, i.e. a name, a trade name, a generic name, dosage 806, time of administration 808, and adverse reactions 810, of the actual medicine product 180.

The one or more indicators 801 can, further, include any adverse reactions 150 the actual medicine products 180 may notably be characterized therewith other medicine products, food, or alcohol.

Sheets of preprinted Prescription/Supplements labels 800 can be preprinted on commercially available Avery® labels with an adhesive back having a peel-off membrane provided. A user can peel off each of the preprinted Prescription/Supplements Labels 802 which can be adhered to a mateable mounting magnet 186 of the plurality of mateably mounting magnets 186 for enabling for removably attaching the preprinted Prescription/Supplements Labels 802 to each of the Prescriptions/Supplement tiles $128^{1-5}$ of the third row $116^3$ of the corresponding periodic daily event matrix of tiles $106^{1-5}$ aligned with the corresponding medicine exemplar containers 30 removably attached thereon the corresponding aligned Medicine/Supplement Exemplar tile $126^{1-5}$ of the second row $116^2$ within the corresponding periodic daily event matrix of tiles $106^{1-5}$ of the medicine manager chart 100.

A fourth header tile $122^4$ includes a fourth header bearing preprinted viewing text, What's this for? 130 forming a What's this for? header tile 130, heads each of the fourth row $116^4$ of each of the periodic daily event matrix of tiles $106^{1-5}$. The fourth row $116^4$ includes one or more of What's this for? tiles $130^{1-5}$ each aligned to the Medicine/Supplement tiles $126^{1-5}$ of the second row $116^2$, wherein each of the What's this for? tiles $130^{1-5}$ includes an area$^6$ whose associated information 184 is one or more of notable known prescriptive medical reasons 152 for administering of the actual medicine product 180 identified by the exemplar 182 contained therewithin the aligned adjacent medicine exemplar container 30 removably attached in the aligned Medicine/Supplement Exemplar tile 126 of the second row $116^2$, and the corresponding medicine exemplar container 30 remotely maintained within the medicine management cabinet 200 so as to visually correlate and identify the actual medicine product 180 with the prescriptive notable known medical reason 150 for administering of the actual medicine product 180.

Figure 13A:
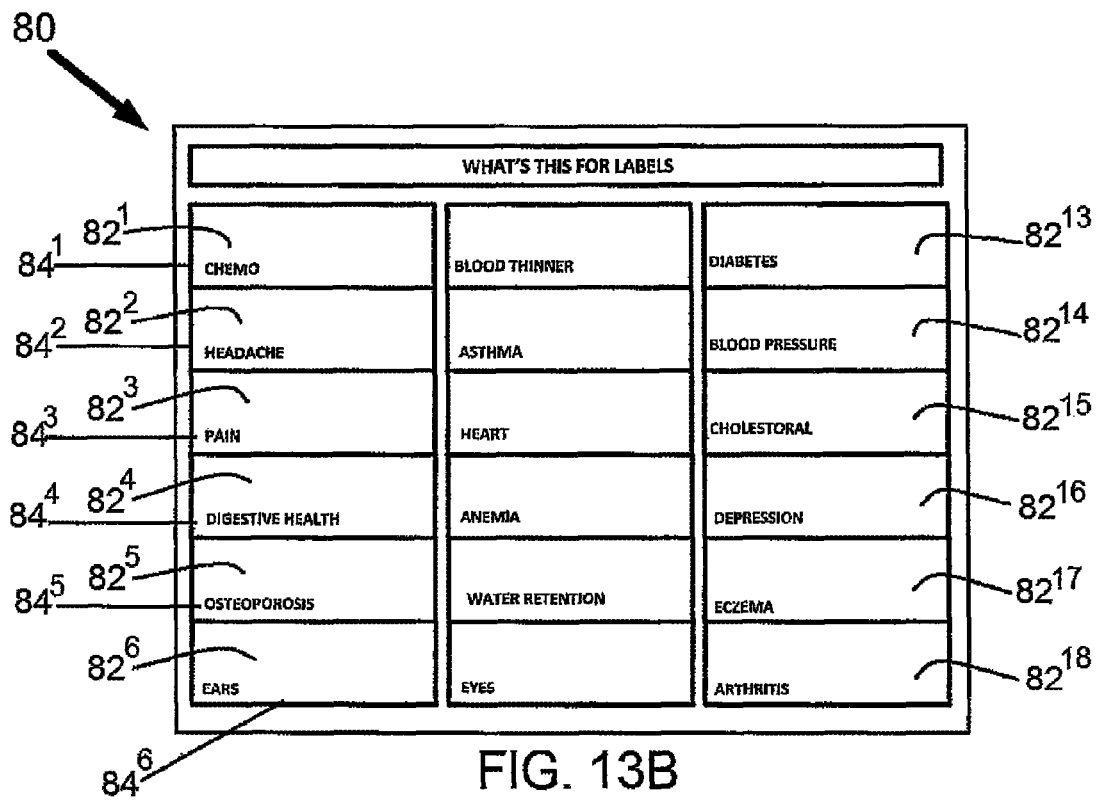
FIG. 13A is a front planar view of a sheet of What's this for? labels, according to an embodiment of the disclosure.
Figure 13B:
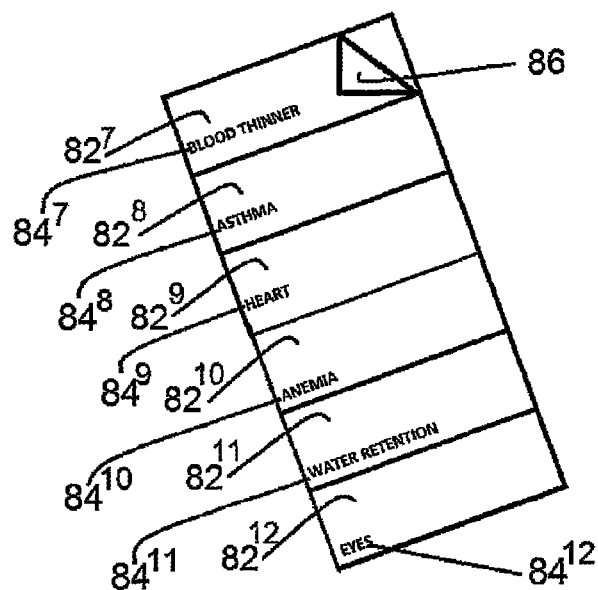
FIG. 13B is a perspective view of a row of What's this for? labels of FIG. 13A, according to an embodiment of the disclosure

Each of the What's this for? tiles $130^{1-4}$ includes the area$^5$ adapted to removably attach thereon a preprinted What's this for? label $82^{1-n}$ which is for the benefit of the user, patient, and/or medical clinician in understanding the role of the specific medicine in treatment of the patient's malady. The notable known medical reason $84^{1-n}$ is provided by the medical practitioner and may be available from the patient's medical practitioner at the time the actual medicine product is prescribed. Referring specifically to FIGS. 13A-13B, there is shown a preprinted sheet 80 of What's this for labels $82^{1-18}$ of a plurality of preprinted sheets 80 of What's this for? labels $82^{1-18}$, according to an exemplary embodiment of the disclosure.

Each of the What's this for? labels 80 can include a plurality of a variety of well known different medical reasons for why users, patients are prescribed or administered actual medicine products in their medicine regimens by their medical practitioner. The following reasons can be preprinted on a What's this for? sheet 80 of What's this for? labels $82^{1-n}$. Medical reasons: $84^{1-n}$ A. Acid reflux, Allergies, Alzheimer, Arthritis, Asthma, Autism, Anti-Anxiety, Acne, Appetite, Anemia, Anti-oxidant. B. Bedsores, Bedwetting, Bipolar, Bladder overactive, Bronchitis, Bursitis, Blood Pressure, Boils. C. Cholesterol, Cancer, Crohn's disease, Canker sore, COPD, Cramps, Cyst D. Dehydration, Depression, Diabetes, Diarrhea, Diverticulitis, Dermatitis, Dyslexia, Digestive Health, Digestive relief. E. Eczema, Epilepsy, Eyes, Ear, Endometriosis. F. Fainting, Fibromyalgia, Fungus. G. Gallbladder, Gallstones, Gout, Gerd, Gas relief. H. Heart, Heartburn, Hemmorrhoids, Hepatisits, Hives, High Potassium, Headache, Hernia, Hyperglcemia. I. Iron deficiency, Irritable Bowel, Itching, Influenza. J. Joints. K. Kidney. L. Leukemia, Lupus, Liver, Lung. M. Menopause, Migraine, Mood, Mononucleosis, Memory, Mesothelioma, Multiple Sclerosis (MS), Myelodysplastic Syndromes (MDS). N. Nails. O. Obesity, Osteoarthritis, Osteomyelitis, Osteoporosis, Obsessive Compulsive Disorder (OCD). P. Pain, Parkinson's, Pink Eye, Pneumonia, Post Nasal Drip, Post-Traumatic Stress Disorder, Premenstrual Syndrome, Psoriasis, Prostrate, Psychosis, Probiotic. R. Ringworm, Rosacea, Rash. S. Scabies, Sciatica, Schizophrenia, Shingles, Sinus, Sleep disorder, Staph infection (MRSA), Strep throat (*Streptococcus* Group A), Stomach, Sun Burn, Supplement, Skin. T. Tuberculosis, Thyroid. U. Ulcers, Urinary Tract, Infection, Urinary tract supplement. V. Vertigo. W. Warts, Water Retention, Weight Management. Y. Yeast Infection.

Each of the preprinted sheets of What's this for? labels 80 includes a plurality of What's this for? labels $82^{1-n}$ including the an adhesive back having a peel-off membrane 86. The preprinted What's this for? sheets 80 includes a plurality of What's this for? $82^{1-n}$, wherein each of the What's this for? labels 82 is preprinted with associated information 184 including the notable known medical reason 84 for prescribing the corresponding actual medicine product 180 to the patient. As noted above, the What's this for? sheets 80 of What's this for? labels 82 can be printed on commercially available Avery Labels.

In one embodiment of the present disclosure, the associated information 184 including the notable known prescriptive medical reason $84^{1-n}$ for prescribing the corresponding actual medicine product 180 includes any one of the following notable known medical reasons $84^{1-n}$: Chemo $84^1$, Headache $84^2$, Pain $84^3$, Digestive Health $84^4$, Osteoporosis $84^5$, Ears $84^6$, Blood Thinner $84^7$, Asthma $84^8$, Heart $84^9$, Anemia $84^{10}$, Water Retention $84^{11}$, Eyes $84^{12}$, Diabetes $84^{13}$, Blood Pressure $84^{14}$, Cholesterol $84^{15}$, Depression $84^{16}$, Eczema $84^{17}$, and Arthritis $84^{18}$.

In an exemplary embodiment of the disclosure, the preprinted What's this for? Labels $82^{1-n}$ adhesive backed-peel off member 86 can each be adhesively attached to a mateable mounting magnet 186 of the plurality of mateable mounting magnets 186 for enabling removably attaching the preprinted What's this for? Labels $82^{1-n}$ to the correct What's this for? tile 130 aligned with the medicine exemplar container 30 removably attached thereon the corresponding aligned Medicine/Supplement Exemplar tile 126 of the second row $116^2$ of the periodic daily event matrix of tiles $106^1$ of the medicine manager chart 100.

Figure 5A:
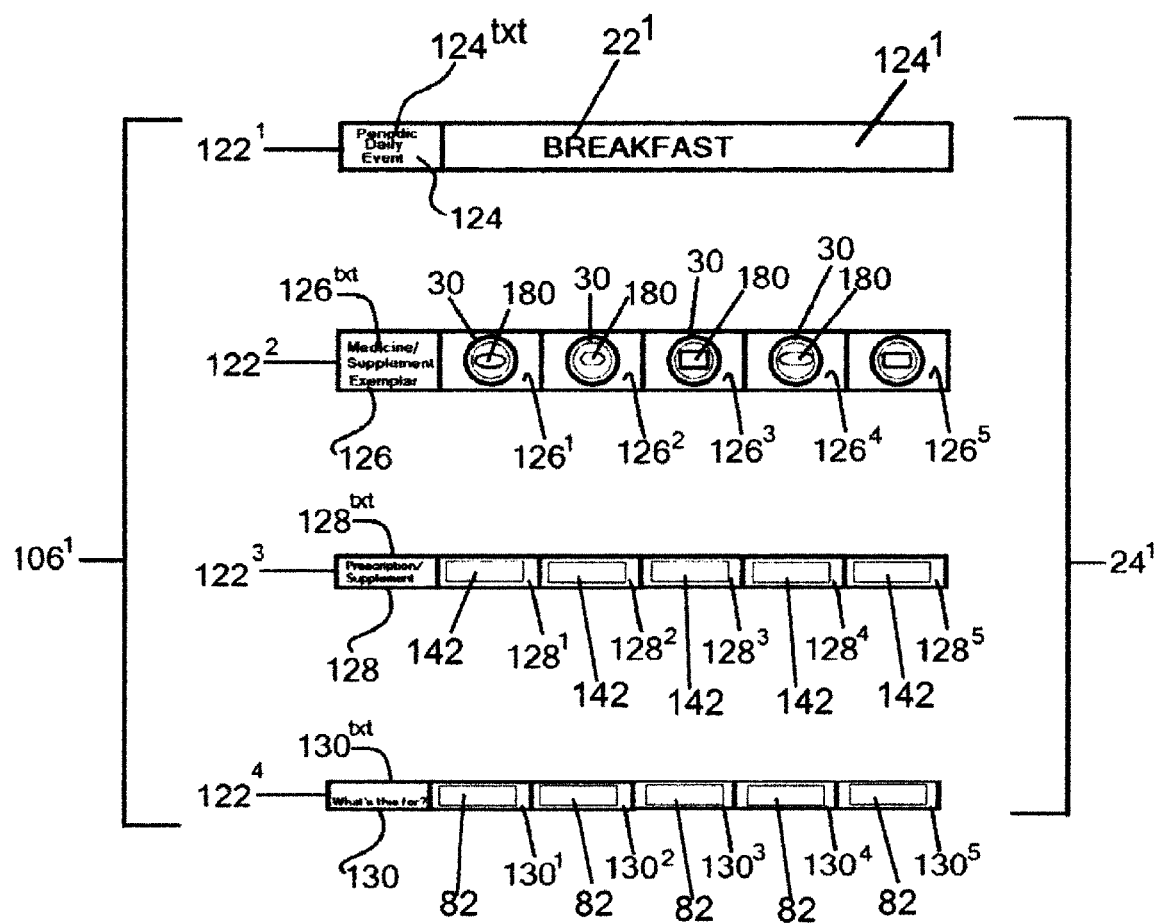
FIG. 5A is an exploded sectional view of a Breakfast matrix of tiles of FIG. 4, according to an embodiment of the disclosure.
Figure 5B:
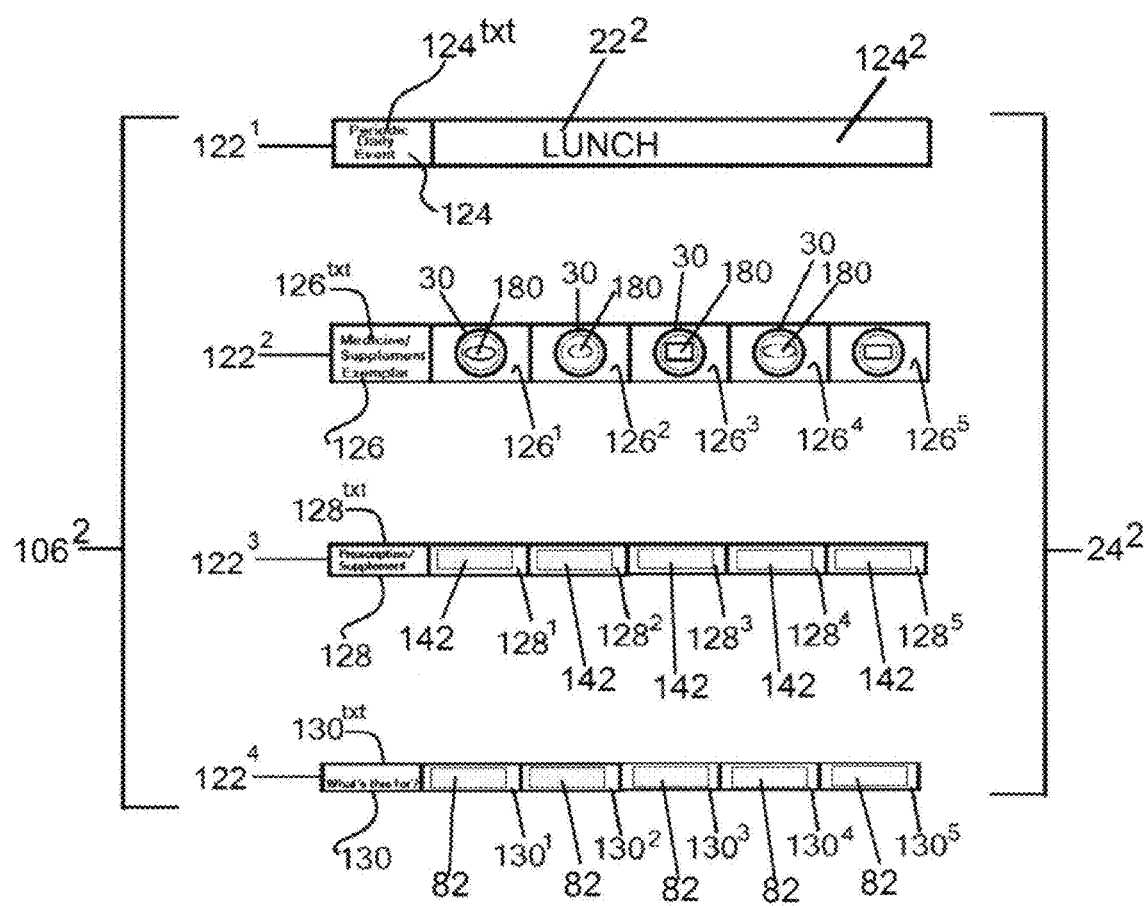
FIG. 5B is an exploded sectional view of a Lunch matrix of tiles of FIG. 4, according to an embodiment of the disclosure.
Figure 5C:
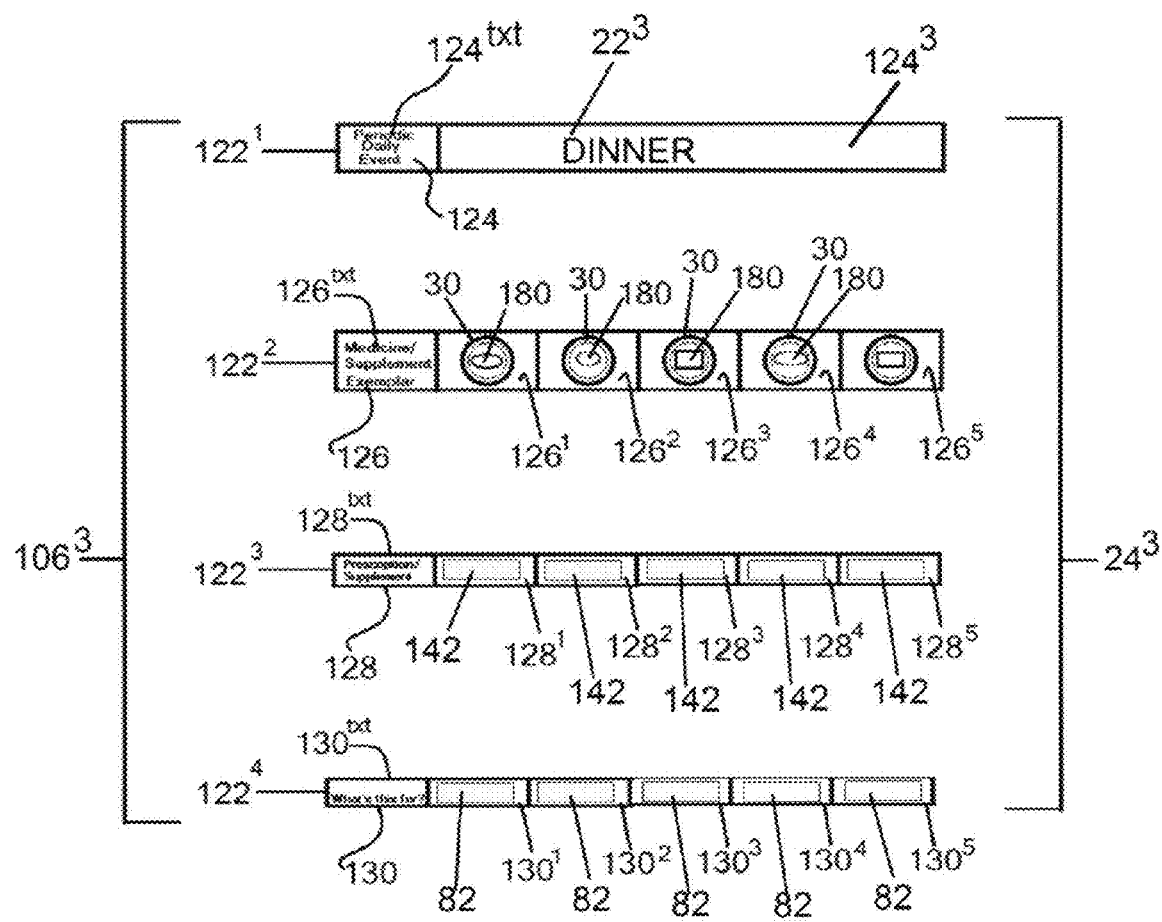
FIG. 5C is an exploded sectional view of a Dinner matrix of tiles of FIG. 4, according to an embodiment of the disclosure.
Figure 5D:
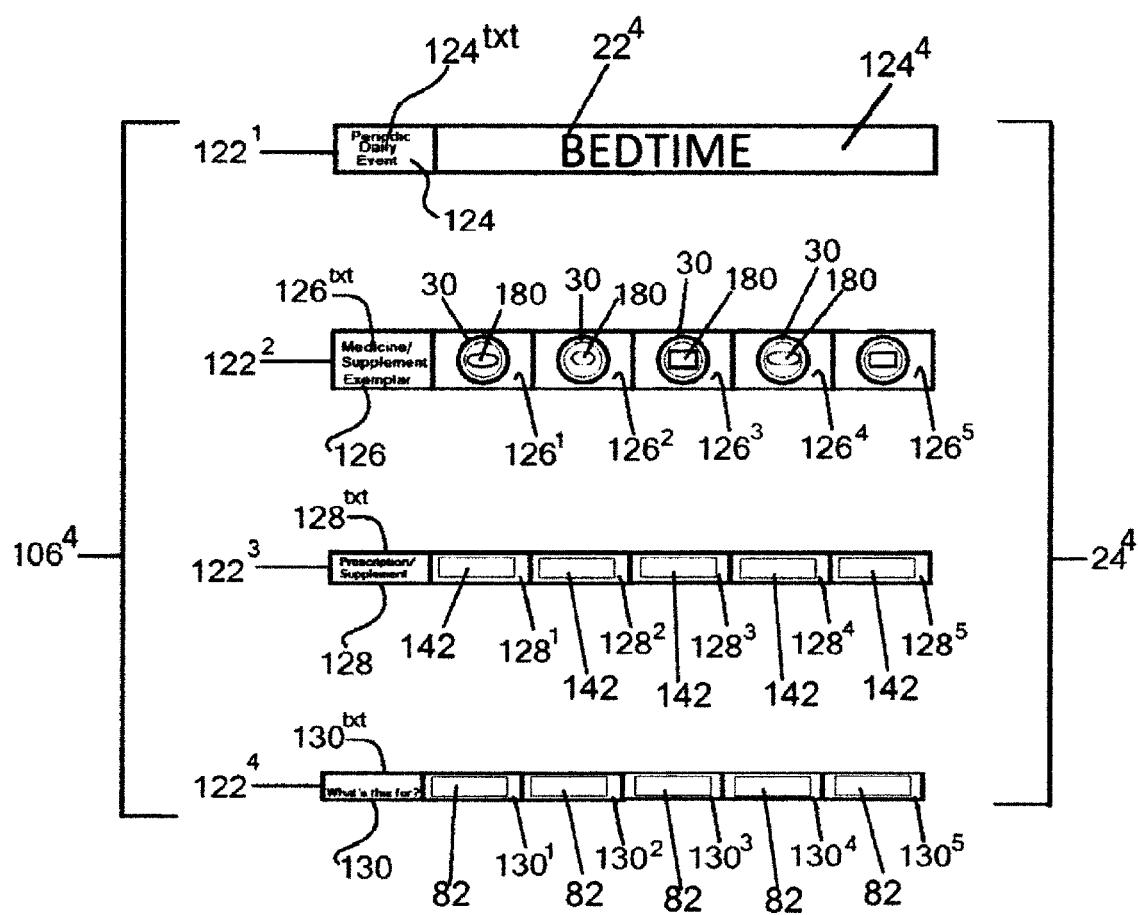
FIG. 5D is an exploded sectional view of a Bedtime matrix of tiles of FIG. 4, according to an embodiment of the disclosure.
Figure 5E:
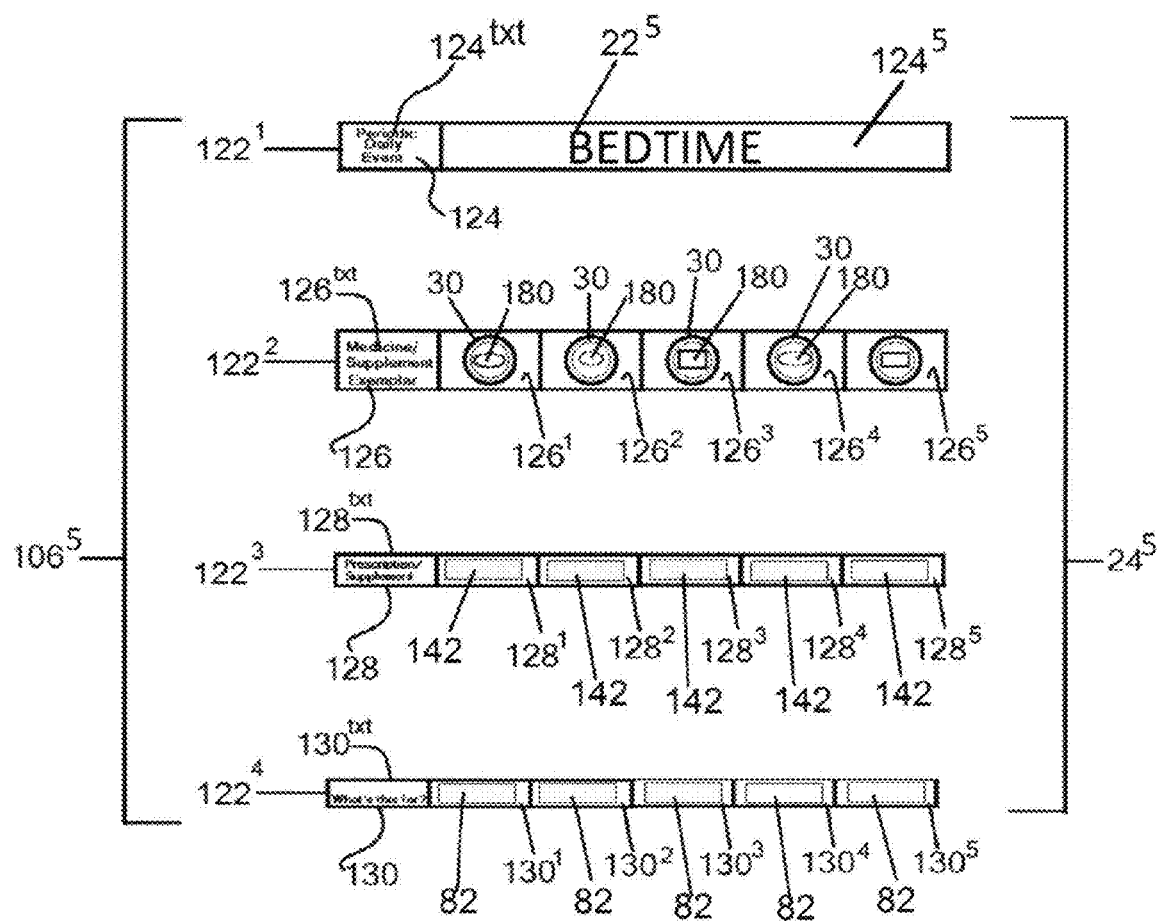
FIG. 5E is an exploded sectional view of an As Needed matrix of tiles of FIG. 4, according to an embodiment of the disclosure.
Figure 6:
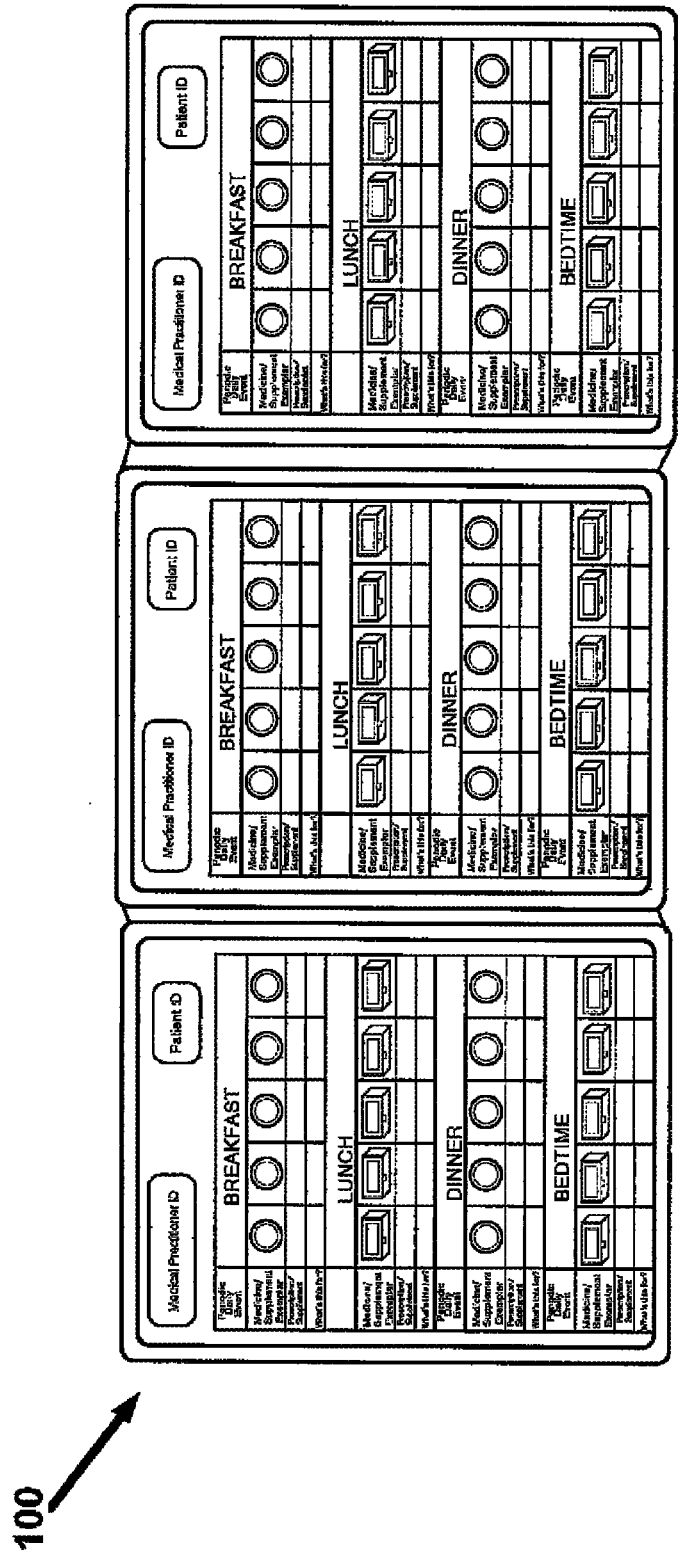
FIG. 6 is a front perspective view of a multi-medicine management chart, according to an embodiment of the disclosure.

Referring, again, to FIGS. 2-5E, with more particularity to FIG. 5A, the medicine manager chart 100 includes a first periodic daily event matrix of tiles $106^1$ completely color shaded with the first color $24^1$, yellow $24^1$, including the Periodic Daily Event header tile 124 heading the first row $116^1$ including the first periodic daily event tile $124^1$ bearing the preprinted viewing text of the first periodic daily event $22^1$, "Breakfast" $22^1$, and repeating the standard essential tiles: the Medicine/Supplement header tile 126 heading the second row $116^2$ of Medicine/Supplement Exemplar tiles $126^{1-5}$; the Prescription/Supplement header tile 128 heading the third row $116^3$ of the Prescription/Supplement tiles $128^{1-5}$; and the What's this for? header tile 130 heading the fourth row $116^4$ of the "What's this for?" tiles $130^{1-5}$ forming a Breakfast matrix of tiles $106^1$.

In this exemplary embodiment of the present disclosure, the first periodic daily event matrix of tiles $106^1$ is completely shaded with the first preselected color $24^1$, yellow $24^1$, bearing the first daily event header text $124^1$, of the first periodic daily event, Breakfast $22^1$, preprinted thereon an area$^{22-1}$ of the first row of the first periodic daily event matrix of tiles $106^1$ forming a Breakfast matrix of tiles $106^1$. The Breakfast matrix of tiles $106^1$ indicates the first periodic daily event, Breakfast $22^1$, as the daily event of the day the specific patient is to be administered the actual medicine product(s) 180, a dosage 146 of which is depicted in the Prescriptions/Supplements tile 128 and the dosage 146 of the actual medicine product 180 of which is contained within the color shaded cubicle 406 completely shaded in the first color $24^1$, yellow $24^1$, bearing the viewing text of the first periodic daily event $22^1$, Breakfast $22^1$, for each day of the week, as described in more detail below, of the actual medicine product daily organizer 400. The correct identity of the actual medicine product is discerned from the exemplar contained therewithin the medicine exemplar containers 30 removably attached to the Medicine/Supplement Exemplar tiles $126^{1-5}$ within the Breakfast matrix of tiles $106^1$ of the medicine management chart 100, and the medicine exemplar containers 30 remotely removably attached to the Breakfast drawer $260^1$ maintained within the medicine management cabinet 200.

Within the medicine manager chart 100 the periodic daily event matrix of tiles 106 is repeated in a second periodic daily event matrix of tiles $106^2$. Referring, again, to FIGS. 2-5E, with more particularity to FIG. 5B, the medicine manager chart 100 includes a second periodic daily event matrix of tiles $106^2$ completely colored with the second color $24^2$, orange $24^2$, including the Periodic Daily Event header tile 124 heading the first row $116^1$ including the first periodic daily event tile $124^1$ bearing the preprinted viewing text of the second periodic daily event $22^2$, "Lunch" $22^2$, and repeating the standard essential tiles: the Medicine/Supplement header tile 126 heading the second row $116^2$ of Medicine/Supplement Exemplar tiles $126^{1-5}$; the Prescription/Supplement header tile 128 heading the third row $116^3$ of the Prescription/Supplement tiles $128^{1-5}$; and the What's this for? header tile 130 heading the fourth row $116^4$ of the "What's this for?" tiles $130^{1-5}$ forming a Lunch matrix of tiles $106^2$.

In this exemplary embodiment of the disclosure, the second periodic daily event matrix of tiles $106^2$ completely shaded with the second color $24^2$, orange $24^2$, bearing the second daily event header text $124^2$, of the second periodic daily event, Lunch $22^2$, preprinted thereon the area$^{22-2}$ of the first row of the second periodic daily event matrix of tiles $106^2$ forming a Lunch matrix of tiles $106^2$ indicating the second periodic daily event, Lunch $22^2$, as the daily event of the day the specific patient is to be administered the actual medicine product(s) 180, a dosage 146 of which is retained within a color shaded cubicle 406 completely colored in the color $24^2$, orange $24^2$, bearing the viewing text of the second periodic daily event $22^2$, Lunch $22^2$, for each day of the week, as described in more detail below, so that the actual medicine product daily organizer 400 corresponds to the medicine exemplar containers 30 removably attached to the Medicine/Supplement Exemplar tiles $126^{1-5}$ within the matrix of tiles $106^2$ of the medicine management chart 100.

The correct identity of the actual medicine product is discerned from the exemplar contained therewithin the medicine exemplar containers 30 removably attached to the Medicine/Supplement Exemplar tiles $126^{1-5}$ within the Lunch matrix of tiles $106^2$ of the medicine management chart 100, and the medicine exemplar containers 30 remotely removably attached to the Lunch drawers $260^2$ maintained within the medicine management cabinet 200.

Within the medicine manager chart 100 the periodic daily event matrix of tiles 106 is repeated in the third periodic daily event matrix of tiles $106^3$. Referring, again, to FIGS. 2-5E, with more particularity to FIG. 5C, the medicine manager chart 100 includes a third periodic daily event matrix of tiles $106^3$ completely colored with the third color $24^3$, green $24^3$, including the Periodic Daily Event header tile 124 heading the first row $116^1$ including the third periodic daily event tile $124^3$ bearing the preprinted viewing text of the third periodic daily event $22^3$, "Dinner" $22^3$, and repeating the standard essential tiles: the Medicine/Supplement header tile 126 heading the second row $116^2$ of Medicine/Supplement Exemplar tiles $126^{1-5}$; the Prescription/Supplement header tile 128 heading the third row $116^3$ of the Prescription/Supplement tiles $128^{1-5}$; and the What's this for? header tile 130 heading the fourth row $116^4$ of the "What's this for?" tiles $130^{1-5}$ forming a Dinner matrix of tiles $106^3$.

In this exemplary embodiment of the present disclosure, the third periodic daily event matrix of tiles $106^3$ completely shaded with the third preselected color $24^3$, green $24^3$, bearing the third daily event header text $124^3$, of the third periodic daily event, Dinner $22^3$, preprinted thereon the area$^{22-3}$ of the first row of the third periodic daily event matrix of tiles $106^3$ forming the Dinner matrix of tiles $106^3$ indicating the third periodic daily event, Dinner $22^3$, as the daily event of the day the specific patient is to be administered the actual medicine product(s) 180, a dosage 146 of which is retained within a color shaded cubicle 406 of which is retained within the color shaded cubicle 406 completely colored in the third color $24^3$, green $24^3$, bearing the viewing text of the third periodic daily event $22^3$, Dinner $22^3$, for each day of the week, as described in more detail below, so that the actual medicine product daily organizer 400 corresponds to the medicine exemplar containers 30 removably attached to the Medicine/Supplement Exemplar tiles $126^{1-5}$ within the Dinner matrix of tiles $106^3$. The correct identity of the actual medicine product is discerned from the exemplar contained therewithin the medicine exemplar containers 30 removably attached to the Medicine/Supplement Exemplar tiles $126^{1-5}$ within the Dinner matrix of tiles $106^3$ of the medicine management chart 100, and the medicine exemplar containers 30 remotely removably attached to the Dinner drawers $260^3$ maintained within the medicine management cabinet 200.

Within the medicine manager chart 100 the periodic daily event matrix of tiles 106 is repeated in the fourth periodic daily event matrix of tiles $106^4$. Referring, again, to FIGS. 2-5E, with more particularity to FIG. 5D, the medicine manager chart 100 includes a fourth periodic daily event matrix of tiles $106^4$ completely colored with the fourth color $24^4$, blue $24^4$, including the Periodic Daily Event header tile 124 heading the first row $116^1$ including the fourth periodic daily event tile $124^4$ bearing the preprinted viewing text of the fourth periodic daily event $22^4$, "Bedtime" $22^4$, and repeating the standard essential tiles: the Medicine/Supplement header tile 126 heading the second row $116^2$ of Medicine/Supplement Exemplar tiles $126^{1-5}$; the Prescription/Supplement header tile 128 heading the third row $116^3$ of the Prescription/Supplement tiles $128^{1-5}$; and the What's this for? header tile 130 heading the fourth row $116^4$ of the "What's this for?" tiles $130^{1-5}$ forming a Bedtime matrix of tiles $106^4$.

In this exemplary embodiment of the present disclosure, the fourth periodic daily event matrix of tiles $106^4$ completely shaded with the fourth preselected color $24^4$, blue $24^4$, bearing the fourth daily event header text $124^4$, of the fourth periodic daily event, "Bedtime" $22^4$, preprinted thereon the area$^{22-4}$ of the first row of the fourth periodic daily event matrix of tiles $106^3$ forming a Bedtime matrix of tiles $106^4$ indicating the fourth periodic daily event, "Bedtime" $22^4$, as the daily event of the day the specific patient is to be administered the actual medicine product(s) 180, a dosage 146 of which is retained within a color shaded cubicle 406 completely colored in the fourth preselected color $24^4$, blue $24^4$, bearing the viewing text of the fourth periodic daily event $22^4$, Bedtime $22^4$, for each day of the week, as described in more detail below, so that the actual medicine product daily organizer 400 corresponds to the medicine exemplar containers 30 removably attached to the Medicine/Supplement Exemplar tiles $126^{1-5}$ within the Bedtime matrix of tiles $106^4$. The correct identity of the actual medicine product is discerned from the exemplar contained therewithin the medicine exemplar containers 30 removably attached to the Medicine/Supplement Exemplar tiles $126^{1-5}$ within the Bedtime matrix of tiles $106^4$ of the medicine management chart 100, and the medicine exemplar containers 30 remotely removably attached to the Bedtime drawers $260^4$ maintained within the medicine management cabinet 200.

In an exemplary embodiment of the present disclosure, a fifth periodic daily event matrix of tiles $106^5$ of the plurality of the periodic daily event matrices of tiles $106^{1-5}$ is repeated in a fifth periodic daily matrix of tiles $106^5$. The fifth periodic daily event matrix of tiles $106^5$ is completely colored with the fifth color $24^5$, purple $24^5$, bearing the fifth header $124^5$ preprinted viewing text of the fifth periodic daily event $22^5$ "As Needed" $22^5$ and repeating the standard essential tiles: the Medicine/Supplement header tile 126, Medicine/Supplement Exemplar tiles $126^{1-5}$, the Prescription/Supplement header tile 128, the Prescription/Supplement tiles $128^{1-5}$, and the What's this for? header tile 130, and the "What's this for?" tiles $130^{1-5}$ forming an As Needed periodic daily event matrix of tiles $106^5$.

In this exemplary embodiment of the present disclosure, the fifth periodic daily event matrix of tiles $106^5$ completely shaded with the fifth preselected color $24^5$, purple $24^5$, bearing the fifth periodic daily event, "As Needed" $22^5$, preprinted thereon the area$^{22-5}$ of the first row of the fifth periodic daily event matrix of tiles $106^2$ forming an As Needed matrix of tiles $106^5$ indicating the fifth periodic daily event, "As Needed" $22^5$, as the daily event of the day the specific patient is to be administered the actual medicine product(s) 180, a dosage 146 of which is retained within a color shaded cubicle 406 completely colored in the fourth preselected color $24^5$, purple $24^5$, bearing the viewing text of the fifth periodic daily event $22^5$, "As Needed" $22^5$, for each day of the week, as described in more detail below, so that the actual medicine product daily organizer 400 corresponds to the medicine exemplar containers 30 removably attached to the to the Medicine/Supplement Exemplar tiles $126^{1-5}$ within the As needed periodic daily event matrix of tiles $106^5$. An example of which is for pain medicine administered to the specific patient for the relief of pain. The correct identity of the actual medicine product is discerned from the exemplar contained therewithin the medicine exemplar containers 30 removably attached to the Medicine/Supplement Exemplar tiles $126^{1-5}$ within the As Needed matrix of tiles $106^5$ of the medicine management chart 100, and the medicine exemplar containers 30 remotely removably attached to the As Needed drawers $260^5$ maintained within the medicine management cabinet 200.

In another embodiment of the disclosure, the associated information $184^1$ for the Prescription/Supplements tiles $128^{1-5}$ can be the reprint copy of the indicators 801 obtained from the medical practitioner at the time the specific patient is provided with his/her medicine regimen. The user, patient, caregiver, medicine practitioner, can reprint the indicators 801 onto laser printable magnetic sheets (not shown) to provide the sheet of Prescription/Supplements labels 800. The laser printable magnetic sheets can be provided by Uline at www.uline.com. Each of the reprinted sheets of Prescription/Supplements labels 800 of the indicators reprinted onto the printable magnetic sheets can be sized to form each of the Prescription/Supplements labels 802 and cut to fit therewithin each of the Prescription/Supplement tiles $128^{1-5}$ corresponding to the correct medicine exemplar container 30 of the medicine manager chart 100, and accordingly removably attached thereon.

In another embodiment, the user, patient, care giver, and/or medical practitioner can write with a writing instrument the reprint copy of the indicators 140 into the appropriate "Prescription/Supplement" tile $128^{1-5}$ corresponding to the exemplar 182 contained in the aligned adjacent medicine exemplar container 30 within the periodic daily event matrix of tiles within the medicine management chart. The writing instrument can include erasable ink, non-toxic erasable ink.

The "What's this for?" associated information $184^2$ can be obtained from the reprint copy of the prescription and prescriptive information administered by the medical practitioner each with a notable known reason for administering the medicine product. The "What's this for?" associated information 184 can be printed on commercially available Avery® labels with an adhesive back having a peel-off membrane provided. The sheet of What's this for? labels 80 can be adhered upon a mateable mounting magnets 186 for enabling releasably attaching directly each of a What's this for? labels 82 within the What's this for? tile $130^{1-4}$. A user peels off one of the preprinted What's this for? labels 82 labels and adheres the What's this for? labels 82 label to a mateable mounting magnet 186 for removably attaching the What's this for? label 82 to the appropriate What's this for? tile $130^{1-4}$ within the medicine management chart 100.

In another embodiment, the Prescription/Supplements labels 800, the preprinted periodic daily event labels 70, and the What's this for? labels 80, can be preprinted onto laser printable magnetic sheets. The laser printed magnetic sheets can be provided by Uline at www.uline.com, as noted above. Each of the reprinted copies of the What's this for? associated information $184^2$ can be sized and cut to form each What's this for? labels 82 to fit therewithin each of the What's this for? tiles $130^{1-n}$ corresponding to the medicine exemplar container 30 removably attached on the aligned corresponding Medicine/Supplement Exemplar tile $126^{1-5}$ of the medicine manager chart 100, and accordingly removably attached thereon.

In another embodiment, the user, patient, care giver, and/or medical practitioner can write the associated information into the appropriate "What's this for?" tile $130^{1-5}$ corresponding to the aligned medicine exemplar container 30 removably attached on the aligned corresponding Medicine/Supplement Exemplar tile $126^{1-5}$ of the medicine manager chart 100. The writing instrument can include erasable ink, non-toxic erasable ink, or chalk.

In another embodiment of the present disclosure the front side 108 of the medicine management chart 100 can include thin washable exterior surface 46 capable of receiving ink that is capable of being erased or wiped off the washable exterior surface. In another embodiment the front side 108 of the medicine management chart 100 includes the thin washable exterior surface 46 capable of receiving chalk that is capable of being erased off the thin washable exterior surface 46.

In another embodiment of the present disclosure the medicine manager chart 100 can be permanently attached to the portable rigid magnetic board 40. In, yet, another embodiment of the present invention the medicine manager chart 100 can be releasably attached to the permanent exterior magnetic board 220 of the medicine management cabinet 200.

FIGS. 19-28 are views of a medicine management cabinet 200 according to embodiments of the disclosure. The medicine management cabinet 200, comprises a housing body 202 defining an open interior region 204, the housing body 202 including an open front 206, a closed interior back wall 208, a closed exterior back wall 210, a top wall 212 and a bottom floor plane 214, a right side wall 216, a left side wall 218, wherein the closed exterior back wall 210 includes a permanently attached ferromagnetic wall 220 adapted and operable to act as a permanent exterior magnetic board 220, as more clearly shown in FIG. 23 in a rear perspective view of the medicine management cabinet 200. In another embodiment of the disclosure the permanent exterior magnetic board 220 is a mirror.

Figure 21:
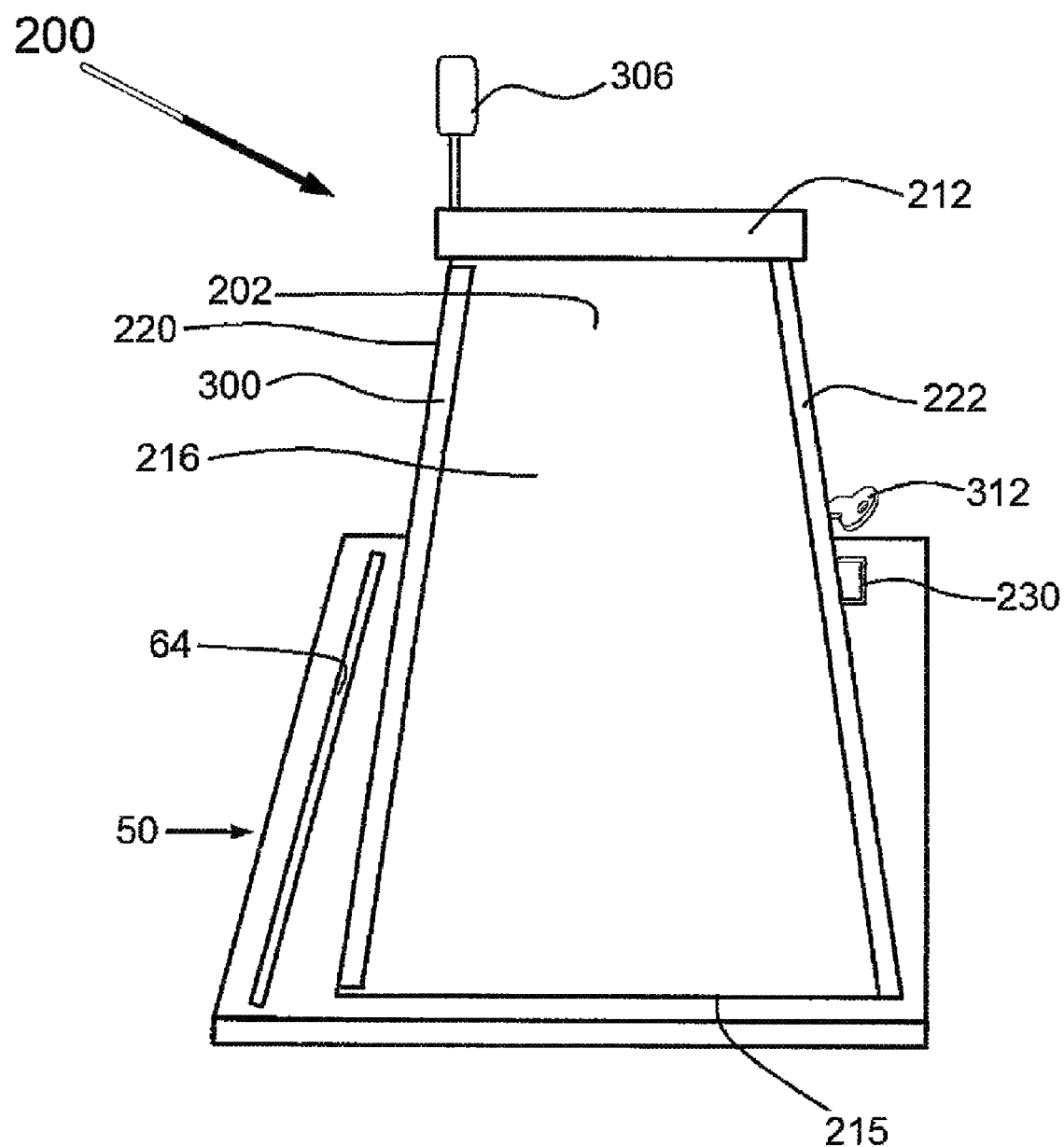
FIG. 21 is a side perspective view of a medicine management cabinet and a mounting platform, according to an embodiment of the disclosure.

Referring to FIGS. 21 and 22, in an embodiment of the disclosure, the medicine management cabinet 200 can have generally a trapezoidal shape. FIGS. 21 and 22 show a side perspective view of the medicine management cabinet 200 having a generally trapezoid shape. FIG. 22 shows the medicine management chart 100 in use with the medicine management cabinet 200. The medicine management chart 100 is releasably attached to the portable rigid magnetic board 40 while the portable rigid magnetic board 40 is mounted onto the mounting platform 50.

The medicine management cabinet 200 includes a housing body 202 including a top wall 212, an exterior bottom floor 215, a bottom floor plane 214, the right side wall 216, and the left side wall 218, the closed exterior back wall 210, having a generally trapezoid shape providing at least two walls having an angle provided to frame the open interior region 204 of the housing body 202. The trapezoid shape provides an increasing depth from the top wall 212 to the bottom floor plane 214 of the interior of the medicine management cabinet 200 enabling for storing small sized actual medicine products within one or more top drawers 260, medium sized actual medicine products within one or more middle drawers 260, and larger sized actual medicine product containers 190 within one or more bottom drawers 260 of the medicine management cabinet 200.

In another embodiment, the medicine management cabinet 200 can have a more particularly a trapezoid prism shape. In another embodiment, the medicine management cabinet 200 can have a generally isosceles trapezoid shape. In another embodiment the medicine management cabinet 200 can include any one of an isosceles shape selected from one of the following: an acute trapezoid shape, a right trapezoid shape, an obtuse trapezoid, or a three-sides equal trapezoid.

In an embodiment of the disclosure, the medicine management cabinet 200 includes a generally rectangular shape, as shown in FIGS. 19-20, 23-25. In another embodiment according to the present disclosure, the medicine management cabinet 200 can include other generally linear geometric shapes including a square, rectangle, triangle, rhombus.

In the exemplary embodiments of the disclosure, the medicine management cabinet 100 is formed from medically approved stainless steel, painted stainless steel, melamine, or from other suitable durable materials, for example, acrylic, polypropylene, polystyrene, polythene, PVC, epoxy resin, and melamine, plastic, polyethylene, wood, water resistant cloth, canvas, known to those of skill in the art, in order to accommodate preservation of a variety of actual medicine products 180 in a variety of forms. In another embodiment the medicine management cabinet 100 is manufactured with stainless steel. In another embodiment the medicine management cabinet 200 or other metal materials having an inherent ferromagnetic element and/or an inherent magnetic element for enabling the removably attachment of the plurality of mateable mounting magnets 30, and mateable mounting storage containers 248, periodic daily event labels 72, and the medicine exemplar containers 30, the patient identification card 120, and the medical practitioner identification card 118 and other mateable mounting components.

Referring to FIGS. 19-20, 23-25A and FIGS. 26-29, in another embodiment of the disclosure, the medicine management cabinet 200 can have generally a rectangular shape.

The medicine management cabinet 200 includes a door 222 having a front planar surface 224 and a rear planar surface 226. The front planar surface 224 of the door 222 is formed by a front wall which is a solid front wall 224 having a generally rectangular shape. The entirety of the rear planar surface 226 of the door 222 includes a ferromagnetic substrate 228 flush with the rear planar surface therein adapted and operable for the rear planar surface 226 to act as a magnetic inside door 228. The magnetic inside door 228 is adapted and operable for enabling removably attaching one or more mateable mounting storage containers 248 thereon.

Each of the mateable mounting storage containers 248 of the one or more of mateable mounting storage containers 248 includes a mateable mounting magnet 186 of the plurality of mateable mounting magnets 186 for enabling removably attaching the one or more of the plurality of mateable mounting storage containers 248 thereon the magnetic inside door 228 and/or the permanent exterior magnetic board 220.

The door 222 extends from the bottom floor plane 214 to the top wall 212 and from the right side wall 216 to the left side wall 218, being pivotally mounted to the housing body 202 by means of the hinges 234 thereby allowing the door 222 to be operable for selectively providing access to the open interior region 204 of the medicine management cabinet 200, the one or more drawers 260 within the medicine management cabinet 200, the plurality of mateable mounting storage containers 248 the magnetic inside door 228, and for covering the open front 206 of the open interior region 204.

FIGS. 19-20, and 24-25A illustrates the medicine management cabinet 200 in a closed position, including the door 222 providing the solid front wall 224 on the outside of the medicine management cabinet 200. The door 222 of the medicine management cabinet 200 has a generally rectangular shape. The door 222 is connected to an exterior edge 232 of the left side wall 218 of the medicine management cabinet 200 by at least two hinges 234 connected to an exterior edge 232 of the left side wall 218. In another embodiment of the medicine management cabinet the door 222 is connected to an exterior edge 236 of the right side wall 216 of the medicine management cabinet 200 by hinges 234. In an embodiment of the disclosure, the door 222 of the medicine management cabinet is hingedly attached along a right marginal edge of the right side wall 216 of the medicine management cabinet for enabling for selective opening and closing of the medicine management cabinet 200. In another embodiment of the disclosure, the door 222 of the medicine management cabinet is hingedly attached along a left marginal edge of the left side wall 218 of the medicine management cabinet 100 for enabling for selective opening and closing of the medicine management cabinet 200.

The door 222 includes a length (L) and width (W) and thickness (T) selected with reference to the length (L) measured from the interior surface 240 of the top wall 212 to the interior surface 238 of the bottom floor plane 214, and a width (W) selected with reference to the width (W) measured from the exterior edge 236 of the right side wall 216 to the exterior edge 232 of the left side wall 218. Although the door 222 shown in FIG. 1 has a length (L) less than the length (L) measured from an exterior surface 242 of the top wall 212 to the exterior bottom floor plane 215 of the bottom floor plane 214, the door 222 can be adapted to include a length (L) greater than the length (L) extending from the exterior surface 242 of the top wall 212 to the exterior bottom floor plane 215 of the bottom floor plane 214, and accordingly, providing an overhanging portion of the door 222 at the top wall 212 of the medicine management cabinet 200 by which a user can selectively open or close the door 222. In addition, the overhanging portion provides a barrier to a variety of components that can be placed upon the top wall 212 of the medicine management cabinet 200 for easy access.

The medicine management cabinet 200 includes a locking means 246 adapted and operable for the selectively opening and closing the door 222. In the exemplary embodiment, the locking means 246 is a door lock 310 integrally machined within the door 222. Referring to FIGS. 19-22, 24, and 25A the door lock 310 and a key 312 is positioned within the solid front wall 224 of the door 222 extending to the magnetic inside door 228 for enabling locking of the door 222 to the medicine management cabinet 200 in the closed position in order to protect unauthorized persons from gaining access to the plurality of actual medicine product containers 190 of the specific patient's medicine regimen, and the plurality of auxiliary products 264 stored therewithin the medicine management cabinet 200.

The locking means 246 of the door 222 can include a conventional door lock 310 and key 312, as shown in FIGS. 19-22, 24, and 25A to secure a plurality of actual medicine product containers 190, and the plurality of auxiliary products 264 therewithin the medicine management cabinet 200. The locking means 246 can include any one of the following comprising: a key in knob cylinder, manual dial, rim latch, dead bolt, pad lock, lever handle, cam, disc tumbler, electronic, digital, magnetic, individual recognition lock.

Figure 23:
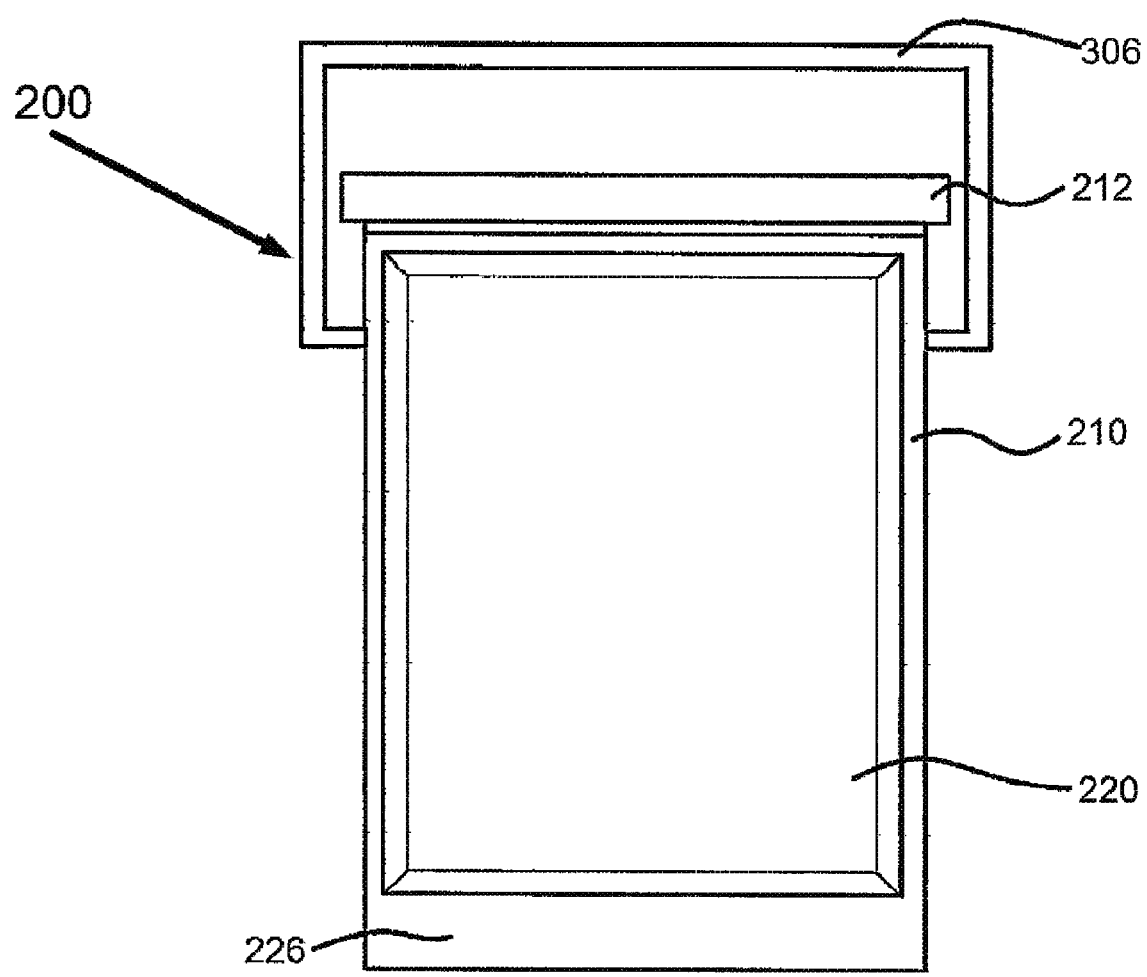
FIG. 23 is a rear perspective view of a medicine management cabinet, according to an embodiment of the disclosure.

FIG. 23 is a rear perspective view of the medicine management cabinet 200 showing the closed exterior back wall 210 with the permanent exterior magnetic board 220 attached flush with the closed exterior back wall 210. The permanent exterior magnetic board 220 can be used by the user, patient, caretaker, medicine practitioner to removably attach any one of the following: plurality of mateable mounting magnets, plurality of the medicine management charts 100, plurality of mateable mounting storage containers 248, auxiliary products 264 with mateable mounting capability, or any auxiliary product with mateable mounting capability.

FIGS. 17, and 18A-18B, shows the medicine management cabinet 200 in use with the medicine management chart 100. The portable rigid magnetic board 40 can include a supporting means 42 to support the portable rigid magnetic board 40 in use with the medicine manager chart 100 removably attached thereon for facilitating the display of the medicine manager chart 100 to a user, patient, care giver, and/or medical practitioner. In an exemplary embodiment of the invention the medicine manager chart 100 releasably attached to the portable rigid magnetic board 40 and in combination is supported by the supporting means 50, the mounting platform 50, as shown in FIGS. 15A-15B, FIGS. 16A-16B, 17, 18A, and 22. More particularly, FIG. 17 shows the medicine management chart 100 removably attached to the portable rigid magnetic board 40 which is removably inserted into the recessed U-channel 64 of the mounting platform 50 leaning against the medicine management cabinet 200. FIGS. 18A-18C, with reference to FIG. 3, wherein the user, patient, caregiver, family member, medicine practitioner, selects the exemplar 182 of a first actual medicine product 180 stored in the medicine management cabinet 200 prescribed to be administered to the specific patient at the first periodic daily event of the day $22^1$, Breakfast $22^1$, from a first actual medicine product container 190 prescribed in the medicine regimen of the specific patient, and places the exemplar 182 into the medicine exemplar container 30 and seals the transparent sealing cap 36 onto the transparent body 32 of the medicine exemplar container 30.

Accordingly, the medicine exemplar container 30 having a first exemplar $182^1$ contained therewithin is removably attached to a first Medicine/Supplement Exemplar tile $126^1$ of the Breakfast matrix of tiles $124^1$ by means of the attached mateable mounting magnet 186. Accordingly, the user, patient, caregiver, medical practitioner, removably attaches a first Prescription/Supplements labels $802^1$ corresponding to the first exemplar $182^1$ containing preprinted indicators 801 of a first actual medicine product $180^1$ identified by the first exemplar $182^1$.

The one or more indicators 801 can include a pharmaceutical identification 804, or a prescription name, or a trade name, or a generic name, of the actual medicine product 180, a dosage 806, a time of administration 808, or adverse reactions 810 of the actual medicine product 180.

Subsequently, the user, patient, caregiver, medicine practitioner removably attaches a first What's this for? labels $82^1$ onto the first What's this for? tile $130^1$ within the Breakfast matrix of tiles $124^1$. In this exemplary embodiment, the associated to information 184 including the notable known prescriptive medical reason $84^{1-n}$ for prescribing the corresponding actual medicine product $180^1$ includes any one of the notable known medical reasons $84^{1-n}$ detailed above, including the following notable known medical reasons: Chemo $84^1$, Headache $84^2$, Pain $84^3$, Digestive Health $84^4$, Osteoporosis $84^5$, Ears $84^6$, Blood Thinner $84^7$, Asthma $84^8$, Heart $84^9$, Anemia $84^{10}$, Water Retention $84^{11}$, Eyes $84^{12}$, Diabetes $84^{13}$, Blood Pressure $84^{14}$, Cholesterol $84^{15}$, Depression $84^{16}$, Eczema $84^{17}$, and Arthritis $84^1$.

This method is repeated for each actual medicine product 180 of the plurality of actual medicine products 180 of the specific patient's medical regimen.

FIG. 18C shows the exemplar 182 is an ampule exemplar $182^4$ which is placed in the medicine exemplar container having a rectangular shape adapted and operable to contain the ampule exemplar $182^4$. As shown in FIG. 18A, the ampule exemplar $182^4$ is removably attached to the medicine management chart 100, in the exemplary embodiment, within the Lunch matrix of tiles $124^2$ within the fifth Medicine/Supplement Exemplar tile $126^5$. The ampule exemplar $182^4$ of an ampule 450 of actual medicine product 190 can be used, in particular, when the specific patient is prescribed morphine for pain during cancer treatment or while the specific patient is cared for under a hospice protocol medicine regimen. An ampule cutter 324 can be stored within the medicine management cabinet 200.

Subsequently, additional exemplars 182 of actual medicine products 180 prescribed to the specific patient included in his/her medicine regimen are managed and identified in the above manner such that the user, patient, caregiver, family member, medicine practitioner continues providing exemplars 182 from the corresponding actual medicine product containers 190 stored within the medicine management cabinet 200 into medicine exemplar containers 30 for each of the actual medicine products 180 of the plurality of actual medicine products 180 completing the Lunch matrix of tiles $124^2$, the Dinner matrix of tiles $124^3$, and the Bedtime matrix of tiles $124^4$.

In an embodiment of the disclosure, one or more of the one or more drawers 260 further includes a docking station 354 for enabling charging and recharging of the mobile communication device, and the cell phone, or any compatible device. With reference to FIG. 24, the medicine management cabinet 200 includes the top wall which is pivotally attached to the closed exterior back wall 210 for selectively providing access to a top open region 340 wherein a removable tray is maintained. The medicine management and identification apparatus, according to claim 1, wherein the top wall 212 opens to a top open region 340 having four perimeter walls via a hinge mechanism, wherein at least one of the perimeter walls of the top open region 340 includes a docking station 354 adapted and operative to recharge the cell phone or a mobile communication device 500. Chargeable devices, a cell phone, or digital camera, or a mobile communications device 500 can be charged at the rechargeable electric supply docking station 354.

As shown in FIG. 24, the medicine management chart 100 is displayed in a top open region 340 wherein the medicine management chart 100 is leaning against the top wall 212 of the medicine management cabinet 200 so that the medicine management chart 100 is readily viewed and accessible to the user, patient, caretaker, medicine practitioner.

Referring to FIGS. 25A-25B, the medicine management cabinet 200 can include the top wall 212 which is pivotally attached to the closed exterior back wall 210 for selectively providing access to a top open region 340 wherein a removable tray 342 is placed and maintained. The removable tray 342 includes two opposing open handles, a first open handle 350 and second open handle 352 for enabling carrying of the removable tray 342. The removable tray 342 provides easy access to auxiliary products 264, cell phone, the mobile communications device 500, digital camera, stored therewithin. The interior of the surface of the top wall 240 can include a mirror 356.

Referring again to FIGS. 20-22, 24-25A, the medicine management cabinet 200 includes an open storage pocket 300 formed by a rectangular panel 302 having a recess in the front thereof, being permanently attached to a rear exterior surface of the top wall 212 of the medicine cabinet 200 and an exterior bottom floor plane 215 of the bottom floor plane 214 of the medicine management cabinet 200, such that an open storage pocket 300 behind the closed exterior back wall 210 of the medicine management cabinet 200 is formed having an open slot being provided between the top wall 212 and the bottom floor plane 214 for enabling access to the the open storage pocket 300, wherein the open storage pocket 300 is adapted and operable to slidably receive and store the portable magnetic board 40 in use when having the medicine manager chart 100 removably attached thereon. A user, patient, care giver, and/or medical clinician can selectively slide the medicine manager chart 100 removably attached to the portable magnetic board 40 in and out to selectively view the medicine manager chart 100 by mounting the medicine manager chart 100 on the mounting platform against the medicine management cabinet 200, or mount the medicine management chart 100 within the open top region 340 against the interior surface 240 of the top wall 212 of the medicine management cabinet 200.

Referring to FIGS. 26-29, the medicine management cabinet 200 is shown in an open position illustrative of an interior of the exemplary embodiment of the medicine management cabinet 200 of the medicine management and identification system 10 showing the magnetic inside door 228 of the door 222 and the open interior region 204 of the housing body 202. A plurality of mateable mounting storage containers 248 are provided thereon the magnetic inside door 228, and one or more drawers 260 are provided in the open interior region 204 of the housing body 202.

The medicine management cabinet 200 houses one or more mateable mounting storage containers $248^{1-5}$ wherein each of the plurality of mateable mounting storage containers 248 includes a mateable mounting magnet 186 adapted and operable to removably attach to the magnetic inside door 228, and the permanent exterior magnetic board 220, for enabling relocation of one or more of the plurality of the mateable mounting storage containers $248^{1-5}$ thereon the magnetic inside door 228 and the permanent exterior magnetic board 220.

The inside magnet inside door 228 includes one or more of the plurality of mateable mounting storage containers $248^{1-5}$. Each of the one or more of the mateable mounting storage containers $248^{1-5}$ includes a mateable mounting magnet 186 for enabling removably attaching the one or more of the mateable mounting storage containers $248^{1-n}$ to the magnetic inside door 228 of the medicine management cabinet 200. By use of the mateable mounting magnet 186 attachment means each of the mateable mounting storage containers $248^{1-n}$ can be removably and movably positioned thereon the magnetic inside door 228 of the medicine management cabinet 200 in a variety of arrangements in use specified by the user, patient, care giver, and or medical practitioner.

The mateable mounting storage container 248 and one or more of the plurality of auxiliary products 264 can inherently include a ferromagnetic element or magnetic element, and, accordingly, the mateable mounting magnet 30 is not attached to the mateable mounting storage container 248. A method of affixing the ferromagnetic element, or the magnetic element, or the mateable mounting magnet 186 to the mateable mounting storage container 248 can include any one of the following affixing methods, gluing, soldering, welding, and machining.

In another embodiment, the mateable mounting storage container 248 may be adapted to include a ferromagnetic element or magnetic element by a method of affixing a mateable mounting magnet 186 to the auxiliary product 264.

In an exemplary embodiment of the disclosure, each of the mateable mounting containers $248^{1-5}$ includes a mateable mounting magnet thereon a rear planar surface 298 of the mateable mounting storage containers 248$^{1-5}$ for enabling removably attaching one or more of the plurality of mateable mounting storage containers 248$^{1-5}$ thereon the magnetic inside door 228 of the medicine management cabinet 200 and/or the permanent exterior magnetic board 220.

In the exemplary embodiment of the disclosure, referring, again, to FIGS. 26-29, the number of five mateable mounting storage containers 248$^{1-5}$ are provided removably attached to the magnetic inside door 228 of the medicine management cabinet 200, and one mateable mounting hook device 250 removably attached to the magnetic inside door 228 of the medicine management cabinet 200.

In the exemplary embodiment of the disclosure, each of the five mateable mounting storage containers 248$^{1-5}$ can include each individual mateable mounting storage containers 248$^{1-5}$ having dimensions not equal in measure to each of the other mateable mounting storage containers 248$^{1-5}$.

In another embodiment of the disclosure, each of the five mateable mounting storage containers 248$^{1-5}$ can include each individual mateable mounting storage container 248$^{1-5}$ each having dimensions equal in measure to each of the other mateable mounting storage containers 248$^{1-5}$.

Figure 27:
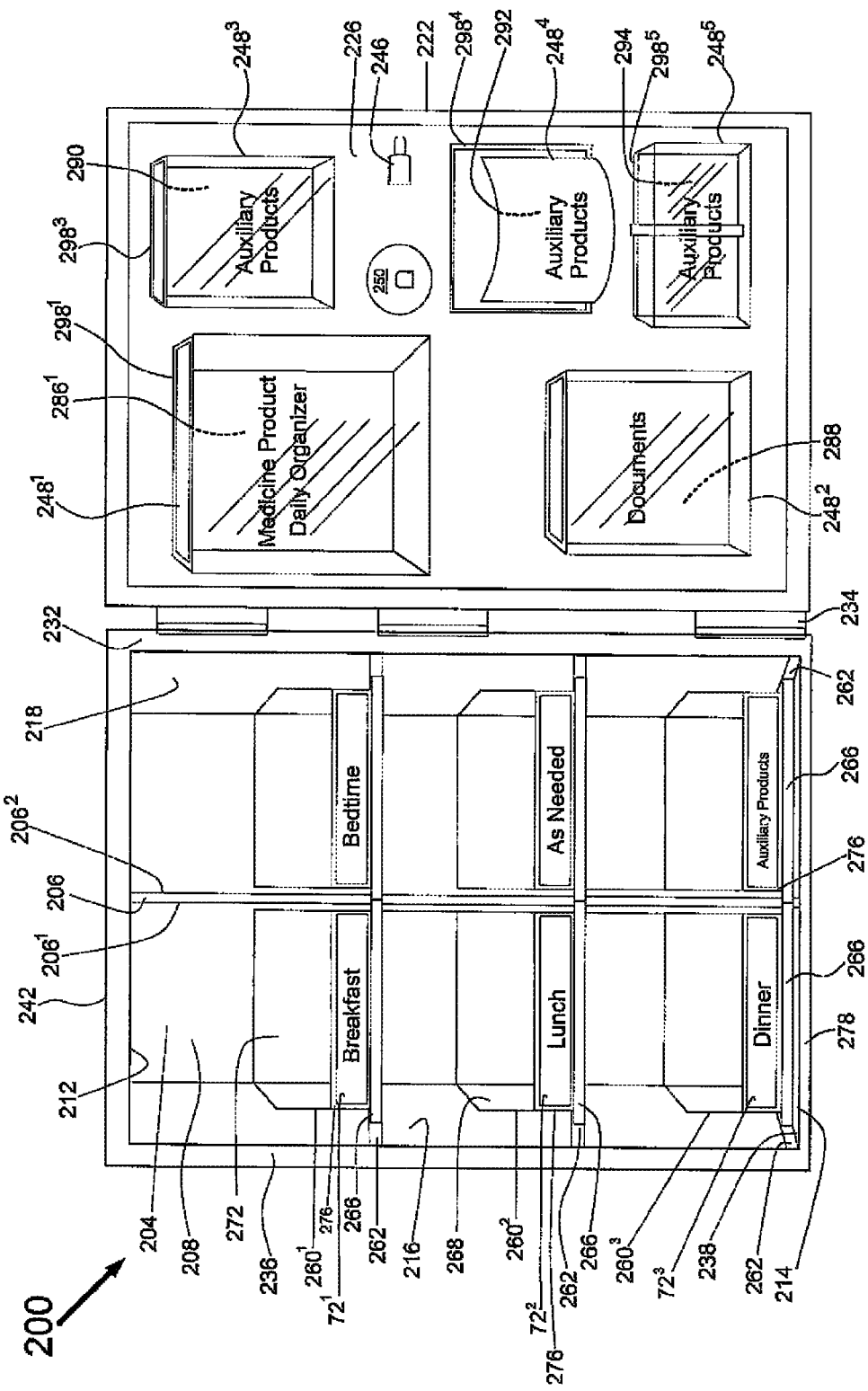
FIG. 27 is a front perspective view of a medicine management cabinet in the open position, according to an embodiment of the disclosure.
Figure 28:
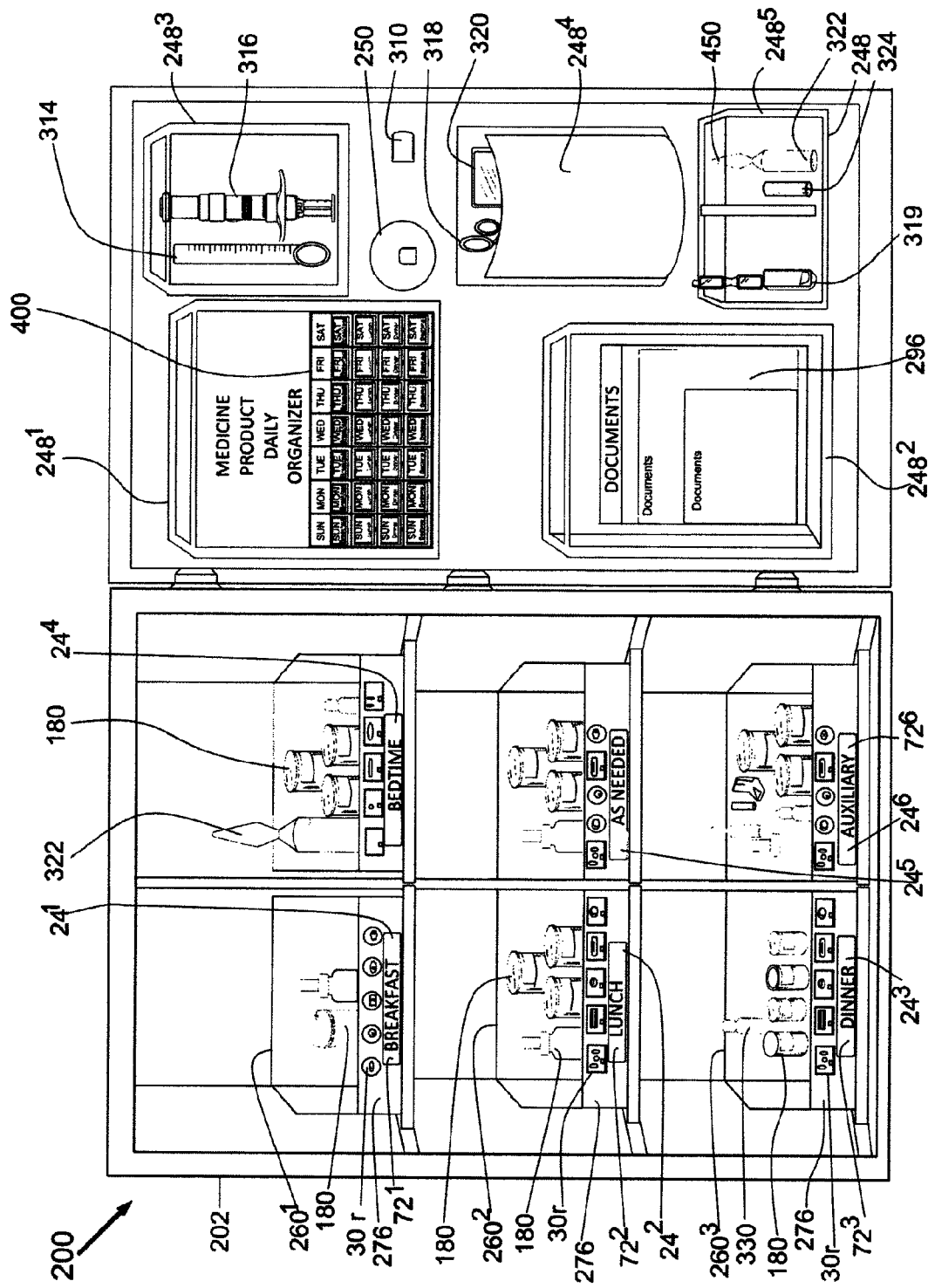
FIG. 28 is a front perspective view of the medicine management cabinet in use, according to an embodiment of the disclosure.

A first mateable mounting storage container 248$^1$ removably attached to the magnetic inside door 228 includes a first interior cavity 249 adapted and operable to store the actual medicine product daily organizer 400, as shown in FIGS. 27 and 28. The first mateable mounting storage container 248$^1$ of the five of the mateable mounting storage containers 248$^{1-5}$ is an actual medicine product daily organizer mateable mounting storage container 248$^1$ configured having dimensions adapted and operable to allow a user to easily insert the actual medicine product daily organizer 400, enabling for maintaining the actual medicine product daily organizer 400 conveniently in a designated place within the medicine management cabinet 200 for ensuring to the user, patient, care giver, family member and/or medical practitioner easy access, retrieveability, and storage, more particularly, safe storage when stored behind the closed and locked door 222 position of the medicine management cabinet 200. In the exemplary embodiment, the first mateable mounting storage container 248$^1$ is manufactured with a transparent plastic material to easily view the contents therewithin.

In another embodiment of the disclosure the medicine record mateable mounting storage container 248$^2$ can be manufactured with a magnetic mesh material.

A second mateable mounting storage container 248$^2$ includes a second interior cavity 288 adapted and operable to contain one or more documents 296, one or more 8.00 inches by 11.00 inches sized documents relating to the specific patient forming a medicine record mateable mounting storage container 248$^2$ is configured having dimensions adapted and operable to allow a user, patient, care giver, family member, medical practitioner, to easily insert a variety of patient documents and medical records 296 enabling for maintaining the patient documents and records 296 including patient documents, and medical records, within a designated place within the medicine management cabinet 200 for ensuring to the user easy access, retrieveability, and storage, more particularly, safe storage when stored behind a locked door 222 position of the medicine management cabinet 200. As shown, in FIG. 28, variety of patient documents and medical records 296 are stored in the medicine record mateable mounting storage container 248$^2$.

In an embodiment of the present disclosure, the medicine record mateable mounting storage container 248$^2$ is manufactured with a translucent material so that the user can easily see through the transparent materials to see the contents within the second interior cavity 288 of the medicine record mateable mounting storage container 248$^2$. The variety of patient documents and medical records 296 can be any one of the patients hospital records, patient blood type, allergies, prescription record in paper or digital form, i.e., USB drive; advance directive for patient advocate form, and the like. In another embodiment of the disclosure the medicine record mateable mounting storage container 248$^2$ can be manufactured with a magnetic mesh material.

A third mateable mounting storage container 248$^3$ includes a third interior cavity 290 adapted and operable to store auxiliary products 264 related to the specific patient. The third mateable mounting storage container 248$^3$ is a mateable mounting product storage container 248$^3$ is configured having dimensions adapted and operable to allow a user, patient, care giver, medical practitioner, to easily insert one or more of auxiliary products 264 therewithin the mateable mounting product storage container 248$^3$. As shown in FIG. 28, a medicine dispenser spoon 314 and a syringe 316 are stored in the third mateable mounting storage container 248$^3$.

The third mateable mounting storage container 248$^5$ provides for enabling for maintaining the medicine dispenser spoon 314 and the syringe 316 within the medicine manager cabinet 200 in one designated place within the interior of the medicine management cabinet 200 for ensuring to the user, patient, care giver, and/or medical practitioner easy access, retrieveability, and storage, more particularly, safe storage when stored behind a locked door 222 position. The third mateable mounting storage container 248$^3$ is manufactured with a translucent material so that the user, patient, care giver, and/or medical practitioner can easily see through the transparent material to see the contents within the third interior cavity 290 of the mateable mounting storage container 248$^3$. In another embodiment of the disclosure the medicine record mateable mounting storage container 248$^2$ can be manufactured with a magnetic mesh material.

As shown in FIG. 28, the auxiliary products 264 stored within the third mateable mounting storage container 248$^3$ can be any one of a syringe, an ampule 450, a spoon with a hollow handle with a dosage 146 measure inscribed thereon, and any one of like medicine dispensers.

The plurality of auxiliary products 264, as detailed above, can include any one of the following: syringe 316, magnifying glasses 319, pill cutter 328, ampule cutter 324, scissors 318, portable mirror 320, bandage, epi pen, q-tips, diabetic needles, diabetic monitor, glucose testing kit, thermometer, gauze, alcohol wipes, disposable antiseptic wipes, toothbrush, toothpaste, mouthwash, peroxide, comb, portable mirror, calendar, disposable gloves, floss, ankle pads, cortisone cream, antiseptic cream, antiseptic tincture, ear phones (not shown).

A fourth mateable mounting storage container 248$^4$ includes a fourth interior cavity 292 adapted and operable to store one or more of the plurality of auxiliary products 264 of the plurality of auxiliary products 264 related to the medicine management of the specific patient to form a second mateable mounting storage container 248$^4$. Referring to FIG. 28, the fourth mateable mounting storage container 248$^4$ includes a fourth interior cavity enclosed by a circumferential wall which is non-translucent which is convenient for any one of auxiliary products 264 that include a sharp edge or a reflective surface, the non-translucent circumferential wall providing a non-translucent wall against displaying scratches that may occur do to the sharp edges of the auxiliary products 264, and preventing against a glare from the reflective surface of the auxiliary product $264^{1-n}$. As shown in FIG. 28, a scissors 318, and a mirror 320 are stored therewithin the fourth mateable mounting storage container $248^4$.

A fifth mateable mounting storage container $248^5$ includes a fifth interior cavity 294 adapted and operable to additional auxiliary products 264 selected from the plurality of auxiliary products 264 related to the medicine management of the specific patient. As shown in FIG. 28, the fifth mateable mounting storage container $248^5$ includes two separate compartments, a first compartment $248^{5a}$, and a second compartment $248^{5b}$, wherein each of the first compartment $248^{5a}$ and the second compartment $248^{5b}$ auxiliary products 264 are stored. A pair of magnifying glasses 319 is stored therewithin the first compartment $248^{5a}$ and, an ampule cutter 324 and an ampule are stored in the second compartment $248^{5b}$ of the fifth mateable mounting storage container $248^5$.

The plurality of auxiliary products 264 can include any one of the following: syringe 316, magnifying glasses 319, pill cutter 328, ampule cutter 324, Epi-pen, scissors 320, portable mirror 320, bandage, aspirin, diabetic needles, diabetic monitor, glucose testing kit, Digital camera, USB drive 504, thermometer, gauze, alcohol wipes, rubbing alcohol, band-aides, disposable antiseptic wipes, scissors, cotton swabs, toothbrush, toothpaste, mouthwash, peroxide, comb, Magnifying glass, calendar, disposable gloves, floss, ankle pads, cortisone cream, antiseptic cream, antiseptic tincture, ear phones.

As shown in FIG. 28, the medicine management cabinet 200 can include one or more mateable mounting hook devices 250 adapted for enabling the display of a hanging apparatus 252. The mateable mounting hook device 250 includes mateable mounting magnet 186 of the plurality of mateable mounting magnets 186 adapted to removably attach the one or more mateable mounting hook devices 250 to the magnetic inside door 228 and the permanent exterior magnetic board 220 for enabling relocation of the mateable mounting hook device 250.

The hanging apparatus 252 can include a stethoscope 254, a calendar 256, a portable mirror 320, a mask, an identification band, an emergency alert device, or other any hanging apparatus selected for the specific patient.

The aspects of the magnetic inside door 228 of the medicine management cabinet 200 described herein may accommodate various alternatives. The mateable mounting storage containers $248^{1-5}$ can be of a variety of different shapes and of a variety of different dimensions of height, width, and depth, the spacing of the mateable mounting storage containers $248^{1-5}$, and manufactured with a ferromagnetic material or a magnetic material for enabling removably attaching each of the mateable mounting auxiliary storage containers $248^{1-5}$ to the inside of the door while allowing the user to move the mateable mounting storage containers $248^{1-5}$ to any area on the magnetic inside 228 door, or to take the mateable mounting storage containers $248^{1-5}$ off from the magnetic inside door 228 as when refilling the contents of the mateable mounting storage containers $248^{1-5}$ with auxiliary products 264. In addition, a user can remove the mateable mounting storage containers $248^{1-5}$ from the magnetic inside door 228 when cleaning the mateable mounting storage containers $248^{1-5}$. The auxiliary products 264 stored contained within each of the mateable mounting storage containers $248^{1-5}$ may be changed to accommodate the needs of the specific patient.

In one embodiment, the back planar surface 226 of the door 222 of the medicine management cabinet 200 is manufactured with steel. In one embodiment back planar surface 226 of the door 222 is integrally machined with a magnetic surface for receiving a compatable magnetic element attached to the mateable mounting storage containers $248^{1-5}$ for enabling removably attaching the mateable mounting storage containers $248^{1-5}$ to the magnetic inside door 228 or to the permanent exterior magnetic board 220 of the medicine management cabinet 200. In the exemplary embodiment, each of the mateable mounting storage containers $248^{1-5}$ includes a rear planar surface 298 integrally machined with a magnetic element including a magnetic surface for removably attaching the mateable mounting storage containers $248^{1-5}$ onto the magnetic inside door 228 or to the permanent exterior magnetic board 220 of the medicine management cabinet 200. In this embodiment each of the mateable mounting storage containers $248^{1-5}$ are movable and can be individually positioned by a patient, medical practitioner, patient care giver, and/or user, on the magnetic inside door 228 or to the permanent exterior magnetic board 220 of the medicine management cabinet 200 so that the user, patient, medical practitioner, patient care giver, can manipulate a medicine manager management scheme selected to his/her individual prescribed medicines and or supplements, tinctures, auxiliary products 264.

In one embodiment of the disclosure, the mateable mounting storage containers 248 can be provided by commercially available magnetic baskets hold up to 5 lbs at Uribio magnetic wall container; or Neat Life Mesh Magnet Organizer.

In one embodiment of the disclosure the mateable mounting storage containers 248 are permanently attached to the magnetic inside door 228. The attachment means is glue, welding, nails for enabling permanent attachment of the mateable mounting storage containers 248 to the magnetic inside door 228 of the medicine management cabinet 200.

Referring, now, to the open interior region 204 of the medicine management cabinet 200, as shown in FIGS. 26-29, the interior of the housing body 202 of the medicine management cabinet 200 includes an open interior region 204 having at least one divider wall 206 positioned vertically within the open interior region 204 for enabling division of the open interior region 204 into two vertical open interior portions, a first vertical open interior portion $204^1$ and a second vertical open interior portion $204^2$. The divider wall 206 includes a first side $206^1$ and a second side $206^2$. The first vertical open interior portion $204^1$ includes a right side wall$^1$ 216 that is consubstantial with the right side wall 216 of the housing body 202 and a left side wall$^1$ that is consubstantial with the first side $206^1$ of the divider wall 206 and, accordingly, the second vertical open interior portion $204^2$ includes a right side wall$^2$ consubstantial with the second side $206^2$ of the divider wall 206 and a left side wall$^2$ consubstantial with the second side $206^2$ of the divider wall 206 of the medicine management cabinet 200.

The first side $206^1$ of the divider wall 206 and the right side wall 216 of the medicine management cabinet 200 of the first vertical open interior portion $204^1$ each include a mounting means for one or more drawers 260 maintained within the first vertical open interior portion $204^1$ of the housing body 202 of the medicine management cabinet 200. The mounting means can include a series of one or more channeled mounting tracks 262 integrally machined within the right side wall 216 of the medicine management cabinet 200 and the first side wall $206^1$ of the divider wall 206, and, accordingly, a second series of one or more channeled mounting tracks 262 are integrally machined within the left side wall of the medicine management cabinet 200 and the second side $206^2$ of the divider wall 206 for slidably receiving a right marginal edge and a left marginal edge of the base floor plane 274 of each drawer 260 of the one or more drawers 260 housed in the first vertical open interior portion $204^1$ of the medicine management cabinet 200 so that the drawers 260 align vertically in the chronological arrangement depicted in the periodic daily event color code sheet 20 within the first vertical open interior portion $204^1$.

Accordingly, the second side $206^2$ of the divider wall 206 and the left side wall 218 of the medicine management cabinet 200 of the second vertical open interior portion $204^1$ of the housing body 202 includes the channeled mounting track 262 for slidably receiving a right marginal edge and a left marginal edge of the base floor plane 274 of each of the drawers 260 so that the drawers 260 align vertically in the chronological arrangement depicted in the periodic daily event color code sheet 20 within the first vertical open interior portion $204^1$ and, accordingly, within the second vertical open interior portion $204^2$ of the medicine management cabinet 200.

In the exemplary embodiment, as shown in FIGS. 36A-36D each of the drawers 260 include two opposing upstanding side walls, an upstanding right side wall 268, and an upstanding left side wall 270, a base floor plane 274, an upstanding rear wall 272, and a raised front wall 276. The upstanding right side wall includes a right top edge $267^1$ and a right bottom edge $269^1$. The upstanding right side wall includes a right front edge $268^1$ and the left side wall includes a left front edge $268^2$, each having identical slopes $S^1$.

The raised front wall 276 extends upward from a front surface of the base floor plane 274 for enabling maintaining actual medicine product containers 190, for example, pill bottles, supplement bottles, ampules 450, auxiliary products 264 stored within each of the drawers 260.

Figure 29:
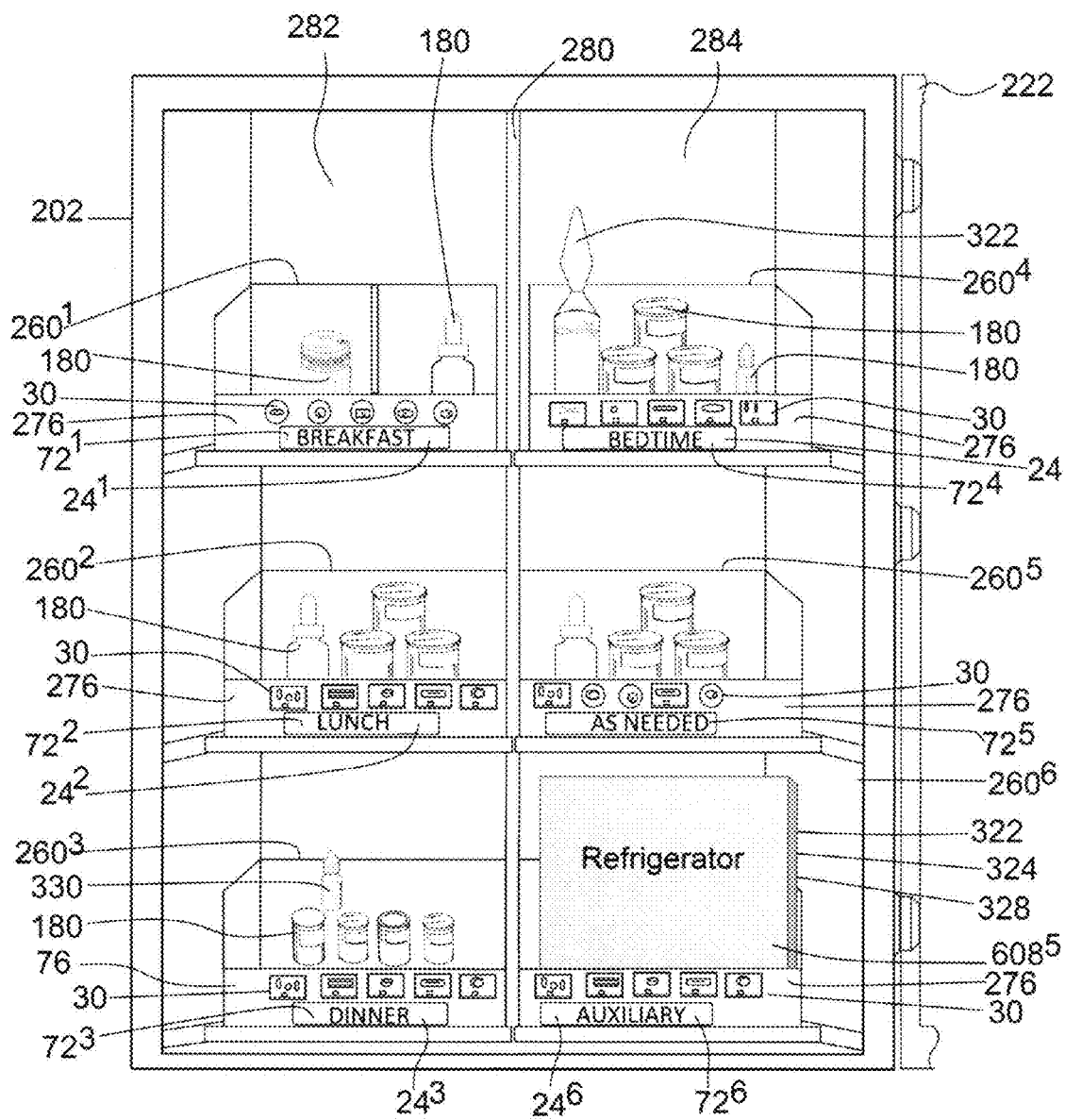
FIG. 29 is a sectional view of a medicine management cabinet in use, according to an embodiment of the disclosure.
Figure 30:
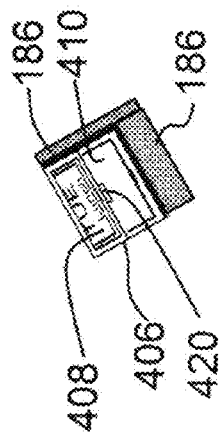
FIG. 30A is a front planar view of an actual medicine product daily organizer, according to an embodiment of the disclosure.
FIG. 30B is a sectional view of a color shaded cubicle of the actual medicine product daily organizer of FIG. 30A, according to an embodiment of the disclosure.

In the exemplary embodiment of the disclosure, as shown more particularly in FIGS. 27-29 the drawers are identifiable with the periodic daily events of the day $22^{1-4}$ as depicted within each of the periodic daily event matrix of tiles $106^{1-4}$ as discerned from the periodic daily event color code sheet 20. Therefore, the drawers 260 within the medicine management cabinet 200 include a periodic daily dispensing time system depicting the periodic daily events of the day $22^{1-n}$, Breakfast $22^1$, Lunch $22^2$, Dinner $22^3$, and Bedtime $22^4$, and As Needed $22^5$ corresponding to the chronological arrangement of the medicine management chart 100 and the actual medicine product daily organizer 400 so that the user, patient, caregiver, medical practitioner, or multiple users, patients, caregivers, medical practitioners, can easily manage the plurality of actual medicine products 190 prescribed in the medicine regiment to the patient at the same time.

Figures 11A, 11B:
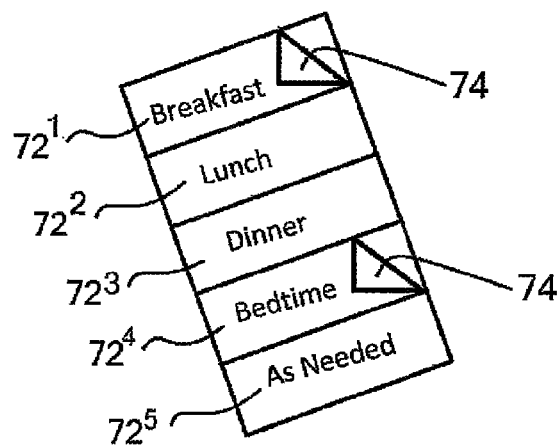
FIG. 11A is a front planar view of a sheet of periodic daily event labels, according to an embodiment of the disclosure.
FIG. 11B is a perspective view of a row of periodic daily event labels of FIG. 11A, according to an embodiment of the disclosure.

The periodic daily event of the day $22^{1-5}$ displayed on each of the drawers 260 is provided by a sheet of periodic daily event labels 70 provided by the preprinted sheets of periodic daily event labels 70 including the plurality of periodic daily event labels $72^{1-5}$ including an adhesive back having a peel off membrane 74, as shown in FIGS. 11A-11B. The sheets of periodic daily event labels 70 can, also, be printed on a ferromagnetic material, or a magnetic material that mates with the ferromagnetic element of the raised front wall 276 of each drawer 260 for enabling removably attaching of the periodic daily event labels $72^{1-5}$ to the raised front wall 276 of any one of the drawers 260 within the medicine management cabinet 200, as described in more detail below.

In an embodiment of the disclosure, one or more of the plurality of drawers 260 further includes a docking station 354 for enabling charging and recharging of the cell phone 500, or the mobile communications device 500, or any compatible device.

In another embodiment of the disclosure, each of the one or more drawers 260 is manufactured with a transparent material including a color shade corresponding to the color $24^{1-n}$ of the periodic daily event of the day $22^{1-n}$ as depicted in the periodic in the medicine management chart 100 including the corresponding viewing text of the periodic daily event of the day $22^{1-5}$ printed thereon for visually corresponding the drawer 260 to the corresponding periodic daily event matrix of tiles $106^{1-4}$ of the medicine manage chart 100 and the associated information 184, more particularly, the visual identification of the actual medicine product 190 by means of the exemplar 182 contained in the medicine exemplar container 30.

In the exemplary embodiment of the disclosure, the medicine management cabinet 200, includes a plurality of drawers $260^{1-6}$ adapted and operable to store a plurality of actual medicine product containers 190 containing a plurality of actual medicine products depicted in the medicine regimen of the specific patient and a plurality of auxiliary products 264 for the enablement of the implementation of the medicine management and identification system 10 based on the chronological arrangement of the medicine management chart 100, and the actual medicine product daily organizer 400 as depicted from the periodic daily event color code sheet 20.

As shown in FIGS. 27-29 A first drawer $260^1$ bears the viewing text of the first periodic daily event of the day $22^1$ which is "Breakfast" $22^1$, and is completely color shaded in the first color $24^1$ which is "yellow" $24^1$ forming a Breakfast drawer $260^1$. A second drawer $260^2$ bears the viewing text of the second periodic daily event of the day $22^2$ which is "Lunch" $22^2$, and is completely color shaded in the second color $24^2$ which is "orange" $24^2$ forming a Lunch drawer $260^2$. A third drawer $260^3$ bears the viewing text of the third periodic daily event of the day 22 which is "Dinner" $22^3$, and is completely color shaded in the third color $24^3$ which is green $24^3$ forming a Dinner drawer $260^3$. A fourth drawer $260^4$ bears the viewing text of the fourth periodic daily event of the day $22^4$ which is "Bedtime" $22^4$, and is completely color shaded in the fourth color $24^4$ which is blue $24^4$ forming a Bedtime drawer $260^4$. A fifth drawer $260^5$ bears the viewing text of the fifth periodic daily event of the day $22^5$ which is "As Needed" $22^5$, and is completely color shaded in the fifth color $24^5$ which is purple $24^5$ forming an As Needed drawer $260^5$.

A sixth drawer $260^6$ can be included in the medicine management cabinet 200 which bears the viewing text "Auxiliary Products $22^6$ and is completely color shaded in a sixth color $22^6$ which is purple forming an "Auxiliary Product" drawer $260^6$ for enabling the storage of auxiliary products 264 that assist in implementing the medicine management and identification system 10 for the specific patient.

Each of the one or more drawers 260 of the medicine management cabinet 200 includes a periodic daily event label $72^{1-5}$, a Breakfast label $72^1$ to form the Breakfast drawer $260^1$, a Lunch label $72^2$ to form the Lunch drawer $260^2$, a Dinner label $72^3$ to form the Dinner drawer $260^3$, a Bedtime label $72^4$ to form the Bedtime drawer $260^4$, an As Needed label $72^5$ to form the As Needed drawer $260^5$ for corresponding each of the drawers $260^{1-5}$ and its contents of actual medicine products 190 stored therewithin to the periodic daily events of the day $22^{1-4}$ as ascertained from the periodic daily event color-code sheet 20 and, accordingly, depicted on the medicine management chart 100 and, accordingly, depicted on the actual medicine product daily organizer 400. By way of example, the Breakfast drawer 260$^1$ stores the actual medicine product containers 190 containing the actual medicine product 190 to be used for the exemplar 182 to be placed in the corresponding medicine exemplar container 30 within the corresponding Medicine/Supplement Exemplar tile 126$^{1-5}$ within the corresponding Breakfast matrix of tiles 106$^1$ of the medicine management chart 100, and, accordingly, the actual medicine product 190 a dosage of which to be placed in the corresponding to the row of Breakfast color shaded cubicles 92 of the actual medicine product daily organizer 400.

Referring specifically to FIGS. 11A-11B, there is shown a preprinted sheet of periodic daily event labels 70 of a plurality of preprinted sheets of periodic daily event labels 70 according to one exemplary embodiment of the present disclosure. Each of the preprinted sheets of periodic daily event labels 70 includes a plurality of periodic daily event labels 72 including an adhesive backed-peel off member 74, wherein one or more of the plurality of periodic daily event labels 72 is completely shaded in one color 24 of each of the colors 24$^1$-24$^2$ of the variety of different colors 24 as indicated on the periodic daily event color-code sheet 20 and bears the viewing text of the periodic daily event 22$^{1-5}$ of the plurality of different periodic daily events 22$^{1-5}$ of the day preprinted thereon, which together are readily cognizable as representing each of the periodic daily event matrix of tiles 106$^{1-n}$ having the same color 24$^{1-n}$ and bearing the same associated preselected periodic daily event 22$^{1-n}$ preprinted thereon the medicine manager chart 100.

Each of the preprinted periodic daily event labels 72 is adhesively attached to one of the mateable mounting magnets 186 of the plurality of mateable mounting magnets 186 adapted and operative for selectively removably attaching the preprinted periodic daily event label 72 thereon any one of the raised front walls 276 of each of the plurality of drawers 260$^{1-n}$ within the medicine management cabinet 200 so as to visually correlate the drawer 260$^{1-n}$ with actual medicine product containers 190 and auxiliary products 264 stored therewithin and the associated information 184 bearing the periodic daily event matrix of tiles 260$^{1-n}$ of the same color 24 bearing the preselected daily event 22$^{1-n}$ printed thereon.

As shown in FIGS. 11A-11B a first periodic daily event label 72$^1$ is the first color 24$^1$ yellow 24$^1$ and bears the viewing text$^1$ Breakfast 22$^1$ printed thereon; a second periodic daily event label 72$^2$ is the second color 24$^2$ is orange 24$^2$ bears the viewing text$^2$ Lunch 22$^2$ printed thereon, a third periodic daily event label 72$^3$ is the third color 24$^3$ and bears the viewing text$^3$ Dinner 22$^3$ printed thereon; a fourth periodic daily event label 72$^4$ is the fourth color 24$^4$ is blue 24$^4$ and bears the viewing text$^4$ Lunch printed thereon; a fifth periodic daily event label 72$^5$ is the fifth color 24$^5$ is purple 24$^5$ bears the viewing text$^5$ As Needed, printed thereon.

The preprinted periodic daily event labels 72 can be provided by printing the periodic daily event labels 72 with the commercially available Avery® label printing system using adhesive backed-peel off member. In one embodiment the preprinted periodic daily event labels 72 can be printed on laser printed magnetic sheets which can be provided by Uline at www.uline.com.

Implementing the preprinted periodic daily event labels 72, a first periodic daily event label 72$^1$ including the first color 24$^1$ yellow 24$^1$ which bears the viewing text$^1$, Breakfast 22$^1$ printed thereon forming a Breakfast label 72$^1$ and including a mateable mounting magnet 186 is removably attached to a first top drawer 260$^1$ of the medicine management cabinet 200. A second periodic daily event label 72$^2$ including the second color 24$^2$, orange 24$^2$ which bears the viewing text$^2$, Lunch 22$^1$ printed thereon forming a Lunch label 72$^2$ and including a mateable mounting magnet 186 is removably attached to a second drawer 260$^2$ of the medicine management cabinet 200. A third periodic daily event label 72$^3$ including the third color 24$^3$, green 24$^3$ which bears the viewing text$^3$ Dinner 22$^3$ printed thereon forming a Dinner label 72$^3$ and including a mateable mounting magnet 186 is removably attached to a third drawer 260$^3$ which is a base drawer 260$^3$ of the medicine management cabinet 200. A fourth periodic daily event label 72$^4$ including the fourth color 24$^4$, blue 24$^2$ which bears the viewing text$^4$, Bedtime 22$^4$ printed thereon forming a Bedtime label 72$^4$ and including a mateable mounting magnet 186 is removably attached to a fourth drawer 260$^4$ of the medicine management cabinet 200. A fifth periodic daily event label 72$^5$ including the fifth color 24$^5$, purple 24$^5$ which bears the viewing text$^5$, As Needed 22$^5$ printed forming an As Needed label 72$^5$ thereon and including a mateable mounting magnet 186 is removably attached to a fifth drawer 260$^5$ of the medicine management cabinet 200.

In the exemplary embodiment, a sixth periodic daily event label 72$^6$ including a sixth label 72$^6$, white 24$^6$ which bears the viewing text$^6$, Auxiliary Products 22$^6$ printed thereon forming an Auxiliary Products label 72$^6$ and including a mateable mounting magnet 186 is removably attached to a sixth drawer 260$^6$, a second base drawer 260$^6$ of the medicine management cabinet 200.

In addition, the raised front wall 276 of each of the drawers 260 is formed including the ferromagnetic element 277 and is dimensioned and sized for enabling the removable attachment of one or more medicine exemplar containers 30 of the plurality of medicine exemplar containers 30, wherein each of the medicine exemplar containers 30 includes the mateable mounting magnet 186 of the plurality of mateable mounting magnets 186.

As shown in FIGS. 27-29 and FIG. 37, in the exemplary embodiment of the disclosure, as described above, each drawer 260$^{1-6}$ bears the viewing text of the periodic daily event of the day 22$^{1-n}$, Breakfast 22$^1$, Lunch 22$^2$, Dinner 22$^3$, Bedtime 22$^4$, and As Needed 22$^4$ at which time the specific patient is to be administered a dosage 146 of an actual medicine product 180. Further, a remote medicine exemplar container 30$^r$ containing an exemplar 182 of the actual medicine product 180, stored therewithin the drawer 206 in the actual medicine product containers 190 behind the raised front wall 276 of the drawer is removably attached to the raised front wall 276 of each of the drawer 260 corresponding to the periodic daily event of the day 22$^{1-n}$ at which time the specific patient is to take the prescribed actual medicine product 180.

In this manner, the user, patient, caregiver, medicine practitioner, while the user is implementing the medicine management chart 100, can correctly identify the appropriate prescribed actual medicine product 180 to store in the correct drawer bearing the periodic daily event 22$^{1-n}$. Even further, the user, patient, caregiver, medicine practitioner, while the user is implementing the medicine management chart 100, along with the exemplar 186 contained in each of the medicine exemplar containers 30 of the medicine manager chart, and the remote medicine exemplar containers removably attached to the raised front walls 276 of the drawers 260 can correctly identify by prescription name 804, the medical reason for administering the actual medicine product 180, and dosage 146 to dispense into the corresponding color shaded cubicles 92 of the actual medicine product daily organizer 400 to be administered to the specific patient. Accordingly, the practitioner, patient care giver, or patient, can correctly identify the specific prescribed medicine, pill, vitamin, or supplement, etc. to retrieve and fill and/or refill in the patient's actual medicine product daily organizer 400. Therefore, this embodiment provides assurance to the patient, medical practitioner, patient care giver that the medicine can be identified correctly and can be dispensed at the specified time correctly.

As shown in FIGS. 28-29, one or more of the medicine exemplar containers 30 of the plurality of medicine exemplar containers 30 is removably attached to each of the raised front walls 276 of each of the plurality of drawers $260^{1-6}$ forming the remote medicine exemplar containers $30^r$ implemented with the medicine management chart 100. The remote medicine exemplar containers $30^r$ are provided to visually identify and correlate the exemplar 182 contained therewithin each of the remote medicine exemplar containers $30^r$ with the actual medicine product 180 contained in an actual medicine product container 190 stored therewithin the drawer $260^{1-n}$ immediately behind remote medicine exemplar container $30^r$.

The remote medicine exemplar containers $30^r$ can include a color 24 shaded transparent body 32 corresponding to the color 24 identified with the periodic daily event 24 of the day as depicted on the medicine management chart 100 as discerned from the periodic daily event color-code sheet 20. In the exemplary embodiment it is preferred that the transparent sealing cap 36 is a colorless translucent material for facilitating visual observation of the contained exemplar 182 therewithin.

Referring to FIGS. 28-29, the remote medicine exemplar containers $30^r$ are removably attached to the raised front wall 276 positioned face forward facilitating identification of the exemplar 182 stored therein the remote medicine exemplar container $30^r$ and, simultaneously, facilitating identification of the corresponding actual medicine product containers 190 of stock stored in that particular section of the drawer 260 immediately behind the remote medicine exemplar container $30^r$ removably attached to the raised front wall 276 of the drawer 260.

As shown in FIGS. 28-29 the Breakfast drawer $260^1$ includes one or more remote medicine exemplar containers $30^r$ which are each removably attached to the raised front wall 276 of the Breakfast drawer $260^1$, forming a row of one or more Breakfast remote medicine exemplar containers $30^B$ removably attached to the raised front wall of the Breakfast drawer $260^1$, wherein each of the one or more of the Breakfast remote medicine exemplar containers $30^B$ includes a second exemplar 182 of one or more of actual medicine products 180 stored within the Breakfast drawer $260^1$ so as to visually correlate each of the second exemplars 182 contained in each of one or more of the remote Breakfast exemplar containers $30^B$ with the one or more of the actual medicine products$^B$ 180 stored within the Breakfast drawer $260^1$ of the medicine management cabinet 200, and with the exemplar $30^B$ contained therewithin a corresponding medicine exemplar container $30^B$ removably attached within each of the corresponding Medicine/Supplement exemplar tiles $126^{1-5}$ of the second row of the Breakfast matrix of tiles $106^1$ of the medicine management chart 100.

In an embodiment of the disclosure, the Breakfast remote medicine exemplar container $30^{rB}$ can include a transparent body 32 manufactured with a transparent material having the color yellow $24^1$ tint, and the transparent sealing cap 36 is manufactured with a non-colored transparent material.

The Lunch drawer $260^2$ includes one or more remote medicine exemplar containers $30^L$ which are each removably attached to the raised front wall 276 of the Lunch drawer $260^2$, forming a row of one or more Lunch remote medicine exemplar containers $30^L$ removably attached to the raised front wall of the Lunch drawer $260^2$, wherein each of the one or more of the Lunch remote medicine exemplar containers $30^L$ includes a second exemplar $30^L$ 182 of one or more of actual medicine products 180 stored within the Lunch drawer $260^2$ so as to visually correlate each of the second exemplars $182^L$ contained therewithin each of the one or more of the Lunch remote medicine exemplar containers $30^L$ with an actual medicine product $180^L$ of the one or more actual medicine product$^L$ stored within the Lunch drawer $260^2$ of the medicine management cabinet 200 and with the exemplar $30^L$ contained therewithin a corresponding medicine exemplar container $30^L$ removably attached within each of the corresponding Medicine/Supplement exemplar tiles $126^{1-5}$ of the second row of the Lunch matrix of tiles $106^2$ within the medicine management chart 100;

In an embodiment of the disclosure, the Lunch remote medicine exemplar container $30^L$ can include a transparent body 32 manufactured with a transparent material having an orange $24^2$ tint, and the transparent sealing cap 36 is manufactured with a non-colored transparent material.

The Dinner drawer $260^3$ includes one or more remote medicine exemplar containers $30^r$ which are each removably attached to the raised front wall 276 of the Dinner drawer $260^3$, forming a row of Dinner remote medicine exemplar containers $30^D$ removably attached to the raised front wall of the Dinner drawer $260^3$, wherein each of the one or more of the Dinner remote medicine exemplar containers $30^3$ includes an exemplar $182^D$ of one or more of actual medicine products $180^D$ stored within the Dinner drawer $260^3$ so as to visually correlate each of the exemplars $182^D$ contained in each of one or more of the remote Dinner exemplar containers $30^D$ with the one or more of the actual medicine products 180 stored within the Dinner drawer $260^3$ of the medicine management cabinet 200 so as to visually correlate each of the second exemplars $182^D$ contained therewithin each of the one or more of the Dinner remote medicine exemplar containers $30^D$ with an actual medicine product $180^D$ of the one or more actual medicine product$^D$ stored within the Dinner drawer $260^3$ of the medicine management cabinet 200 and with the exemplar $30^D$ contained therewithin a corresponding medicine exemplar container $30^D$ removably attached within each of the corresponding Medicine/Supplement exemplar tiles $126^{1-5}$ of the second row of the Dinner matrix of tiles $106^3$ within the medicine management chart 100.

In an embodiment of the disclosure, the Dinner remote medicine exemplar container $30^D$ can include a transparent body 32 manufactured with a transparent material having a green $24^3$ tint, and the transparent sealing cap 36 is manufactured with a non-colored transparent material.

The Bedtime drawer $260^4$ includes one or more remote medicine exemplar containers $30^r$ which are each removably attached to the raised front wall 276 of the Bedtime drawer $260^4$, forming a row of Bedtime remote medicine exemplar containers $30^{Bt}$ removably attached to the raised front wall of the Bedtime drawer $260^4$, wherein each of the one or more of the Bedtime remote medicine exemplar containers $30^4$ includes an exemplar 182 of one or more of actual medicine products 180 stored within the Bedtime drawer $260^4$ so as to visually correlate each of the exemplars 182 contained in each of one or more of the remote Bedtime exemplar containers $30^{Bt}$ with the one or more of the actual medicine products 180 stored within the Bedtime drawer 260$^4$ of the medicine management cabinet 200 so as to visually correlate each of the second exemplars 182$^{Bt}$ contained therewithin each of the one or more of the Bedtime remote medicine exemplar containers 30$^{Bt}$ with an actual medicine product 180$^{Bt}$ of the one or more actual medicine product$^{Bt}$ stored within the Bedtime drawer 260$^3$ of the medicine management cabinet 200 and with the exemplar 30$^L$ contained therewithin a corresponding medicine exemplar container 30$^L$ removably attached within each of the corresponding Medicine/Supplement exemplar tiles 126$^{1-5}$ of the second row of the Bedtime matrix of tiles 106$^4$ within the medicine management chart 100.

In an embodiment of the disclosure, the Bedtime remote medicine exemplar container 30$^{Bt}$ can include a transparent body 32 manufactured with a transparent material having a blue 24$^4$ tint, and the transparent sealing cap 36 is manufactured with a non-colored transparent material.

The As Needed drawer 260$^5$ includes one or more remote medicine exemplar containers 30$^r$ which are each removably attached to the raised front wall 276 of the As Needed drawer 260$^5$, forming a row of As Needed remote medicine exemplar containers 30$^{An}$ removably attached to the raised front wall of the Bedtime drawer 260$^5$, wherein each of the one or more of the As Needed remote medicine exemplar containers 30$^{An}$ includes an exemplar 182 of one or more of actual medicine products 180 stored within the Bedtime drawer 260$^5$ so as to visually correlate each of the exemplars 182 contained in each of one or more of the remote As Needed exemplar containers 30$^{An}$ with the one or more of the actual medicine products 180$^{An}$ stored within the As Needed drawer 260$^5$ of the medicine management cabinet 200 so as to visually correlate each of the second exemplars 182$^{An}$ contained therewithin each of the one or more of the As Needed remote medicine exemplar containers 30$^{An}$ with an actual medicine product 180$^{An}$ of the one or more actual medicine product$^{An}$ stored within the As Needed drawer 260$^5$ of the medicine management cabinet 200 and with the exemplar 30$^{An}$ contained therewithin a corresponding medicine exemplar container 30$^{An}$ removably attached within each of the corresponding Medicine/Supplement exemplar tiles 126$^{1-5}$ of the second row of the As Needed matrix of tiles 106$^5$ within the medicine management chart 100.

In an embodiment of the disclosure, the As Needed remote medicine exemplar container 30$^{An}$ can include a transparent body 32 manufactured with a transparent material having an orange 24$^5$ tint, and the transparent sealing cap 36 is manufactured with a non-colored transparent material.

The significance of the colors 24$^{1-5}$ consistently used with reference to the medicine management chart 100 and the medicine management cabinet 200 and the actual medicine product daily organizer 400 is that the colors 24$^{1-5}$ become universal and readily recognizable to the specific patient, yellow 24$^1$=Breakfast 22$^1$; Orange 24$^2$=Lunch 22$^2$; Green 22$^3$=Dinner 22$^3$; Blue 24$^4$=Bedtime 22$^4$; Purple 22$^5$=As needed 22$^5$.

Those skilled in the art, in light of the present teachings, will recognize that the color codes identifiable to a particular daily event may comprise a plurality of colors to accommodate a plurality of events in the particular patient's day. In addition, the designation of colors to a particular time of day can be specified by the individual user. The intent is consistency comparable with red=Stop and green=Go and yellow=slow down as implemented in traffic signals.

In another embodiment of the disclosure, the periodic daily events of the specific patient can include a chronologic arrangement of the following: 7:00 A.M.-9:00 A.M., 11:00 A.M.-1:00 P.M., Noon, 3:00 P.M.-5:00 P.M, 7:00 P.M.-9:00 P.M., 11:00 P.M.-Midnight, Midnight-6:00 A.M.

The divider wall 206 is preferably located along a central axis relative to the right side wall 216 and the left side wall 218 of the housing body 202 of the medicine management cabinet 200. With this arrangement the drawers 260 dimensioned having equal widths can easily be interchanged and inserted within any one of the formed first vertical open interior portion 204$^1$ or the second vertical open interior portion 204$^2$ of the open interior region 204 of the housing body 202. In another embodiment, the divider wall 206 can be positioned in any number of ways to accommodate a variety of drawer 260 widths. In another embodiment of the disclosure, the housing body 202 of the medicine management cabinet 200 can include at least two diving walls 206 to accommodate a variety of larger and smaller drawer 260 widths. In another embodiment the housing body does not include a divider wall 206, and, accordingly, the drawer 260 itself is used as a divider to divide the open interior region 204 into separate individual storage regions for medicine, pills, supplements, ampules 450, auxiliary articles.

In the exemplary embodiment, each of the drawers 260 are movable and/or removable from within the first open interior portion 204$^1$ and the second open interior portion 204$^2$ and, accordingly, the drawers 260 can be removed and placed on an external surface when the user, patient, caretaker, medical practitioner fills, refills the drawers with actual medicine product containers 190, auxiliary products 264, or to clean the drawers 260.

The space height selected between the drawers 260 may be selectively adapted based upon the height of the actual medicine product containers 190, for example, medicine bottles, pill bottles, supplemental bottles, vitamin bottles, ampules 450 and the like, to be stored within the drawers 260 allowing for head room for easy placement and removal of the medicine bottles, pill bottles, medicine, or supplemental bottles, ampules 450, and the like.

In the exemplary embodiment, each of the channeled mounting tracks 262 for receiving the base floor plane 274 of each of the drawers 260 is about ¼ inch deep, wherein the base floor plane 274 is adapted to a thickness of about slightly less than ¼ inch so that the drawers 260 can be easily slidable into the channeled mounting tracks 262. The drawers 260 are spaced apart a distance of a space height a distance between the top edge of the drawers.

The spacing dimensioned between the drawers 260, as disclosed above, is that of an exemplary embodiment, however, it should be understood that any spacing dimensioned between the drawers 260 accounting in for the height of the actual medicine product containers 190 to be contained therewithin the drawers 260 within the medicine management cabinet 200 can accomplish the objectives of the exemplary disclosure.

Many configurations are possible for the placement of the drawers 260 within the housing body 202 of the medicine management cabinet 200 including a variety of dimensions for the depth of the channeled mounting tracks 262, the spacing of the channeled mounting tracks 262, and, accordingly, the dimensions of the drawers 260. In addition, many configurations are possible for the drawers 260, including materials of manufacture including at least a ferromagnetic or magnetic element, and an anti-microbial element.

In the exemplary embodiment of the disclosure, the medicine cabinet is manufactured with custom plastic from materials with built-in antimicrobial and antibacterial properties that help to resist the growth of bacteria, mold, mildew, fungi, viruses and other microbes. For example, Ray Products thermoforms at http://www.rayplastics.com/antimicrobial-plastics-manufacturing/.

With reference to FIG. 29, the medicine management cabinet 200 includes one or more transferable malleable dividers 280 adapted for positioning within at least one of the plurality of drawers $260^{1-n}$ and operable for dividing of the drawers into two or more sections, section one 282 and second two 284 within one drawer 260 to store at least two different actual medicine products 180 for the periodic daily event 22 of the day as indicated on the periodic daily event label 72 removably attached on the raised front wall 276 of the drawer 260.

In this manner, the remote medicine exemplar container $30^r$ can be removably attached to a portion of the raised front wall 276 of each section of the drawer 260 to correctly identify the actual medicine product containers 190 stored therein each respective section of the drawer 260.

In an embodiment of the present disclosure, each of the drawers 260, can further include two opposing openings (not shown) on each of the right side wall 268 and the left side wall 270 of the drawer 260 for enabling carrying of the drawer 260 into and out from the medicine management cabinet 200. The user, patient, care giver, and/or medical practitioner can then place the drawer 260 on a surface when the user, patient, care giver, and/or medical practitioner fills or refills the medicine exemplar containers 30, and the actual medicine product daily organizer 400.

Each of the drawers 260 includes interior surfaces. The interior surfaces of the drawers 260 of the medicine management cabinet 200 can be covered with an anti-microbial material. In one embodiment, the anti-microbial material is an anti-microbial extrusion laminated reinforced film. This anti-microbial extrusion laminated reinforced film is available from Americover of Escondido, Calif. In another embodiment of the present disclosure any of the interior surfaces of the drawers 260 of the medicine manager cabinet 200 can be covered with the anti-microbial film.

As shown in FIG. 29, the medicine management cabinet 200 can include a portable miniature refrigeration unit 608 removably maintained in the open interior region 204 of the medicine management cabinet 200 for enabling selectively cooling of actual medicine products 180 stored therewithin. The portable miniature refrigeration unit 608 includes a locking latch which keeps cold the actual medicine products stored therewithin. The portable miniature refrigeration unit 608 operates on DC 12v or AC 110v. The portable miniature refrigeration unit 60 includes dimensions having a length of about 10.00 inches, having a width of about 7.00 inches, and a height of about 10.50 inches. Adaptors can are, also, included.

As shown in FIGS. 17-25 the medicine management cabinet 200 includes a holding means to allow a user to manipulate the medicine management cabinet 200. In addition, the medicine management cabinet 200 includes a transport means for enabling transport of the medicine management cabinet 200 by the user, patient or care giver or medical practitioner, from one place to another place. In the exemplary embodiment, the transport means are swivel wheels 308 to facilitate handling and transport by the user, patient or care giver or medical practitioner. In a preferred embodiment, the medicine management cabinet 200 includes a set of four swivel wheels 308 integrally attached to the exterior bottom floor plane 215 of the bottom floor plane 214 of the medicine management cabinet 200 adapted and operable so that the four swivel wheels are retractable.

In the exemplary embodiment the holding means is a retractable handle 306.

For enabling transport of the medicine management cabinet 200 by the user the retractable handle 306 is integrally machined within the top wall 212 of the medicine management cabinet 200 and one or more swivel wheels 308, preferably four swivel wheels 308 are individually attached to the bottom floor plane 214 of the medicine management cabinet 200 for enabling ease of movement of the medicine management cabinet 200 when the medicine management cabinet 200 is pulled via a retractable handle 306 by the user and stability of the medicine management cabinet 200 when the medicine management cabinet 200 is at a resting position.

The four swivel wheels 308 enable 360 degrees swiveling movement of each of the swivel wheels 308 and operable to turn the medicine management cabinet 200 in a 360 degrees direction.

In one embodiment of the present disclosure the retractable handle 306 is a retractable handle integrally machined into the top wall 212 of the medicine management cabinet 200 for enabling easy access to the retractable handle 306.

In another exemplary embodiment, the medicine management cabinet 200 includes a camera 500. The preinstalled camera 502 is implemented to record the patient and care giver who is opening and closing the medicine management cabinet 200 in real time.

As shown in FIGS. 30A-30B, 31 and 32, the medicine management and identification system 10 includes the actual medicine product daily organizer 400. In a preferred embodiment, the actual medicine product daily organizer 400 includes a daily dispensing time system bearing the viewing text of each day of the week, Sunday 424, Monday 426, Tuesday 428, Wednesday 430, Thursday 432, Friday 434, and the viewing texts$^{1-4}$ of the periodic daily events $22^{1-n}$ of the day as depicted on the periodic daily event tiles $124^{1-n}$ on the medicine management chart 200, namely, Breakfast $22^1$, Lunch $22^2$, Dinner $22^3$, and Bedtime $22^4$ wherein the each day of the week and each daily event is preprinted thereon a color shaded cubicle 92, and wherein each color shaded cubicle 92 is completely colored with the color 22 preselected to associate with the daily event of the day 22 that is preprinted thereon the cubicle 22.

The actual medicine product daily organizer 400 is configured to be implemented with the periodic daily event color-code sheet, the medicine manager chart 100 together with the medicine management cabinet 200.

As shown in FIGS. 30A-30B, a first row of the color shaded cubicles 92 bearing the viewing text$^1$ of the periodic daily event Breakfast $22^1$ are completely colored in the color 24 yellow $24^1$ forming a yellow Breakfast cubicle row $414^1$. A second row of the color shaded cubicles 92 bearing the viewing text$^2$ of the periodic daily event Lunch $22^2$ are completely colored in the color 24 orange $24^2$ forming an orange Lunch cubicle row $414^2$. A third row of the color shaded cubicles 92 bearing the viewing text$^3$ of the daily event Dinner $22^3$ are completely colored in the color 24 green $24^3$ forming a green Dinner cubicle row $414^3$. A fourth row of the color shaded cubicles 92 bearing the viewing text$^4$ of the daily event Bedtime $22^4$ is completely colored in the color 24 blue $24^4$ forming a blue Bedtime cubicle row $414^4$.

In this embodiment, the plurality of actual medicine products 180, pills or supplements prescribed for the specific patient by a medical practitioner stored in the medicine management cabinet 200 for use with the actual medicine product daily organizer 400 are readily identified by use of the medicine manager chart 100, and, more particularly, the exemplars 182 contained therewithin each medicine exemplar containers 30 and the associated information 184 provided in each of the Medicine/Supplement Exemplar tiles $126^{1-5}$ corresponding to each of the exemplars 182 contained on the medicine management chart 200 and the exemplars 182 contained within the remote medicine exemplar containers $30^r$ removably attached on the raised front walls 276 of the drawers 260 of the medicine management cabinet 200. The user, patient, caregiver, medicine practitioner can readily choose the correct actual medicine product 180 provided by the stock of actual medicine product containers 190 stored in the medicine management cabinet 200 by the user, patient, caregiver, medical practitioner viewing the exemplar 182 of the actual medicine product 180 contained therein the medicine exempler container 30 removably attached to the medicine management chart 100 and checking a second time by viewing the exemplar 182 contained in the remote medicine exemplar container $30^r$ and dispense the correct dosage 146 of the correct actual medicine product into each of the correct color shaded cubicles 92 at the correct periodic daily event of the day $22^{1-4}$ on each day of the seven days of the week over a period of time the specific patient is prescribed to take the actual medicine products 180.

The actual medicine product daily organizer 400, comprises a generally flat housing 98 including a uniform upwardly facing array of color shaded cubicles 92, each of the color shaded cubicles 92 includes an operable lid 94 opening to a cavity 95, the operable lid 94 adapted and operable for opening upwardly for receiving, containing, and removing of a dose of the actual medicine product 180 of the specific patient as discerned from the medicine management chart 100.

The actual medicine product daily organizer 400 includes the uniform upwardly facing array of different color shaded cubicles 92 arranged in columns $412^{1-n}$ and rows $414^{1-n}$. Each of the different color shaded cubicles 92 includes an operable lid 94 opening to a cavity 95, the operable lid 94 adapted and operable for opening upwardly for receiving, containing, and removing of a dose of the actual medicine product 180 pre-selected from the medicine regimen of the specific patient as discerned from the medicine management chart 100.

The rows of the different color shaded cubicles 92 are sufficient in number for receiving dosage 146 of the actual medicine products 180 at each of the different periodic daily events $22^{1-n}$ of the day are arrayed in the chronological arrangement as discerned from the medicine management chart 100 for each of seven days of a week arranged in columns over a preselected number of days.

The operable lid 94 is configured over the opening to the cavity 95 and pivotally attached to an upper marginal edge of the rear side 93 of each of the color shaded cubicles 92 wherein each operable lid 94 has an upwardly releasable locking means for selectively retaining each operable lid 94 in a closed position to contain each dosage 146 of the actual medicine product 180 within each of the color shaded cubicles 92.

Each of the operable lids 94 of the color shaded cubicles 92 bears a viewing text associated with the periodic daily event matrix of tiles $124^{1-n}$ within the medicine manager chart 200 having the same color 24 as the color shaded cubicle 92 and having the same color 24 as the periodic daily event label 72 having the same periodic daily event 22 printed thereon removably attached to a corresponding drawer 260 within the medicine management cabinet 200 advising of the proper sequence and timing of manually opening each of the operable lids 94 of the color shaded cubicles 92 to receive the dosage 146 actual medicine product 180 stored within the corresponding drawer 260, contain the actual medicine products 180, and gain access to the dosage of the actual medicine product 180.

The viewing text preprinted on each of the color shaded cubicles 92 includes the periodic daily event of the day $22^{1-n}$ associated with the color $24^{1-n}$ discerned by the medicine management chart 200, and the day of the week.

The generally flat housing of the actual medicine product daily organizer 400 is sized for slidably storing within the actual medicine product daily organizer mateable mounting storage container $248^1$ removably attached to the magnetic inside door 228 of the medicine management cabinet 200.

The actual medicine product daily organizer 400 is customized to include an array of color shaded cubicles 92 including the daily event of the day $22^{1-n}$ during each of the days of the week to be uniformly vertically arranged in columns 412 in chronological order.

In an exemplary embodiment, the actual medicine product daily organizer 400 includes an array of color coded cubicles 92 each dimensioned having the identical size, organized in columns $412^{1-n}$, wherein each column $412^{1-n}$ is headed by a consecutive day of the week, Sunday 424, Monday 426, Tuesday 428, Wednesday 430, Thursday 432, Friday 434, Saturday 436, having each column include the different color shaded cubicles 92 labelled with a preprinted viewing text of the consecutive days of the week Sunday 424, Monday 426, Tuesday 428, Wednesday 430, Thursday 432, Friday 434, Saturday 436 preprinted thereon, and bearing the viewing text of the periodic daily events of the day $22^{1-n}$, Breakfast $22^1$, Lunch $22^2$, Dinner $22^3$, Bedtime $22^4$, As Needed $22^5$, preprinted thereon each of the operable lids 94, and wherein each of the color shaded cubicles 92 and pivotally attached operable lid 94 is completely color shaded with the preselected color $24^{1-n}$ visually identified with the periodic daily event of the day $22^{1-n}$ at which time the medicine product 180 is to be dispensed to the specific patient.

As visually shown, the Sunday columns of different colored cubicles 424 of different color shaded cubicles 432 each bearing the viewing text Sunday 424 and each bearing the color $24^1$ and viewing text of the periodic daily event $22^{1-4}$ of the day in the chronological order depicted in the medicine management chart 100: a yellow $24^1$ color shaded cubicle 92 bearing the viewing text$^1$ Breakfast $22^1$, an orange $24^2$ color shaded cubicle 92 bearing the viewing text$^2$ Lunch $22^2$, a green $24^3$ color shaded cubicle 92 bearing the viewing text$^3$ Dinner $22^3$, a blue $24^4$ color shaded cubicle 92 bearing the viewing text Bedtime $22^4$, and a purple $24^5$ and bearing the viewing text As Needed $22^5$.

The Monday column of different color shaded cubicles 426 each bearing the viewing text Monday 426 and each bearing the viewing text of the periodic daily event $22^{1-5}$ of the day in the chronological order depicted in the medicine management chart 100: a yellow $24^1$ color shaded cubicle 92 bearing the viewing text$^1$ Breakfast $22^1$, an orange $24^2$ color shaded cubicle 92 bearing the viewing text$^2$ Lunch $22^2$, a green $24^3$ color shaded cubicle 92 bearing the viewing text$^3$ Dinner $22^3$, a blue $24^4$ color shaded cubicle 92 bearing the viewing text Bedtime $22^4$, and a purple $24^5$ and bearing the viewing text As Needed $22^5$.

The Tuesday column of different color shaded cubicles 428 each bearing the text Monday 426 and each bearing the viewing text of the periodic daily event $22^1$ of the day in the chronological order depicted in the medicine management chart 100: a yellow $24^1$ color shaded cubicle 92 bearing the viewing text$^1$ Breakfast $22^1$, an orange $24^2$ color shaded cubicle 92 bearing the viewing text$^2$ Lunch 22$^2$, a green 24$^3$ color shaded cubicle 92 bearing the viewing text$^3$ Dinner 22$^3$, a blue 24$^4$ color shaded cubicle 92 bearing the viewing text Bedtime 22$^4$, and a purple 24$^5$ and bearing the viewing text As Needed 22$^5$.

The Wednesday column of different color shaded cubicles 430 each bearing the viewing text Monday 426 and each bearing the viewing text of the periodic daily event 22$^{1-5}$ of the day in the chronological order depicted in the medicine management chart 100: a yellow 24$^1$ color shaded cubicle 92 bearing the viewing text$^1$ Breakfast 22$^1$, an orange 24$^2$ color shaded cubicle 92 bearing the viewing text$^2$ Lunch 22$^2$, a green 24$^3$ color shaded cubicle 92 bearing the viewing text$^3$ Dinner 22$^3$, a blue 24$^4$ color shaded cubicle 92 bearing the text Bedtime 22$^4$, and a purple 24$^5$ and bearing the viewing text As Needed 22$^5$.

The Thursday column of different color shaded cubicles 432 each bearing the viewing text Monday 426 and each bearing the viewing text of the periodic daily event 22$^{1-5}$ of the day in the chronological order depicted in the medicine management chart 100: a yellow 24$^1$ color shaded cubicle 92 bearing the viewing text$^1$ Breakfast 22$^1$, an orange 24$^2$ color shaded cubicle 92 bearing the viewing text$^2$ Lunch 22$^2$, a green 24$^3$ color shaded cubicle 92 bearing the text$^3$ Dinner 22$^3$, a blue 24$^4$ color shaded cubicle 92 bearing the viewing text Bedtime 22$^4$, and a purple 24$^5$ and bearing the viewing text As Needed 22$^5$.

The Friday column of different color shaded cubicles 434 each bearing the viewing text Monday 426 and each bearing the viewing text of the periodic daily event 22$^{1-5}$ of the day in the chronological order depicted in the medicine management chart 100: a yellow 24$^1$ color shaded cubicle 92 bearing the viewing text$^1$ Breakfast 22$^1$, an orange 24$^2$ color shaded cubicle 92 bearing the viewing text$^2$ Lunch 22$^2$, a green 24$^3$ color shaded cubicle 92 bearing the viewing text$^3$ Dinner 22$^3$, a blue 24$^4$ color shaded cubicle 92 bearing the viewing text Bedtime 22$^4$, and a purple 24$^5$ and bearing the viewing text As Needed 22$^5$.

The Saturday column of different color shaded cubicles 436 each bearing the viewing text Monday 426 and each bearing the viewing text of the periodic daily event 22$^{1-5}$ of the day in the chronological order depicted in the medicine management chart 100: a yellow 24$^1$ color shaded cubicle 92 bearing the viewing text$^1$ Breakfast 22$^1$, an orange 24$^2$ color shaded cubicle 92 bearing the viewing text$^2$ Lunch 22$^2$, a green 24$^3$ color shaded cubicle 92 bearing the viewing text$^3$ Dinner 22$^3$, a blue 24$^4$ color shaded cubicle 92 bearing the viewing text Bedtime 22$^4$, and a purple 24$^5$ and bearing the viewing text As Needed 22$^5$.

Figure 31:
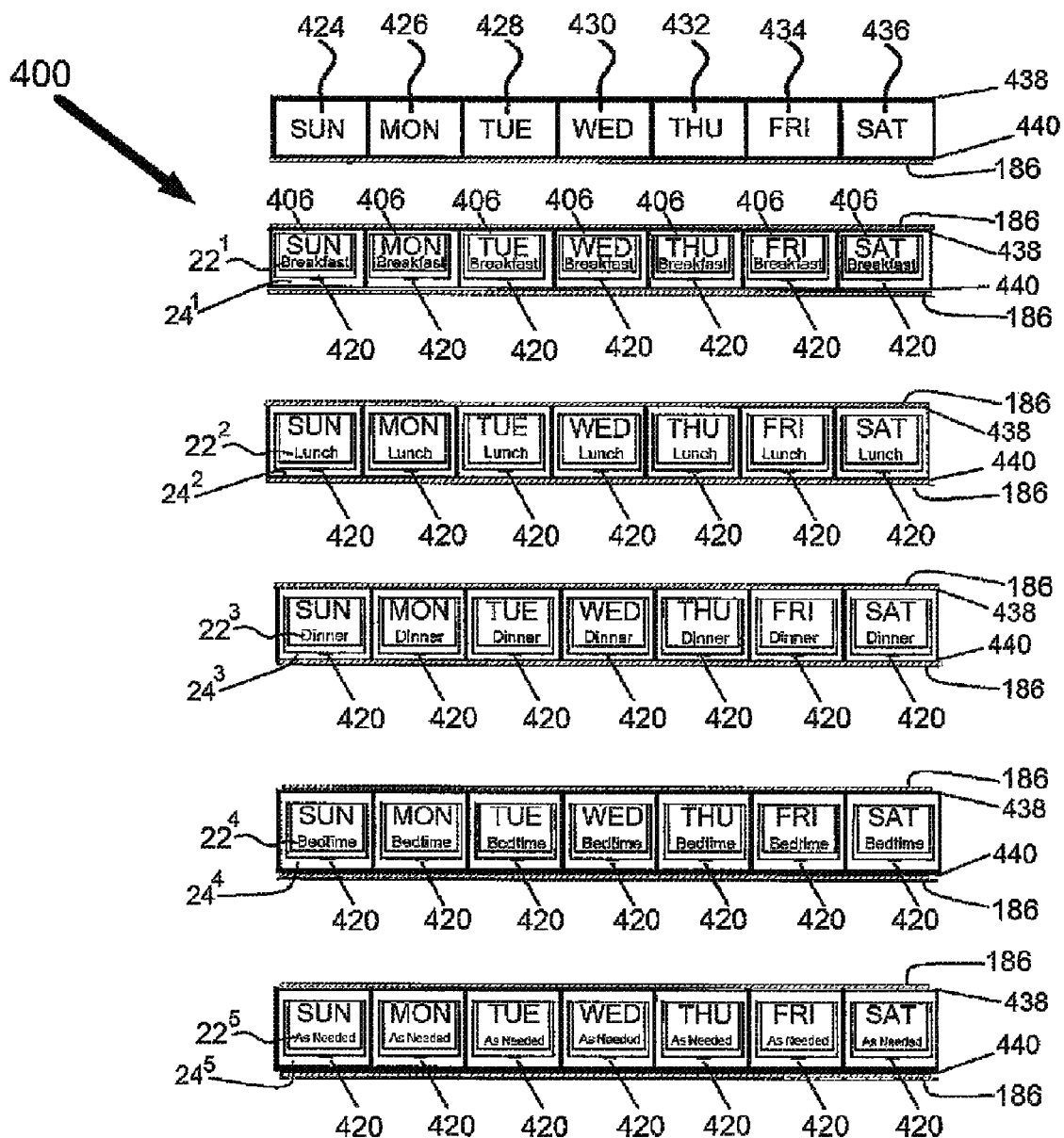
FIG. 31 is an exploded view of an actual medicine product daily organizer, according to an embodiment of the disclosure.

As shown in FIGS. 30A and 31, a first row of color coded cubicles 414$^1$ is completely color shaded in the color 24 yellow 24$^1$ bearing the viewing text$^1$ Breakfast 22$^1$ forming a row of yellow Breakfast cubicles 414$^1$ and each Breakfast 22$^1$ bearing the viewing text of each consecutive day of the week.

A second row of color shaded cubicles 414$^2$ is disposed adjacent and below to the row of the Breakfast row of yellow color shaded cubicles 414$^1$, wherein each of the row of color shaded cubicles is completely colored in the color 24 orange 24$^2$ bearing the viewing text$^2$ Lunch 22$^2$ forming a Lunch row of orange color shaded cubicles 414$^2$.

A third row of color shaded cubicles 414$^3$ is disposed adjacent and below to the row of Lunch cubicles 414$^2$, wherein the third row is completely colored in the color 24 green 24$^3$ bearing the viewing text$^3$ Dinner forming a Dinner row of green color shaded cubicles 414$^3$.

A fourth row of color coded cubicles 92$^4$ is disposed adjacent and below to the row of Dinner cubicles 414$^3$ wherein the fourth row is completely colored in the color 24 blue 24$^4$ bearing the text$^4$ Bedtime 22$^4$ forming a Bedtime row of blue color shaded cubicles 414$^4$.

In another embodiment of the present disclosure, a fifth row of color shaded cubicles 92$^5$ is disposed adjacent and below to the row of Bedtime cubicle 414$^4$ wherein the fifth row is completely colored in the color 24 purple 24$^5$ bearing the viewing text$^5$ As Needed forming an As Needed row of purple color shaded cubicles 414$^5$.

As shown in FIG. 31, each row, the Breakfast row of yellow color shaded cubicles 414$^1$, the Lunch row of orange color shaded cubicles 414$^2$, the Dinner row of green color shaded cubicles 92$^3$, the Bedtime row of blue color shaded cubicles 414$^4$, the As Needed row of purple color shaded cubicles 414$^5$, includes a mateable mounting magnet 186 on a top side 438 and a bottom side 440. Accordingly, each of the rows of color shaded cubicles, the Breakfast row of yellow color shaded cubicles 414$^1$, the Lunch row of orange color shaded cubicles 414$^2$, the Dinner row of green color shaded cubicles 92$^3$, the Bedtime row of blue color shaded cubicles 414$^4$, the As Needed row of purple color shaded cubicles 414$^5$, can be detached and removable attached in the chronological arrangement as depicted from the medicine management chart 100, including the chronological arrangement in vertical order Breakfast 22$^1$, Lunch 22$^2$, Dinner 22$^3$, Bedtime 22$^4$, As Needed 22$^5$. In this scenario each row of cubicles can be detached from each other and so that each of the rows of color shaded cubicles, 414$^{1-5}$ can be separately filled, refilled with dosages of actual medicine products, or when separate individual rows of color shaded cubicles are in use, or when the rows of color shaded cubicles need to be cleaned. Accordingly, if the user, patient, caregiver, medical practitioner wanted to fill and refill the Breakfast row of yellow color shaded cubicles 414$^1$ separated from the Lunch row of orange color shade cubicles 414$^2$ he/she may do so and thereby reduce chances of mistakenly placing the dosage 146 of actual medicine product 180 into the incorrect row of color coded cubicles 412.

In addition, the patient may need to carry the Breakfast row of yellow color shaded cubicles with him/her when the patient has an early Doctor appointment or needs to travel at Breakfast time.

Figure 32:
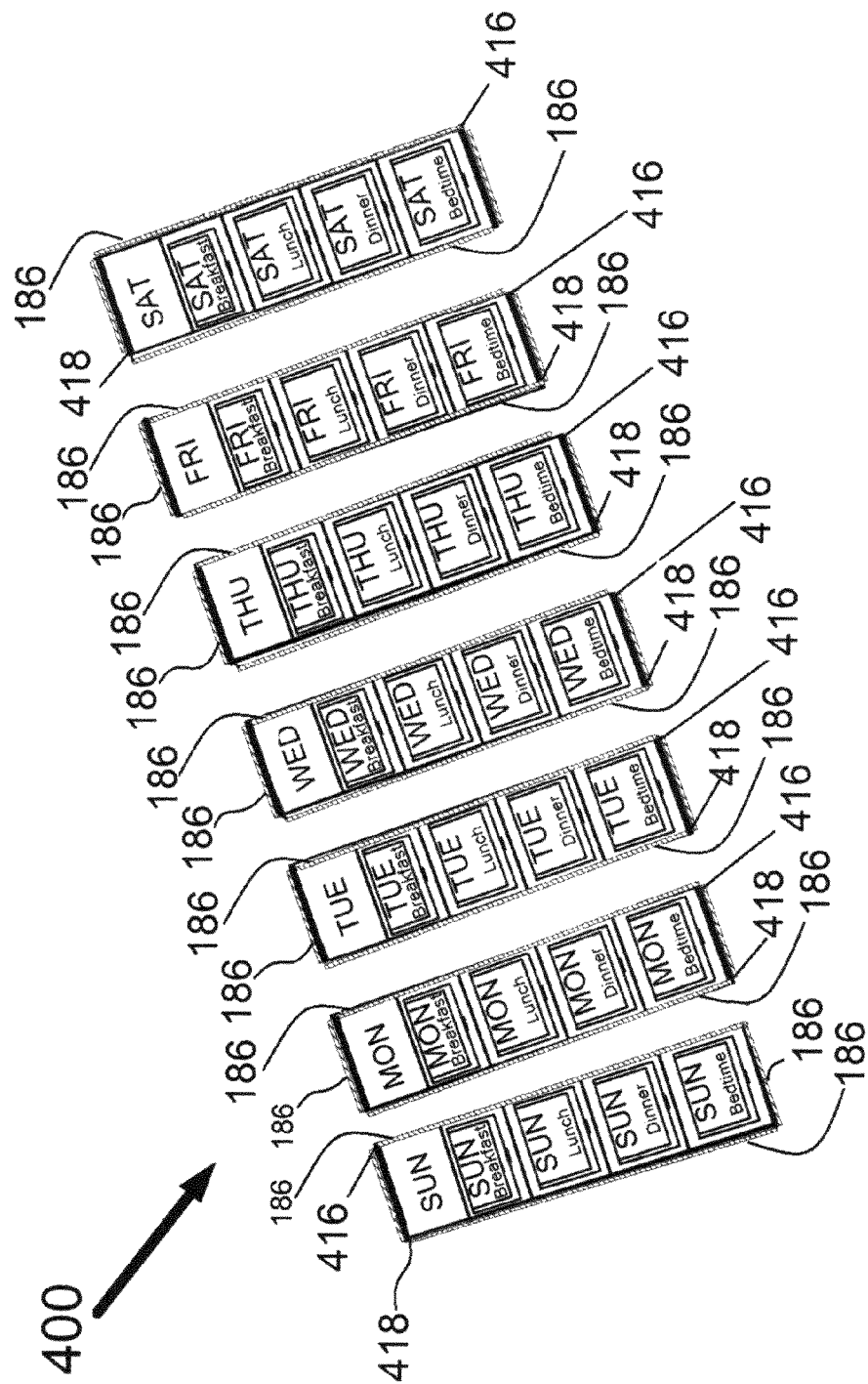
FIG. 32 is an exploded view of an actual medicine product daily organizer, according to an embodiment of the disclosure.

In addition, as shown in FIG. 32 each of the columns 412$^{1-7}$ includes a left side 416 and a right side 418. The first column 412$^1$ of the different color shaded cubicles 92 of Sunday 424 column of color shaded cubicles 424 includes a mateable mounting magnet 186 of the plurality of mateable mounting magnets 186 attached to the right side 416 and the left side 416. The second column 412$^2$ of different color shaded cubicles 92, the Monday 426 column of different color shaded cubicles 426 includes a mateable mounting magnet 186 on the left side 416 and the right side 418. The third column 412$^3$ of different color shaded cubicles 92, the Tuesday 428 column of different color shaded cubicles 428 includes a mateable mounting magnet 186 on the left side 416 and the right side 418. The fourth column 412$^4$ of different color shaded cubicles 92, the Wednesday 430 column of different color shaded cubicles 430 includes a mateable mounting magnet 186 on the left side 416 and the right side 418. The fifth column 412$^5$ of different color shaded cubicles 92, the Thursday 432 column of different color shaded cubicles 432 includes a mateable mounting magnet 186 on the left side 416 and the right side 418. The sixth column of different color shaded cubicles, the Friday 434 column of different color shaded cubicles 434 includes a mateable mounting magnet 186 on the left side 416 and the right side 418. A seventh column of different color shaded cubicles, the Saturday 436 column of different color shaded cubicles 436 of includes a mateable mounting magnet 186 on the left side 416 and the right side 418.

In this embodiment, the user, patient, family member, caregiver, medical practitioner can detach and removably attach any one of the columns of different color shaded cubicles of the actual medicine product daily organizer 400 to and from each of the other columns $412^{1-7}$. Accordingly, if the user, patient, caregiver, medical practitioner wanted to fill and refill the Sunday 424 column of different color shaded cubicles 424 separated from the Monday 426 column of different color shaded cubicles 426 he/she may do so and thereby reduce chances of mistakenly placing the dosage 146 of actual medicine product 180 into the incorrect day of the week column of cubicles.

In addition, the user, patient, caregiver, medical practitioner can separate each of the rows $412^{1-4}$ and columns $412^{1-7}$ of color shaded cubicles or a single color shaded cubicle 406 and place them separately into a mini-medicine management cabinet 700, as shown in FIGS. 35A-35D, as described below, or into any portable carry device. For example, when the user, patient caregiver, is traveling to a medical practitioner's office for a visit scheduled for a Monday 424 at the time of the periodic daily event of the day Lunch $22^2$, they can carry the dosages 146 for the Monday column $412^1$ of different color shaded cubicles 426, including the Breakfast $22^1$ cubicle 406, the Lunch $22^2$ cubicle 406, the Dinner $22^3$ cubicle 406, the Bedtime $22^4$ cubicle 406, and the As Needed $22^5$ cubical 406, with them and leave the remainder of the actual medicine product daily organizer 400 at home stored within the medicine management cabinet 200.

In addition, a mateable mounting magnet 186 is attached to a rear side 404 of the actual medicine product daily organizer 400 so that the actual medicine product daily organizer 400 can be removably attached to the magnetic inside door 228 or to the permanent exterior magnetic board 220.

Figure 33:
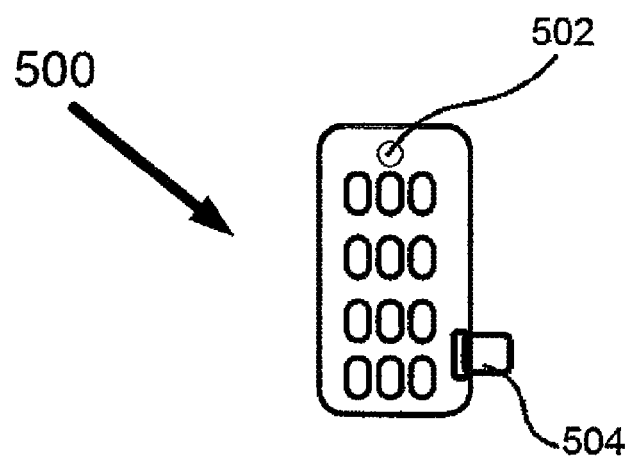
FIG. 33 is a front planar view of a mobile communication device, according to an embodiment of the disclosure.

When taking care of a patient with a long illness, it is known to many patient's and caretakers that it is easy to forget what the actual medicine products 180 look like, when they are prescribed to be administered, why, and at what time of the day, and often it is normal to forget due to the day to day stress, fears, and distractions parlayed from the inherent strength of the illness against the patient, user, family, caregiver. To solve this problem, an embodiment of the disclosure, provides the user, patient, caregiver, medicine practitioner with a mobile communication device 500, as shown in FIG. 33, for capturing and storing images 524 of the medicine management charts 100, the patient, over the duration of the illness for enabling a user, patient, caregiver, medical practitioner to store the images 524 capable of being retrieved and maneuvered to a printer to enable printing of the image or images 524 of the of the medicine management charts 100 of the specific patient, thereby keeping an up-to-date history of the medicine management charts 100 of the specific patient and prevent against mismanagement of multiple medications and incorrect administration of the actual medicine products 180 to the specific patient. It is exemplary practice to capture an image of the medicine management chart 100 before any changes are made to the medicine management chart 100 so that a current image 524 of the medicine management chart is maintained.

According to the exemplary embodiment of the disclosure, the medicine management and identification system includes a mobile communication device 500. The mobile communication device 500 includes a preinstalled camera 502 and a usb port to receive a usb flash drive 504. The mobile communication device 500 includes one or more computing devices. The one or more computing devices 510 includes one or more processes or microprocessors 512, configured to receive, identify, derive, store, data, from data input, memory, instructions 26, user interface, internal electronic display 520, external electronic display 522, data output, and other components typically present in general purpose computing devices. The data input including identification of the specific patient, identification of the medical practitioner of the specific patient, caregiver of the specific patient, date, year, one or more medicine management charts, periodic daily event color-code sheet, one or more images 524 of the medicine management chart identified by the date and the year. The mobile cell phone includes a preinstalled camera 502 for capturing a plurality of images of the medicine management chart.

As shown in FIGS. 1 and 33, a mobile communication device 500 provides medicine management and identification system 10 with a device to capture an image 524 of a current up-to-date medicine management chart 100. Accordingly, the image 524 of the medicine management chart 100 can be stored in a memory of the one or more processors of the mobile communication device 500 creating a historical medicine management chart 100 record for the specific patient that can be retrieved by the user, patient, family member, caregiver, medical practitioner for reference for the user, patient, family member, caregiver, medical practitioner as needed. In addition, the mobile communications device 500 can include a USB flash drive 504 for storing the images 524 and transporting the images 524 and data thereon to a medical practitioner or personal computer of the patient, family member, caregiver.

After the user, patient, caregiver, medical practitioner completes the medicine management chart 100 by placing the patient identification card 120 removably attached to the patient identification tile 104, placing the medical practitioner identification card 118 removably attached to the medical practitioner identification tile 102, removably attaching the medicine exemplar containers 30 onto the Medicine/Supplement Exemplar tiles $124^{1-n}$, removably attaching the Prescription/Supplements labels 142 onto the tiles Prescription/Supplements tiles $128^{1-5}$, removably attaching the What's this for? labels 82 onto the What's this for? tiles $130^{1-5}$, and displaying the medicine management chart 100 supported by the portable rigid magnetic board 40 against the medicine management cabinet 200 the user, patient, care giver, or medical practitioner, can take an image 524 of the medicine manager chart 100 by means of the mobile communication device 500 and, accordingly, the user, patient, care giver, medical practitioner, can save the image into the software of the a mobile communication device 500, creating a digital medical management chart 100 folder within a folder of the mobile communication device 500.

In another embodiment the user, patient, care giver, medical practitioner can print the image 524 creating a hard copy of the image 524 of the medicine management chart 100.

In an aspect of the embodiment of the disclosure, the image 524 of the medical management chart 100 is taken and printed immediately after the medicine management chart 100 is completed for the specific patient or immediately prior to the time any changes are made to the medicine manager chart 100. The printed image 524 of the medicine manager chart 100 is then stored in the medicine management notebook 600 by placing the printed images 524 in chronological order in the medical management notebook 600, and record the hard copy of the image by placing it chronologically into the medicine management notebook 600. The medicine management notebook 600 is a storage device for receiving, storing, and retrieving a printed image 604 of the image 524 of the medicine management chart 100.

Those skilled in the art, in light of the present teachings, will recognize that the mobile communication device 500 including the computing device 510 includes the internal electronic display 520 and the external electronic display 522 for showing real time and images 524 of the medicine management charts 100.

In addition, an auditory application including a voice application can be implemented to sound or speak at the pre-scheduled time the particular prescribed medicine is to be dispensed to the patient. In another exemplary embodiment a visual application can be implemented to trigger a light at the pre-schedule time the particular prescribed medicine is to be dispensed to the patient.

The data input can be implemented to allow the user to input the medicine manager identification record along with a real time input of the date and time of the medical identification record, the dosage of the prescribed medicine relating to the specific medicine identification container storing the exemplar of the specific prescribed medicine, warnings about the medicine, and the particular reactions the patient may have had to that specific prescribed medicine contained in the medicine identification container.

Accordingly, the patient, care giver, and medical practitioner can access the computer application of the medical manager identification chart through a private server or a commercially available medical terminal provided by the medical facility within which the patient and the medical practitioner can exchange information regarding the medicine manager identification chart for a particular patient.

Figure 34:
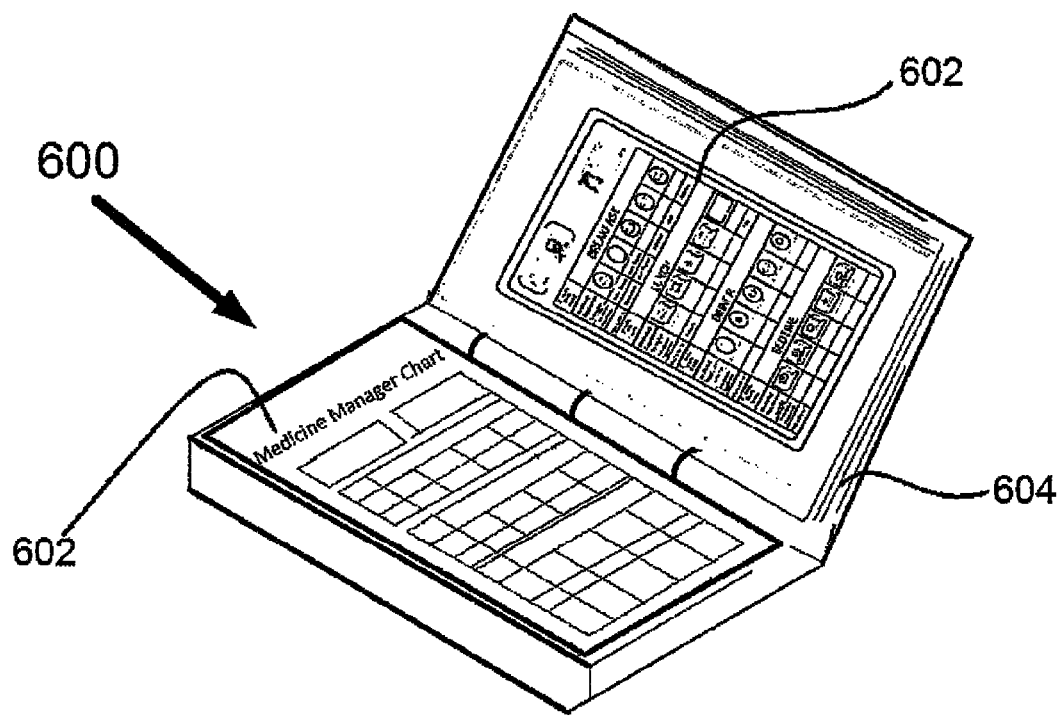
FIG. 34 is a perspective view of a medicine management notebook, according to an embodiment of the disclosure.
Figure 36A:
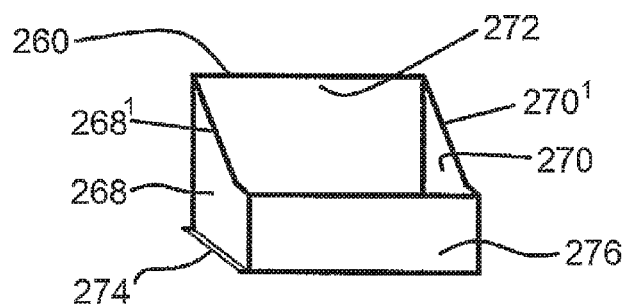
FIG. 36A is a side perspective view of a drawer, according to an embodiment of the disclosure.
Figure 36B:
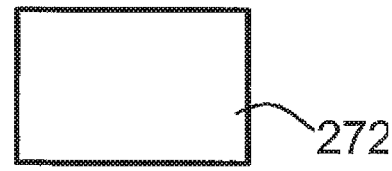
FIG. 36B is a rear perspective view of the drawer of FIG. 36A, according to an embodiment of the disclosure.
Figure 36C:
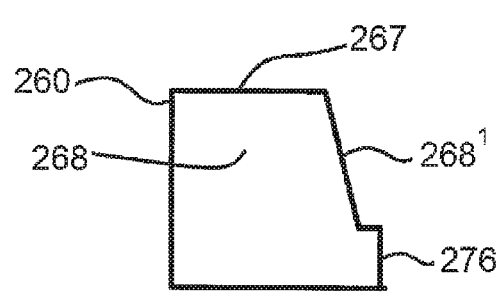
FIG. 36C is a right side view of the drawer shown in FIG. 36A, according to an embodiment of the disclosure.
Figure 36D:
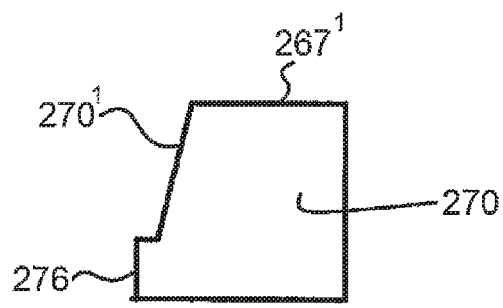
FIG. 36D is a left side view of the drawer shown in FIG. 36A, according to an embodiment of the disclosure.

A medicine management notebook 600 is provided in the medicine management and identification system 10 as shown in FIG. 1 and, more particularly in FIG. 34 to maintain and archive a historical record of the specific patient's medicine management charts 100. In an embodiment of the disclosure, the medicine management notebook 600 includes a medicine management binder 600 adapted to hold a plurality of printed image 604 of each of the plurality of medicine management charts 100 taken of the medicine management chart 100 at a time prior to any changes made or after any changes have been made to the medicine management chart 100 so that the user, patient, caregiver, family member, medicine practitioner has a current up-to-date record and a historical record of medicine management charts 100 of the specific patient during the course of his/her illness for the user, patient, caregiver, medical practitioner to reference.

In this manner, either by use of the mobile communications device's 500 computing devices or the medicine management notebook, the user patient, caretaker, medicine practitioner has a record of pre-stored medicine management charts 100 for the specific patient which the user, patient, caretaker, medical practitioner can have ready access to at the patient's home and to take with the patient to the medical practitioner's office. More importantly, the user, patient, caregiver, medical practitioner has an accurate record of what medications performed optimally for the specific patient and at what periodic daily event of the day so that the medical practitioner can align the specific patient's medicine regimen as indicated by the prior medicine management chart 100 records.

In this manner, the user, the patient, the care giver, retains a record of the exemplars 182 of the actual medicine products 186 prescribed in the medicine regimen, the associated information 184 including the prescription name 144, or generic name, dosage 146, mode of administration 146, adverse effects 150, periodic daily event $22^{1-5}$ of the day of the time the actual medicine product 180 was administered, what it was prescribed for the specific patient identified on the medicine management chart 100, for a particular date or range of dates as that recorded on the image of the medicine manager chart 100 by the medical practitioner identified on the medicine manager chart 100, the dosage 146, and the particular medicine as indicated by the exemplar 182 of the actual medicine product 180 contained in the medicine exemplar container 30.

In the event of a change in the prescription of the medicine regimen for the specific patient, the user, patient, care giver, and/or medical practitioner can amend the associated information 184 including changing the exemplar 182 within the medicine exemplar container 30 removably attached on the Medicine/Supplement Exemplar tiles $126^{1-5}$ of the medicine management chart 100 and the corresponding drawer 260 within the medicine management cabinet 200 with the updated exemplar 182 of the newly prescribed actual medicine product 180, and, accordingly, change the associated information 184 on the Prescription/Supplements labels and removably attaching the updated Prescription/Supplements labels 142 onto the Prescription/Supplements tiles $128^{1-5}$, change the associated information 184 on the What's this for? labels and removably attaching the updated What's this for? labels 82 onto the What's this for? tiles $130^{1-n}$, and can take the image 524 of the updated medicine manager chart 100, and save the current image 524, accordingly, digitally in the computing device 510 of the mobile communication device 500, or print the current image 524 hard copy and placing patient's medical management notebook 600.

In this manner, the user, patient, care giver, and/or medical practitioner has a historical record to which the user, patient, care giver, and/or medical practitioner can make reference to and retrieve necessary associated information 184 regarding the medicine management and identification of the medicine regimen of the specific patient.

This step of taking the current image 524 of the medicine management chart 100 is an important feature of the medicine management system 10 because once the user, patient, care giver, and/or medical practitioner amends and removes the previous exemplar 182 and the associated information 184 of the former prescribed actual medicine product 180 from the medicine management chart 100, the exemplar 182 is discarded and the associated information 184 is discarded and disappears. Thus, the contents of the removed and discarded information depends on the memory of the user, patient, care giver, and/or medical practitioner. Thus by taking an image 524 of the medicine manager chart 100 before any changes are made to it, the user, patient, care giver, and/or medical practitioner now has created a permanent image 524 and historical record of the medicine management charts 100 for the specific patient.

In the exemplary embodiment, the medicine management cabinet 200 can have many different dimensions and shapes. FIGS. 21-22 shows the exemplary embodiment of the medicine management cabinet 200 having a generally trapezoid shape.

Figure 37:
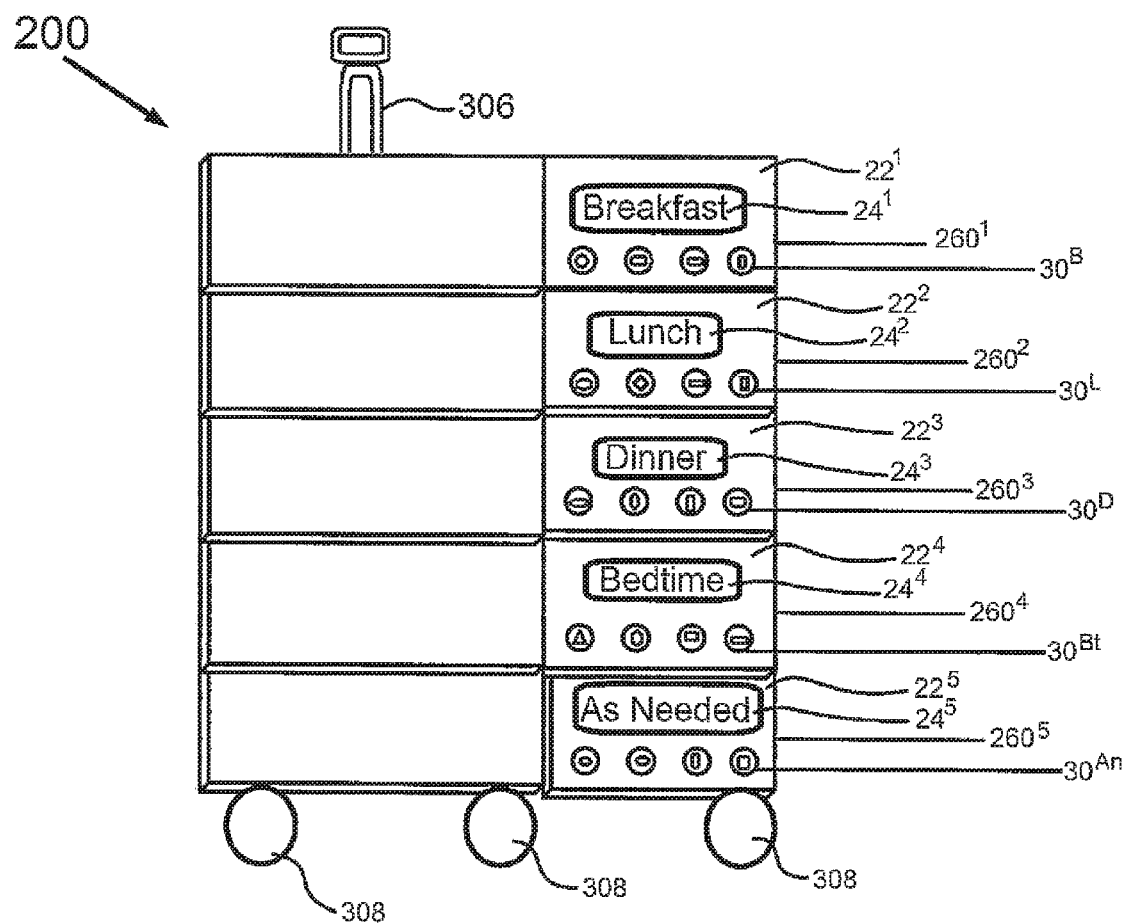
FIG. 37 is a perspective view of pivoting drawers within an open region section of a medicine management cabinet, according to an embodiment of the disclosure.

As shown in FIG. 37, in one embodiment of the disclosure, the medicine management cabinet 200 includes drawers 260 that can pivotally open from a side rail 271 of the medicine management cabinet 200.

The medicine management and identification system 10 wherein the medicine management cabinet 200 includes the generally trapezoidal shape is configured including the following dimensions. The door 222 configured having a length ($L^1$) of about 23.00 inches, a width ($W^1$) of about 17.00 inches, and a thickness ($T^1$) of about ½ inch. The left side wall 218 and the right side wall 216 each configured with identical dimensions having a bottom base$_1$ of about 14½ inches, a top base$_2$ of about 11.00 inches, and a height ($H^1$) of about 23⅞ inches. The closed exterior back wall 210 is configured with a length ($L^2$) of about 23¾ inches, a width ($W^2$) of about 18.00 inches, and a thickness of ($T^2$) of about ¾ inch. The top wall 212 is configured with a length ($L^3$) 19½ inches, a width ($W^3$) of about 12.00 inches, and having the thickness ($T^2$) of about ¾ inch. The open storage pocket 300 configured having the length ($L^1$) of about 23.00 inches, and the width ($W^2$) of about 18.00 inches, and having a slot opening width ($W^4$) of about 1½ inches.

The medicine management cabinet 200 having generally a trapezoid shape includes one or more top drawers 260 wherein, the one or more top drawers 260 each including the upstanding right side wall 268 and the upstanding left side wall 270 each having a height ($H^2$) of about 3⅝ inches, a right top edge 267$^1$ and a left top edge 267$^1$ having a width ($W^5$) of about 3⅞ inches, and a right bottom edge 269$^1$ and a left bottom edge 269$^2$ each having a width ($W^6$) of about 5⅝ inches; the upstanding rear wall 272 having the height ($H^2$) of about 3⅝ inches and a length ($L^4$) of about 8⅛ inches; the base floor plane 274 having a length ($L^5$) of about 8⅝ inches and the width ($W^8$) of about 5⅝ inches; the raised front wall 276 includes the length ($L^4$) of about 8⅛ inches, having a height ($H^3$) of about 1⅜ inches so that a right front edge 268$^1$ of the upstanding right side wall 268 and a left front edge 268$^2$ of the upstanding left side wall 270 are each configured having an identical slope $S^1$.

The medicine management cabinet 200 having generally the trapezoid shape, also, includes one or more middle drawers 260, including the upstanding right side wall 268 and the upstanding left side wall 270 each having the height ($H^2$) of about 3⅝ inches; the upstanding right side wall 268 having the right top edge 267$^1$ having a width ($W^7$) of about 6.00 inches, and the right bottom edge 269$^1$ having a width ($W^8$) of about 7½ inches; the upstanding left side wall 270 having the left top edge 267$^2$ having the width ($W^7$) of about 6.00 inches, and the left bottom edge 269$^2$ having the width ($W^8$) of about 7½ inches; the upstanding rear wall 272 having the height ($H^2$) of about 3⅝ inches, and the length ($L^4$) of about 8⅛ inches; the base floor plane 274 having the length ($L^4$) of about 8⅝ inches, and the width ($W^8$) of about 7½ inches; the raised front wall 276 includes the length ($L^4$) of about 8⅛ inches, and the height ($H^3$) of about 1½ inches so that the right front edge 268$^1$ of the upstanding right side wall 272 and the left front edge 268$^2$ of the upstanding left side wall 270 are each configured having the identical slope $S^1$.

The medicine management cabinet 200 having generally the trapezoid shape, also, includes one or more bottom drawers 260, including, the upstanding right side wall 268 and the upstanding left side wall 270 each having the height ($H^2$) of about 3⅝ inches; the upstanding right side wall 268 having the right top edge 267$^1$ having a width (W) of about 7⅞ inches, and the right bottom edge 269$^1$ having the width ($W^{10}$) of about 9.00 inches; the upstanding left side wall 270 having the left top edge 267$^2$ having the width ($W^9$) of about 7⅞ inches, and the left bottom edge 269$^2$ having the width ($W^{10}$) of about 9.00 inches; the upstanding rear wall 272 having the height ($H^2$) of about 3⅝ inches, and the length ($L^4$) of about 8⅛ inches; the base floor plane 274 having the length ($L^5$) of about 8⅝ inches, and the width ($W^8$) of about 7½ inches; the raised front wall 276 includes the length ($L^4$) of about 8⅛ inches, and the height ($H^3$) of about 1½ inches so that the right front edge 268$^1$ of the upstanding right side wall 268 and the left front edge 268$^2$ of the upstanding left side wall 270 are each configured having the identical slope $S^1$.

Each of the drawers 260 of the medicine management cabinet 100 having generally a trapezoid shape are configured having the raised front wall 276 having the height ($H^3$) of about 1½ inches for enabling easy access to the actual medicine products 180 and the plurality of auxiliary products 264 stored within each of the drawers 260.

Each of the channeled mounting tracks 262 within the medicine management cabinet 200 integrally machined into the first side 206$^1$ of the divider wall 206 and the right side wall 216 of the medicine management cabinet 200, and the second side 206$^2$ of the divider wall 206 and the left side wall 218 of the medicine management cabinet 200 has a width ($W^8$) of about 3/16 inches and a depth ($D^4$) of about ¼ inch adapted and operable to receive the base floor plane 274. The at least two hinges 234, each hinge 234 is about 2.00 inches by 1½ inches hinge 234.

The medicine management and identification system 10, according an embodiment of the disclosure includes the medicine management cabinet 200 configured having dimensions including a generally rectangular shape, wherein the medicine management cabinet 200 further includes the following dimensions: the door 222 configured with a length ($L^{100}$) of about 23.00 inches, a width ($W^{100}$) of about 17.00 inches, and a thickness ($T^{100}$) of about ½ inch. The top wall 212 configured with a width ($W^{200}$) of about 18.00 inches, having a length ($L^{200}$) of about 11¾ inches, and the thickness ($T^{200}$) of about ¾ inch. The left side wall 218 of the medicine management cabinet 200, and the right side wall 216 each configured with the length ($L^{100}$) of about 23.00 inches, a width ($W^{300}$) of about 9½ inches, and the thickness ($T^{100}$) of about ½ inch. The closed exterior back wall 210 is configured with a length ($L^{400}$) of about 23¾ inches, a width ($W^{400}$) of about 17⅜ inches, and the thickness of ($T^{100}$) of about ½ inch. The bottom floor plane 214 is configured with the width ($W^{400}$) of about 17⅜ inches and a length ($L^{500}$) of about 9½ inches, and the thickness ($T^{100}$) of about ½ inch. The open storage pocket 300 is configured with a length ($L^5$) of about 22.00 inches, the width ($W^{400}$) of about 17⅜ inches, and having a slot opening width (WV) of about 1½ inches.

The one or more drawers of the medicine cabinet 200 having in general a rectangular shape, wherein each of the drawers 260 includes the upstanding right side wall 268 and the upstanding left side wall 270, the upstanding right side wall 268 and the upstanding left side wall 270 each having a height ($H^{101}$) of about 3¾ inches, the upstanding right side wall 268 has a right top edge 267$^1$ having a width ($W^{101}$) of about 4¾ inches and a right bottom edge 269$^1$ having a width ($W^{201}$) of about 6½ inches. The upstanding left side wall 270 has a left right top edge 267$^2$ having the width ($W^{101}$) of about 4¾ inches and the left bottom edge 269$^1$ having the width ($W^{200}$) of about 6½ inches. Each of the upstanding right side wall 268 and the upstanding left side wall 270 has a front edge, a right front edge 268$^1$ and a left front edge 268$^2$, respectively. The upstanding rear wall 272 has the height ($H^{101}$) of about 3¾ inches, a length ($L^{101}$) of about 7¾ inches, wherein the base floor plane 274 includes a length ($L^{201}$) of about 8¼ inches and a thickness slightly less than ¼ inch. The raised front wall includes the length ($L^{101}$) of about 7¾ inches, and a height ($H^{201}$) of about 1⅝ inches so that the right front edge of the upstanding right side wall and the left front edge of the upstanding left side wall are each configured having an identical slope $S^1$. The at least two hinges 234, each hinge 234 is a 2 inches by 1½ inches hinge.

The medicine management cabinet 200 includes a first mateable mounting storage container 248$^1$ removably attached to the magnetic inside door 228 is configured with a height of about 4¼ inches, a width of about 10.00 inches, and an opening of about 1½ inches. The first mateable mounting storage container 248$^1$, is, also, referred to as the actual medicine product daily organizer mateable mounting storage container 248$^1$ because it houses the actual medicine product daily organizer 400.

The second mateable mounting storage container 248$^2$ is configured with a height of about 8¾ inches and a width of about 10½ inches, and an opening of about 1½ inches. The second mateable mounting storage container 248$^2$ is, also, referred to the medical records mateable mounting container 248$^2$ because it houses the specific patient's medical records and documents.

The third mateable mounting storage container 248$^3$ is configured with a height of about 3⅜ inches, a width of about 4½ inches, and an opening of about 1¾ inches. The fourth mateable mounting container 248$^3$ is configured with a height of about 5½ inches, a width of about 3½ inches, and an opening of about 1½ inches. The fifth mateable mounting container 248$^5$ is configured with a height of about 4.00 inches, a width of about 5¾ inches, and having an opening ($O^4$) of about 1½ inches.

In another embodiment of the subject matter of the medicine management and identification system 10, the medicine management and identification system 10 includes the medicine manager cabinet 200 that is smaller than the medicine management cabinets 200 described above. The medicine management cabinet 200 can be a mini-medicine management cabinet 700, as shown in FIGS. 35A-35D wherein the mini-medicine management cabinet 700 includes non-rigid walls having generally a rectangular shape. In this exemplary embodiment the transport means is a strap 716. The strap 716 is manufactured from a soft material forming a strap 716. The strap 716 is removably attached to the mini-medicine management cabinet 700 and can be placed over the shoulder or cross body of the user, patient, caregiver, medicine practitioner, to allow easy carrying and transport of the cabinet.

For the purpose of consistency and clarity, the same like numbers will be used to identify features of the mini-medicine management cabinet 700 with reference to the medicine management cabinet 200 as previously described, above.

The mini-medicine management cabinet 700 is portable and capable of being carried by means of a cross-body strap or strap 716. The portable mini-medicine management cabinet 700 includes non-rigid walls having a generally rectangular shape. The mini-medicine management cabinet 700 further, comprises the housing body 202 cabining the open interior region 204 having the door 222 to selectively open and close the open interior region 204. The door 22 is configured with a length ($L^{301}$) of about 12½ inches, a width ($W^{301}$) of about 14¼ inches, and a thickness ($T^{301}$) of about ¼ inch; the left side wall 218 and the right side wall configured 216 each with the length ($L^{301}$) of about 12½ inches, a width ($W^{302}$) of about 4¼ inches, and the thickness ($T^{301}$) of about ¼ inch; the closed exterior back wall 210 configured with the length ($L^{301}$) of about 12¼ inches, the width ($W^{301}$) of about 14¼ inches, and the thickness of ($T^{301}$) of about ¼ inch; the top wall 212 configured with the width ($W^{301}$) of about 14¼ inches, a length ($L^{302}$) of about 4¼ inches, a thickness ($T^1$) of about ¼ inch; the open storage pocket 300 configured with a length ($L^{303}$) of about 12.00 inches, a width ($W^{303}$) of about 14.00 inches and having the slot opening having a width ($W^{304}$) of about 1½ inches.

The open storage pocket 300 is configured to contain the medicine management chart 100 configured with a length of about 11.00 inches and a width of about 8.00 inches for convenience of transport.

The mini-medicine management cabinet 700 includes the Breakfast drawer 260$^1$, the Lunch drawer 260$^2$, the Dinner drawer 260$^3$, the Bedtime drawer 260$^4$, the As Needed drawer 260$^5$, as shown in FIGS. 35A-35D.

The open interior region 204 is configured with a length ($L^3$) of about 13½ inches, a width of about ($W^2$) 14.00 inches, and a depth of about 3¾ inches. The divider wall 206 is configured with a length ($L^3$) slightly less than 13½ inches, and a width ($W^4$) of about 10¼ inch.

The magnetic inside door 228 is configured with a length of about 13½ inches and having a width of about 14.00 inches that is flush with the back planar surface of the inside door 226.

In an embodiment of the disclosure, the one or more mateable mounting storage containers can be configured with a height ($H^{301}$) of about 5½ inches, a width ($W^{304}$) of about 6¼ inches, and an opening ($O^{301}$) having a depth (($D^{301}$) of about 1½ inches.

In another embodiment of the disclosure, the first mateable mounting storage container 248$^1$ is configured with a height (H) of about 5.00 inches, a width of about 11¼ inches, and an opening ($O^1$) having a depth ($D^1$) of about 1½ inches. The second mateable mounting storage container 248$^2$ is configured with a height (H) of about 8.00 inches, a width of about 11¼ inches; and an opening ($O^2$) having a depth ($D^3$) of about 1¾ inches. The third mateable mounting storage container 248$^3$ is configured with a height (H) of about 4.00 inches, a width of about 2½ inches, and an opening ($O^1$) having a depth ($D^1$) of about 1½ inches. The fourth mateable mounting storage container 248$^4$ is configured with a height (H) of about 4.00 inches, a width of about 2½ inches, and an opening ($O^1$) having a depth ($D^1$) of about 1½ inches. The fifth mateable mounting storage container 248$^5$ is configured with a height (H) of about 4.00 inches, a width of about 2½ inches, and an opening ($O^1$) having a depth ($D^1$) of about 1½ inches.

The mounting means for each of the mateable mounting storage containers 248 is a mateable mounting magnet attached to the mateable mounting storage container 248.

In another embodiment each of the mateable mounting storage containers 248 is manufactured with a ferrous material that is capable or removable attaching to the magnetic inside door 228 of the mini-medicine management cabinet 700.

In one embodiment of the mini-medicine management cabinet 700 having a medicine management cabinet with non-rigid walls, wherein each drawer 260 of the one or more drawers 260 including the upstanding rear wall 272 with a height ($H^{400}$) of about 3¾ inches, having a width ($W^{500}$) of about 6.00 inches, a raised front wall having the height ($H^{400}$) of about 3¾ inches, and the upstanding right side wall 268 with the height ($H^{400}$) of about 3¾ inches and having a width ($W^{501}$) of about 2.00 inches, and the upstanding left side wall 270 having the height ($H^{400}$) of about 3¾ inches having the width ($W^{501}$) of about 2.00 inches.

In the exemplary embodiment of the disclosure, the mounting means for the drawers 260 of the mini-medicine management cabinet is a mateable mounting magnet 30 of the plurality of mateable mounting magnets 30 attached to the drawer 260 and to a region of the closed interior back wall 208 of the mini-medicine management cabinet 700. The mounting means for the drawers 260 can be a mateable mounting magnet, or a hook and loop means.

The locking means 246 of the mini-medicine management cabinet 700 is adapted and operable for selectively opening and closing the door. The preferred locking means is a zipper 708 attached along the peripheral edges of the door 222 and the closed exterior back wall 210.

In this exemplary embodiment, the cabinet is manufactured using a material that is soft and resilient. The material can be any one of the following materials, canvas, leather, suede, malleable plastic, rigid plastic, nylon, polyester and any combination thereof.

In yet another embodiment, the mini-medicine management cabinet 700 is adapted to maintain one or more drawers 260. This exemplary embodiment can be implemented when a user, patient, caregiver travels to the medical practitioner's office during a particular event of the day, for example, "Lunch" 22² and, accordingly, the user can removably attach the Lunch drawer 260² within the mini-medicine manager cabinet 700 wherein the Lunch drawer 260² can contain the actual medicine products, and the first mateable mounting container 248¹, referred to as the actual medicine product daily organizer container 248¹, can contain therewith the row of orange Lunch cubicles 414² of the actual medicine product daily organizer 400 containing the dosage of actual medicine products that are specified to be taken at "Lunch" depicted in the medicine management chart 100 a copy of which is stored in the medicine management notebook which can be stored in the For example, the drawer labelled "Lunch" can include at least one medicine container including a container removably attached to the raised front wall of the drawer including an exemplar of the medicine within the medicine bottle stored in the drawer to be taken by the patient at "Lunch". In addition, the door can include the actual periodic medicine daily organizer 400 contained in the mateable mounting storage container 248, the patient's specific documents required at the medical clinician's visit, and a pill cutter to cut the pill when a half of the pill to be taken is prescribed for the patient.

Figure 38:
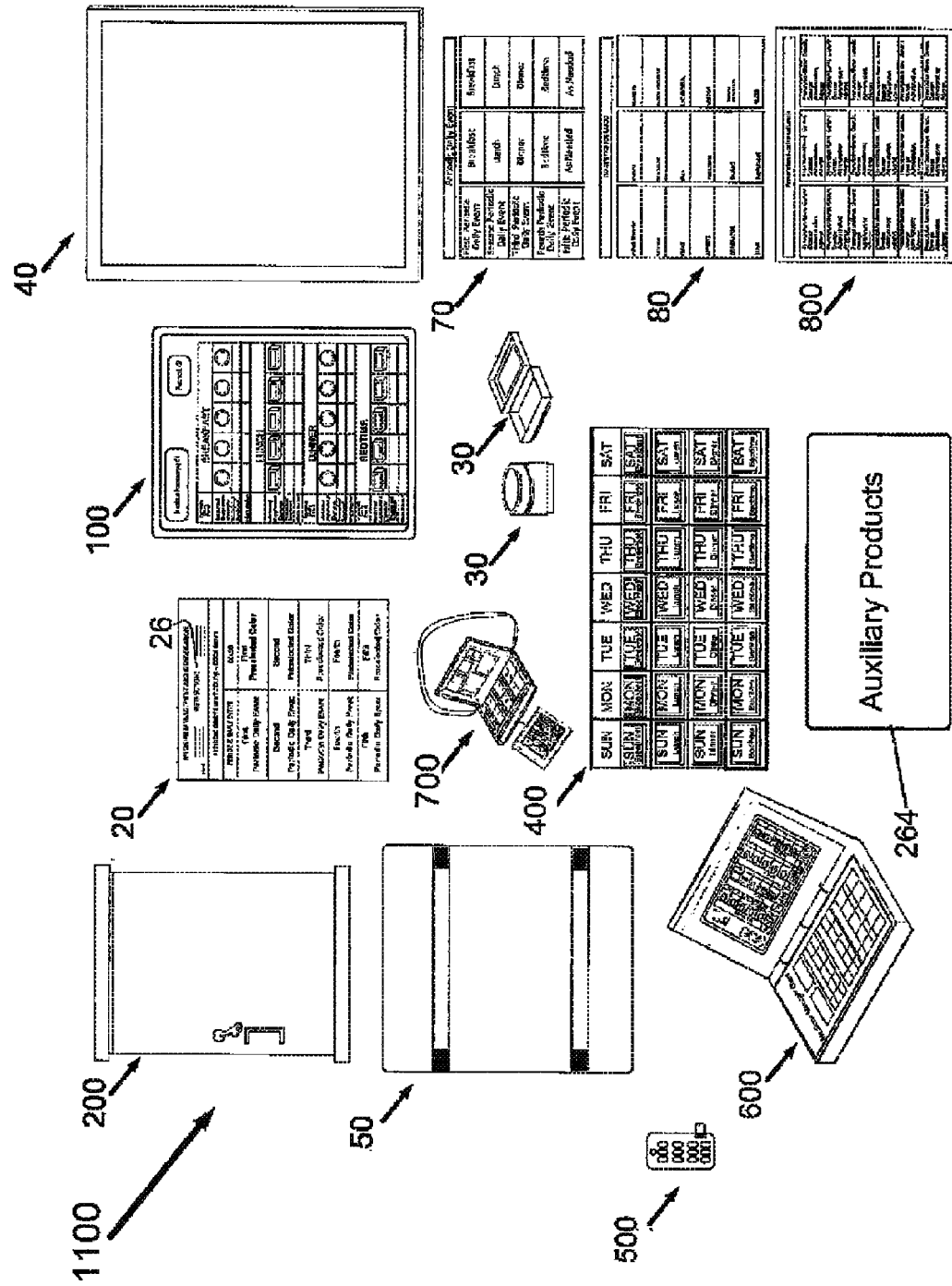
FIG. 38 is a perspective view of a medicine management and identification kit, according to an embodiment of the disclosure.

In an embodiment of the disclosure, the subject matter is embodied in a medicine management and identification kit 1100, as shown in FIG. 38. The medicine management and identification kit 1100 shows like numbers identifying like components and features of the medicine as used in the FIGS. 1-37 for continuity of the subject matter of the embodiment. The medicine management and identification kit 1100 comprising: a periodic daily event color-code sheet 20 with instructions 26, for instructing the user, patient, family member, care giver, medical practitioner in the implementation of a medicine management and identification system 10; one or more sheets of periodic daily event of the day labels 70; one or more sheets of Prescription/Supplements labels 800; one or more sheets of What's this for? labels 80; the medicine management and identification system 10, comprising a portable rigid magnetic board 40; a plurality of medicine exemplar containers 30; one or more medicine management charts 100; a medicine management cabinet 200; a mounting platform 50; an actual medicine product daily organizer 400; a mobile communications device 500; a medicine management notebook 600; each of which are described in more detail above, with reference to FIGS. 1-34 and thereby not repeated here for brevity sake.

The medicine management and identification kit 1000, further comprises, some of which are shown in FIG. 38, a portable refrigeration unit 608, a mini-medicine management cabinet 700, a plurality of band aides; an antiseptic tincture; an eye dropper; a syringe 316; a pill cutter; a measuring spoon 316; an ampule cutter 324; an ampule 322, a pair of magnifying glasses 319; a mirror 320, a bottle of aspirin; an epi-pen; a comb; a tooth brush, antiseptic-wipes; disposable wipes; digital thermometer; and scissors 318.

In an embodiment of the disclosure, the subject matter is embodied in a medicine management and identification method 2000, which depicts a medicine management and identification method implemented with the medicine management and identification system 10, as described in detail above. In the medicine management and identification method 2000, the first step includes receiving a medicine regimen from a medical practitioner of a specific patient, the medicine regimen including associated information 184 of a plurality of actual medicine products 180. A second step includes providing a periodic daily event color-code sheet 20 with instructions 26 for instructing the user, patient, family member, care giver, medical practitioner in the implementation of a medicine management and identification system 10. A third step includes providing one or more sheets of periodic daily event of the day labels 70, the one or more sheets of periodic daily event of the day labels 70, comprising, one or more preprinted periodic daily event labels, wherein each preprinted periodic daily event label 72 includes an adhesive back peel-off membrane 74, a first preprinted periodic daily event label 72¹ is completely shaded in a first color 24¹, yellow 24¹, and includes a viewable text¹ of a first periodic daily event of a day 22¹, Breakfast 22¹, preprinted thereon to form a Breakfast label 22¹; a second preprinted periodic daily event label 72² completely shaded in a second color 24², orange 24², and includes the viewable text² of a second periodic daily event of the day 22², Lunch 22², preprinted thereon to form a Lunch label 22²; a third preprinted periodic daily event label 72³ completely shaded in a third color 24 which is green 24³ and having the viewable text³ of a third periodic daily event of the day 22³, Dinner 22³, preprinted thereon to form a Dinner label 22³; a fourth preprinted periodic daily event label 72⁴ completely shaded in a fourth color 24⁴ which is blue 24⁴ and having a viewable text⁴ of the fourth periodic daily event of the day 22⁴, Bedtime 22⁴, preprinted thereon to form a Bedtime label 22⁴; and a fifth preprinted periodic daily event label 72⁵ completely shaded in a fifth color 24⁵ which is purple 24⁵ and having a viewable text⁵ of the fifth periodic daily event of the day 22⁵, As Needed 22⁵, preprinted thereon to form an As Needed label 22⁵.

A fourth step includes providing one or more sheets of Prescription/Supplement labels 800, the one or more sheets of Prescription/Supplements labels 800 each comprising, one or more preprinted Prescription/Supplements labels 802, wherein each preprinted Prescription/Supplements label 802 includes an adhesive back having a peel-off membrane 86, wherein each preprinted Prescription/Supplements label 802 whose associated information 184 is one or more indicators 801 preprinted thereon corresponding to a corresponding actual medicine product 180 identified by an exemplar 182 contained therewithin a medicine exemplar container 30 releasably attached to a Medicine/Supplement tile 126 of a medicine management chart 100, and corresponding to a second exemplar 182 of the corresponding actual medicine product 180 contained therewithin a corresponding remote medicine exemplar container 180' maintained within a medicine management cabinet 200, the one or more indicators 801 including a pharmaceutical name 804, or a trade name, a dosage 806, a time of administration 808, and adverse reactions 810 of the corresponding actual medicine product 180.

Step five includes providing one or more sheets of What's this for? labels 80, the one or more sheets of What's this for? labels 80 comprising, one or more preprinted What's this for? labels 82, wherein each preprinted What's this for? label 82 includes an adhesive back having a peel-off membrane 74, wherein each What's this for? label 82 bears one or more of known medical reasons 84 for administering the actual medicine product 180 preprinted thereon to the specific patient.

Step six includes providing the medicine management and identification system 10, the medicine management and identification system, comprising: a portable rigid magnetic board 40, a plurality of medicine exemplar containers 30, one or more medicine management charts 100, a medicine management cabinet 200, a mounting platform 50, an actual medicine product daily organizer 400, a mobile communications device 500, and a medicine management notebook 600, as discussed in detail above, and with reference to FIGS. 1-34 and thereby not repeated here for brevity sake.

Step seven includes storing the actual medicine products 180 into any one of the Breakfast drawer $260^1$, the Lunch drawer $260^2$, the Dinner drawer $260^3$, the Bedtime drawer $260^4$, the As Needed drawer $260^5$, as ascertained from a corresponding Prescription/Supplement label 802.

Step eight includes removably attaching the patient identification card $401^c$ of the specific patient to the $area^2$ of the patient identification tile 104 of the medicine management chart 100. Step nine includes removably attaching the medical practitioner identification card $401^c$ of a medical practitioner of the specific patient to the $area^1$ of the medical practitioner tile 102 of the medicine management chart 100.

Step ten includes preprinting a first Prescriptions/Supplements label 802 including identifiers for a first exemplar 182 and removably attaching the first Prescriptions/Supplements label 802 to a first Prescriptions/Supplements tile 128 of any one of the Breakfast matrix of tiles $106^1$, Lunch matrix of tiles $106^2$, Dinner matrix of tiles $106^3$, Bedtime matrix of tiles $106^4$, As Needed matrix of tiles $106^5$, as ascertained by the medicine regimen of the specific patient.

Step eleven includes preprinting a first What's this for? label 82 including identifiers 84 for the first exemplar 182 and removably attaching the first What's this for? label 82 to a first What's this for? tile 130 of any one of the Breakfast matrix of tiles $106^1$, the Lunch matrix of tiles $106^2$, the Dinner matrix of tiles $106^3$, the Bedtime matrix of tiles $106^4$, the As Needed matrix of tiles $106^5$, as ascertained by the medicine regimen of the specific patient.

Step twelve includes providing a first exemplar 182 corresponding to each of the actual medicine products 180. Step thirteen includes placing a first exemplar of the corresponding actual medicine product 180 into a first medicine exemplar container 30 of the plurality of medicine exemplar containers 30, and step fourteen including removably attaching the first medicine exemplar container 30 onto any one of a first Medicine/Supplement tile 126 of the Breakfast matrix of tiles $106^1$, the Lunch matrix of tiles $106^2$, the Dinner matrix of tiles $106^3$; the Bedtime matrix of tiles $106^4$, the As Needed matrix of tiles $106^5$, as ascertained from the corresponding first Prescriptions/Supplement label 802 on the medicine management chart 100.

Step fifteen includes placing a second exemplar 182 of the corresponding actual medicine product 180 into a second medicine exemplar 30 container of the plurality of exemplar containers forming a first remote medicine exemplar container 30'; removably attaching the first remote medicine exemplar container 30' onto any one of the raised front walls of the Breakfast drawer $160^1$, the Lunch drawer $160^2$, the Dinner drawer $160^3$, the Bedtime drawer $160^4$, the As Needed drawer $160^5$ as ascertained by the indicators 801 of the corresponding Prescriptions/Supplements label 802 on the medicine management chart 100.

Step sixteen identifying a first actual medicine product 180 by means of the first exemplar 30 contained therewithin the first medicine exemplar container 30, and the step seventeen identifying the first actual medicine product 180 a second time by means of the second exemplar 182 contained in the first remote medicine exemplar container 30'.

Step eighteen includes placing a dosage 806 of the first actual medicine product 180 into a first color shaded cubicle 406 of the actual medicine product daily organizer 400 in any one of a Breakfast row of yellow color shaded cubicles $414^1$, the Lunch row of orange color shaded cubicles $414^2$, the Dinner row of green color shaded cubicles $414^3$, the Bedtime row of blue color shaded cubicles $414^4$, the As Needed row of color shaded cubicles $414^4$ as ascertained by the indicators 801 of the corresponding Prescription/Supplements label 802 of the medicine management chart 100.

Step nineteen includes completing the medical management chart 100 as ascertained from the medical regimen of the specific patient, and the step twenty includes completing filling the dosages 806 into each of the color shaded cubicles 406 of the actual medicine product daily organizer 400 for each of the actual medicine products 180 as ascertained from the Prescription/Supplements labels 802 of the medicine management chart 100.

Step twenty-one includes completing the medical management chart 100 for the remainder of the actual medicine products 180 of the medical regimen for the specific patient, and step twenty-two includes completing filling the dosages 806 of the actual medicine products 180 into each of the color shaded cubicles 406 of each of the actual medicine products 180 as ascertained from the Prescription/Supplements labels 802 of the medicine management chart 100, and filling the one or more mateable mounting storage containers 248 with one or more auxiliary products 264.

Step twenty-three includes activating the mobile communications device 500, and the step twenty-four includes activating the preinstalled camera 502 for capturing a plurality of images 524, the images 524 including, images 524 at a time when the medicine management chart 100 is completed, images 524 at a time thereafter any changes made to the medicine management chart 100, images 524 of the caregiver, images of the specific patient throughout a term of the medicine regimen. Step twenty-five includes taking the images 524 by implementing the preinstalled camera 502, and step twenty-six storing the images 524 within one or more microprocessors of the mobile communications device 500, and step twenty-seven retrieving the images 524, and step twenty-eight using the images 524 to maneuver into a printer for printing a copy of the image 524 of the medicine management chart 100.

Step twenty-nine storing the images 524 within the medicine management notebook 600, and step thirty storing the images 524 within a memory of the mobile communication device 500; and step thirty-one storing the images 524 within a removable memory storage device 504.

I claim:
1. A medicine management and identification system, comprising:
   a portable rigid ferromagnetic substrate, a periodic daily event color-code sheet, a plurality of medicine exemplar containers, one or more malleable substrates, a medicine management cabinet, a mounting platform, an actual medicine product daily organizer, a mobile communications device, a medicine management notebook, wherein:
   the portable rigid ferromagnetic substrate adapted and operable to act as a portable rigid magnetic board so as to receive and removably retain a plurality of mateable mounting magnets, the portable rigid magnetic board including two layers, a first layer including a thin washable exterior surface supported by a second layer including a ferromagnetic substrate, the ferromagnetic substrate is magnetically attractable having a magnetic flux, wherein the magnetic flux is passable therethrough the thin washable exterior surface;
   the periodic daily event color-code sheet including one or more color-coded rows, wherein each color-coded row of the one or more color-coded rows is completely color shaded in a color preselected from a variety of different colors, wherein each color-coded row completely shaded in the color bears a viewing text corresponding to a periodic daily event of a day preselected from a number of different periodic daily events of the day preprinted thereon, for enabling for visually correlating the color with the periodic daily event of the day in a chronological arrangement at which time a specific patient is to be administered one or more of a plurality of actual medicine products of a medicine regimen prescribed for the specific patient by a medical practitioner;
   the plurality of medicine exemplar containers, wherein each of a medicine exemplar container of the plurality of medicine exemplar containers includes a transparent body defining an interior cavity and a transparent sealing cap adapted and operatively to be read therethrough, the transparent sealing cap adapted and operative for releasably attaching to the transparent body via a sealing means for enabling selectively receiving, containing and removing of an exemplar of a corresponding actual medicine product of the plurality of actual medicine products therewthin each of the medicine exemplar containers, wherein each of the transparent bodies of the plurality of medicine exemplar containers includes a mateable mounting magnet of the plurality of mateable mounting magnets permanently attached thereon adapted and operable for removably attaching each of the medicine exemplar containers thereon the portable rigid magnetic board and remotely thereon a drawer provided inside of a medicine management cabinet, the drawer including a ferromagnetic element;
   the one or more malleable substrates for use with the portable rigid magnetic board, each malleable substrate of the plurality of malleable substrates includes associated information corresponding to each of the exemplars of each of the corresponding actual medicine products contained therewithin, each of the malleable substrates, comprising:
   a front side and an underside;
      wherein the front side includes one or more identification tiles, one or more vertical columns and one or more horizontal rows intersecting to arrange one or more periodic daily event matrices of tiles preprinted thereon to form a medicine management chart;
      wherein the medicine management chart is removably attached to the portable rigid magnetic board by means of one or more medicine exemplar containers of the plurality of medicine exemplar containers including the mateable mounting magnet attached thereon so that the medicine management chart assembles visually and operatively against the portable rigid magnetic board;
      the underside is a blank sheet;
   a first identification tile of the one or more identification tiles includes a medical practitioner identification tile, wherein the medical practitioner identification tile includes an area for removably attaching a medical practitioner identification card, wherein the medical practitioner identification card includes a meateable mounting magnet of the plurality of mateable mounting magnets for removably attaching the medical practitioner identification card thereon the area of the medical practitioner identification tile;
   a second identification tile of the one or more identification tiles includes a patient identification tile for the specific patient, wherein the patient identification tile includes an area for removably attaching a patient identification card, wherein the patient identification card includes a mateable mounting magnet of the plurality of mateable mounting magnets for removably attaching the patient identification card thereon the area of the patient identification tile;
   wherein each of a periodic daily event matrix of tiles of the plurality of matrices of tiles is completely shaded in the color preselected from the variety of different colors including the viewing text corresponding to the periodic daily event of the day preprinted thereon as depicted on the periodic daily color-code sheet, wherein each of the periodic daily event matrix of tiles of the one or more periodic daily event matrices of tiles are arrayed in the chronological arrangement;
   a plurality of header tiles;
   a first header tile whose associated information is a first header preprinted text, Periodic Daily Event, heads a first row of each of the periodic daily event matrix of tiles of the plurality of periodic daily event matrices of tiles, wherein the first row includes an area bearing the viewing text of the periodic daily event preprinted thereon corresponding with the color of the periodic daily event matrix of tile;
   a second header tile whose associated information is a second header preprinted text, Medicine/Supplement Exemplar, heads each of a second row of the periodic daily event matrix of tiles of the one or more periodic daily event matrices of tiles, the second row including one or more of Medicine/Supplement exemplar tiles, wherein each of the Medicine/Supplement exemplar tiles includes an area for removably attaching a medicine exemplar container of the plurality of medicine exemplar containers, each medicine exemplar container containing the exemplar to the corresponding actual medicine product selected from the plurality of actual medicine products therewithin so as to visually correctly identify and correlate the actual medicine product to be administered to the specific patient at the periodic daily event of the day depicted by the viewing text of the periodic daily event preprinted in the area of the first row;

a third header tile whose associated information is a third header preprinted text, Prescription/Supplements, heads each of a third row of the periodic daily event matrix of tiles of the one or more periodic daily event matrices of tiles, the third row including one or more of Prescription/Supplements tiles, wherein each of the Prescription/Supplements tiles of the one or more of Prescription/Supplements tiles is vertically aligned to an adjacent Medicine/Supplement tile of the second row, wherein each of the Prescription/Supplements tiles includes an area adapted to receive a preprinted Prescription/Supplements label whose associated information is one or more indicators preprinted thereon corresponding to the corresponding actual medicine product identified by the exemplar contained therewithin the medicine exemplar container releasably attached to the adjacent Medicine/Supplement tile of the second row, and corresponding to a second exemplar of the corresponding actual medicine product contained therewithin a corresponding remote medicine exemplar container maintained within the medicine management cabinet, the one or more indicators including a pharmaceutical name, a trade name, a dosage, a method of administration, and adverse reactions of the corresponding actual medicine product;

a fourth header tile whose associated information is a fourth header preprinted text, What's this for?, heads each of a fourth row of the periodic daily event matrix of tiles of the one or more periodic daily event matrices of tiles, the fourth row including one or more of What's this for? tiles, each of the What's this for? tiles of the one or more What's this for? tiles is vertically aligned to each of the Medicine/Supplement tiles of the second row, wherein each of the What's this for? tiles includes an area adapted to receive a preprinted What's this for? label whose associated information is one or more of known medical reasons for administering the actual medicine product preprinted thereon corresponding to the corresponding actual medicine product identified by the exemplar contained therewithin the medicine exemplar container releasably attached to each of the vertically aligned Medicine/Supplement tile of the second row, and corresponding to a second exemplar of the corresponding actual medicine product contained therewithin a corresponding remote medicine exemplar container maintained within the medicine management cabinet;

the medicine management cabinet, comprising:

a housing body defining an open interior region, the housing body including an open front, a closed interior back wall, a closed exterior back wall, a top wall, a bottom floor plane, a right side wall, a left side wall, wherein the closed exterior back wall includes a permanently attached adjoining ferromagnetic wall adapted and operable to act as a permanent exterior magnetic board;

a divider wall removably inserted within the open interior region positioned vertically within the open interior region forming two vertical open interior portions, a first vertical open interior portion, and a second vertical open interior portion;

a door having a front planar surface and a rear planar surface, wherein the rear planar surface includes a ferromagnetic substrate therein adapted and operable for the rear planar surface to act as a magnetic inside door, the door extending from the bottom floor plane to the top wall and from the right side wall to the left side wall, the door being pivotally mounted to the housing and operable for selectively providing access to the open interior region thereof and covering the open front thereof;

a locking means adapted and operable for selectively opening and closing the door;

one or more mateable mounting storage containers wherein each of the one or more mateable mounting storage containers includes at least one of the mateable mounting magnets of the plurality of mateable mounting magnets adapted and operable for removably attaching and relocating one or more of the mateable mounting storage containers to the magnetic inside door, or to the exterior permanent magnetic board;

one or more mateable mounting hook devices adapted for enabling the display of a hanging medical apparatus, the one or more mateable mounting hook devices having at least one of the mateable mounting magnets of the plurality of mateable mounting magnets attached thereon adapted for removably attaching and relocating the one or more mateable mounting hook devices to the magnetic inside door or to the exterior permanent magnetic board;

one or more drawers, wherein each drawer of the one or more drawers is slidably engaged within the medicine management cabinet via a mounting means, wherein each drawer includes an upstanding right side wall, an upstanding left side wall, an upstanding rear wall, a base floor plane, and a raised front wall upstanding from a front surface of the base floor plane, wherein the raised front wall includes a ferromagnetic layer;

one or more of the medicine exemplar containers of the plurality of medicine exemplar containers is removably attached onto the raised front wall of each of the drawers of the one or more drawers forming one or more remote medicine exemplar containers to visually identify and correlate the second exemplar contained therewithin with the corresponding actual medicine product contained in a corresponding actual medicine product container stored therewithin the drawer immediately behind the one or more remote medicine exemplar containers;

a plurality of transferable malleable dividers, wherein one or more of a transferable malleable dividers of the plurality of transferable malleable dividers is configured to position within one or more drawers and operable for dividing the one or more drawers into two or more sections;

an open storage pocket formed by a rectangular panel having a recess in a front portion thereof being permanently attached to a rear exterior surface of the top wall of the medicine management cabinet and an exterior bottom floor plane of the bottom floor plane of the medicine management cabinet such that the open storage pocket behind the closed exterior back wall of the medicine management cabinet is formed, an open slot being provided between the top wall and the bottom floor plane for enabling access to the open storage pocket, wherein the open storage pocket is adapted and operable to slidably receive and store the portable rigid magnetic board when having the medicine management chart removably attached thereon;

a retractable handle integrally machined within the medicine management cabinet for enabling transport of the medicine management cabinet;

at least four swivel wheels attached to the bottom floor plane of the medicine management cabinet for enabling 360 degree swiveling movement of each of the wheels and operable to turn the medicine management cabinet in a 360 degrees clockwise direction or a 360 degrees counter-clockwise direction;

the mounting platform, comprising:
a support means for enabling the support of the portable rigid magnetic board having the medicine management chart removably attached thereon against sliding downwards due to gravitational force;

the actual medicine product daily organizer, comprising:
a generally flat housing including a uniform upwardly facing array of color shaded cubicles arranged in columns and rows;
wherein the rows of the color shaded cubicles sufficient in number for receiving doses of the actual medicine products at each of the periodic daily events of the day for each of seven days of a week, each of the seven days of the week arranged in columns over a preselected number of days;
wherein each of the color shaded cubicles includes an operable lid opening to a cavity, the operable lid adapted and operable for opening upwardly for receiving, containing, and removing of a dose of the actual medicine product as discerned from the Prescription/Supplement label corresponding to the corresponding actual medicine product identified by the exemplar contained therewithin the medicine exemplar container releasably attached to the adjacent Medicine/Supplement tile of the second row of the periodic daily event matrix of tiles;
wherein the operable lid is configured over the opening to the cavity and pivotally attached to an upper marginal edge of a rear side of each of the color shaded cubicles;
wherein each operable lid has an upwardly releasable locking means for selectively opening and closing the operable lid;
wherein each of the operable lids of the color shaded cubicles bearing the color of the periodic daily event of the day and each bearing the viewing text associated with the periodic daily event of the day as discerned from the periodic daily event color-code sheet are arrayed in the chronological arrangement depicted on the periodic daily event color-code sheet, and the arrangement of the periodic daily event matrices of tiles within the medicine management chart, and the chronological arrangement of the one or more drawers within the medicine management cabinet, advising of the proper sequence and timing of manually opening each of the operable lids of the color shaded cubicles to receive the dosage of the corresponding actual medicine product, contain the corresponding actual medicine products, and gain access to the dosage of the corresponding actual medicine product for administration to the specific patient;
a second viewing text includes each day of the days of a week preprinted thereon; and the mobile communications device, comprising:
one or more microprocessors configured to:
receive, identify, derive, store, retrieve, data input, input data via a user interface, the data input including identification of the specific patient, identification of the medical practitioner of the specific patient, caregiver of the specific patient, date, year, one or more medicine management charts, periodic daily event color-code sheet, one or more captured images of the medicine management chart identified by the date and the year;
a mobile cell phone having a preinstalled camera for capturing a plurality of images of the medicine management chart;

the medicine management notebook, comprising:
a storage device for receiving, storing, and retrieving a copy of the identified captured image of the medicine management chart.

2. The medicine management and identification system, according to claim 1, wherein the medicine management chart, further comprises:
a first periodic daily event matrix of tiles of the one or more periodic daily event matrices of tiles completely shaded in a first color preselected from the variety of different colors as depicted from the periodic daily event color-code sheet whose associated information is a viewing text bearing a first periodic daily event of the day preprinted thereon;
a second periodic daily event matrix of tiles of the one or more periodic daily event matrices of tiles completely shaded in a second color preselected from the variety of different colors as depicted on the periodic daily event color-code sheet whose associated information is a viewable text of a second periodic daily event of the day preprinted thereon;
a third periodic daily event matrix of tiles of the one or more of periodic daily event matrices of tiles completely shaded in a third color preselected from the variety of different colors as depicted on the periodic daily event color-code sheet whose associated information is a viewable text of a third periodic daily event of the day preprinted thereon;
a fourth periodic daily event matrix of tiles of the one or more of periodic daily event matrices of tiles completely shaded in a fourth color preselected from the variety of different colors as depicted on the periodic daily event color-code sheet whose associated information is a viewable text of a fourth periodic daily event of the day preprinted thereon; and
a fifth periodic daily event matrix of tiles of the one or more of periodic daily event matrices of tiles completely shaded in a fifth color preselected from the variety of different colors as depicted on the periodic daily event color-code sheet whose associated information is a viewable text of a fifth periodic daily event of the day preprinted thereon.

3. The medicine management and identification system, according to claim 2, wherein:
the first periodic daily event matrix of tiles is completely shaded with the first color which is yellow, and bearing the viewable text of the first periodic daily event of the day, which is Breakfast, preprinted thereon an area of the first row of the first periodic daily event matrix of tiles forming a Breakfast matrix of tiles;
the second periodic daily event matrix of tiles is completely shaded with the second color which is orange, and bearing the viewable text of the second periodic daily event of the day, which is Lunch, preprinted thereon the area of the first row of the second periodic daily event matrix of tiles forming a Lunch matrix of tiles;
the third periodic daily event matrix of tiles is completely shaded with the third color which is green, and bearing the viewable text of the third periodic daily event of the day which is Dinner, preprinted thereon the area of the first row of the third periodic daily event matrix of tiles forming a Dinner matrix of tiles;

the fourth periodic daily event matrix of tiles is completely shaded with the fourth color which is blue, and having the viewable text of the fourth periodic daily event of the day which is Bedtime, preprinted thereon the area of the first row of the fourth periodic daily event matrix of tiles forming a Bedtime matrix of tiles; and the fifth periodic daily event matrix of tiles is completely shaded with the fifth color, which is purple, and having the viewable text of the fifth periodic daily event of the day, which is As Needed, preprinted thereon the area of the first row of the fifth periodic daily event matrix of tiles forming an As Needed matrix of tiles.

4. The medicine management identification and management system, according to claim 3, further comprising one or more sheets of preprinted periodic daily event labels, the one or more sheets of preprinted periodic daily event labels comprising:

one or more preprinted periodic daily event labels, wherein each preprinted periodic daily event label includes an adhesive back having a peel-off membrane;

a first preprinted periodic daily event label completely shaded in the first color, yellow, and includes the viewable text bearing the first periodic daily event of the day, Breakfast, preprinted thereon to form a Breakfast label;

a second preprinted periodic daily event label completely shaded in the second color, orange, and includes the viewable text of the second periodic daily event of the day, Lunch, preprinted thereon to form a Lunch label;

a third preprinted periodic daily event label completely shaded in the third color which is green and having the viewable text of the third periodic daily event of the day, Dinner, preprinted thereon to form a Dinner label;

a fourth preprinted periodic daily event label completely shaded in the fourth color which is blue and having the viewable text of the fourth periodic daily event of the day, Bedtime, preprinted thereon to form a Bedtime label; and a fifth preprinted periodic daily event label completely shaded in a fifth color which is purple and having the viewable text of the fifth periodic daily event of the day, As Needed, preprinted thereon to form an As Needed label.

5. The medicine management identification and management system, according to claim 4, wherein the medicine management cabinet, further comprises:

a first drawer of the one or more drawers, wherein the first drawer includes the Breakfast label removably attached to the raised front wall of the first drawer via one of the mateable mounting magnets of the plurality of mateable mounting magnets to form a Breakfast drawer;

a second drawer of the one or more drawers, wherein the second drawer includes the Lunch label removably attached to the raised front wall of the second drawer via one of the mateable mounting magnets of the plurality of mateable mounting magnets to form a Lunch drawer;

a third drawer of the one or more drawers, wherein the third drawer includes the Dinner label removably attached to the raised front wall of the third drawer via one of the mateable mounting magnets of the plurality of mateable mounting magnets to form a Dinner drawer;

a fourth drawer of the one or more drawers, wherein the fourth drawer includes the Bedtime label removably attached to the raised front wall of the fourth drawer via one of the mateable mounting magnets of the plurality of mateable mounting magnets to form a Bedtime drawer; and a fifth drawer of the one or more drawers, wherein the fifth drawer includes the As Needed label removably attached to the raised front wall of the fifth drawer via one of the mateable mounting magnets of the plurality of mateable mounting magnets to form an As Needed drawer.

6. The medicine management identification and management system, according to claim 5, wherein:

the Breakfast drawer includes one or more remote medicine exemplar containers removably attached to the raised front wall of the Breakfast drawer forming a row of one or more Breakfast remote medicine exemplar containers, wherein each of a Breakfast remote medicine exemplar container of the one or more Breakfast remote medicine exemplar containers includes a second exemplar of the one or more actual medicine products stored within the Breakfast drawer so as to visually correlate each of the second exemplar contained therewithin each of the Breakfast remote medicine exemplar containers with a corresponding actual medicine product of the one or more actual medicine products stored within the Breakfast drawer of the medicine management cabinet, and with the exemplar contained therewithin a corresponding medicine exemplar container removably attached within each of the corresponding Medicine/Supplement exemplar tiles of the second row within the Breakfast matrix of tiles of the medicine management chart;

the Lunch drawer includes one or more remote medicine exemplar containers removably attached to the raised front wall of the Lunch drawer forming a row of one or more Lunch remote medicine exemplar containers, wherein each Lunch remote medicine exemplar container of the one or more Lunch remote medicine exemplar containers includes a second exemplar of the one or more of actual medicine products stored within the Lunch drawer so as to visually correlate each of the second exemplars$^L$ contained therewithin each of the one or more of the Lunch remote medicine exemplar containers with an actual medicine product of the one or more actual medicine product stored within the Lunch drawer of the medicine management cabinet and with the exemplar contained therewithin a corresponding medicine exemplar container removably attached within each of the corresponding Medicine/Supplement exemplar tiles of the second row of the Lunch matrix of tiles within the medicine management chart;

the Dinner drawer includes one or more remote exemplar containers removably attached to the raised front wall of the Dinner drawer forming a row of one or more Dinner remote medicine exemplar containers, wherein each Dinner remote medicine exemplar container of the one or more Dinner remote exemplar container includes a second exemplar of the one or more of actual medicine products stored within the Dinner drawer so as to visually correlate each of the second exemplars contained therewithin each of the one or more of the Dinner remote medicine exemplar containers with an actual medicine product of the one or more actual medicine products stored within the Dinner drawer of the medicine management cabinet and with the exemplar contained therewithin a corresponding medicine exemplar container removably attached within each of the corresponding Medicine/Supplement exemplar tiles of the second row of the Dinner matrix of tiles within the medicine management chart;

the Bedtime drawer includes one or more remote medicine exemplar containers removably attached to the raised front wall of the Bedtime drawer forming a row of one or more Bedtime remote medicine exemplar containers, wherein each Bedtime remote medicine exemplar containers of the one or more Bedtime remote exemplar medicine containers includes a second exemplar of the one or more of actual medicine products stored within the Bedtime drawer so as to visually correlate each of the second exemplars contained therewithin each of the one or more of Bedtime remote medicine exemplar containers with an actual medicine product of the one or more actual medicine products stored within the Bedtime drawer of the medicine management cabinet and with the exemplar contained therewithin a corresponding medicine exemplar container removably attached within the Bedtime matrix of tiles within each of the corresponding Medicine/Supplement exemplar tiles of the second row of the medicine management chart; and the As Needed drawer includes one or more remote medicine exemplar containers removably attached to the raised front wall of the As Needed drawer forming a row of one or more As Needed remote medicine exemplar containers, wherein each As Needed remote medicine exemplar container of the one or more As Needed remote medicine exemplar containers includes a second exemplar of the one or more of actual medicine products stored within the As Needed drawer so as to visually correlate each of the second exemplars contained therewithin each of the one or more of As Needed remote medicine exemplar containers with an actual medicine product of the one or more actual medicine products stored within the As Needed drawer of the medicine cabinet and with the exemplar contained therewithin a corresponding medicine exemplar container removably attached within the Lunch matrix of tiles within each of the corresponding Medicine/Supplement exemplar tiles of the second row of the medicine management chart.

7. The medicine management and identification system, according to claim 3, wherein the actual medicine product daily organizer, further comprises:

a first row of color shaded cubicles completely shaded in the first color, yellow, including the viewing text bearing the first periodic daily event of the day, Breakfast, preprinted thereon as depicted on the periodic daily event color-code per QS sheet to form a Breakfast row of yellow color shaded cubicles;

a second row of color shaded cubicles of the one or more rows of color shaded cubicles is completely shaded in the second color, orange, including the viewable text bearing the second periodic daily event of the day, Lunch, preprinted thereon as depicted on the periodic daily event color-code sheet to form a per QS Lunch row of orange color shaded cubicles;

a third row of color shaded cubicles of the one or more rows of color shaded cubicles is completely shaded in the third color, green, including the text bearing the third periodic daily event of the day, Dinner, preprinted thereon as depicted on the periodic daily event color-code sheet to form a Dinner row of green color shaded cubicles;

a fourth row of color shaded cubicles of the one or more rows of color shaded cubicles is completely shaded in the fourth color, blue, including the text bearing the fourth periodic daily event of the day, Bedtime, preprinted thereon as depicted on the periodic daily event color-code sheet to form a Bedtime row of blue color shaded cubicles; and a fifth row of color shaded cubicles of the one or more rows of color shaded cubicles is completely shaded in the fifth color, purple, including the text of the fifth periodic daily event of the day, As Needed, preprinted thereon as depicted on the periodic daily event color-code sheet to form an As Needed row of purple color shaded cubicles.

8. The medicine management and identification system, according to claim 1, wherein the variety of different colors can include any one of a color model of a variety of different colors preselected by a user.

9. The medicine management and identification system, according to claim 1, wherein the door of the medicine management cabinet is hingedly attached along a right marginal edge of the right side wall of the medicine management cabinet for enabling for selective opening and closing of the medicine management cabinet.

10. The medicine management and identification system, according to claim 1, wherein the front door of the medicine cabinet is hingedly attached along a left marginal edge of the left side wall of the medicine management cabinet for enabling for selective opening and closing of the medicine management cabinet.

11. The medicine management and identification system, according to claim 1, wherein the sealing means for releasably sealing the transparent sealing cap to the transparent body of the medicine exemplar container comprises one or more of the following: a threaded opening to mechanism, a snap fit mechanism, a ferromagnetic mechanism, a hinge mechanism.

12. The medicine management and identification system, according to claim 1, wherein one or more medicine exemplar containers of the plurality of medicine exemplar containers includes a perforated transparent sealing cap including perforations for enabling transmission of ambient air from an external environment into the interior cavity of the transparent body of the medicine exemplar container.

13. The medicine management and identification system, according to claim 1, wherein each of the transparent sealing caps of the plurality of medicine exemplar containers further includes a peripheral rim, wherein the peripheral rim is completely color shaded in a color of the variety of different colors including any one of the colors: yellow, orange, green, blue, and purple as depicted on the periodic daily event color code-sheet.

14. The medicine management and identification system, according to claim 1, wherein the specific patient is a pet animal.

15. The medicine management and identification system, according to claim 1, further comprising a portable miniature refrigeration unit removably maintained within the open interior region of the medicine management cabinet for enabling selectively cooling of the open interior region of the medicine management cabinet.

16. The medicine management and identification system, according to claim 1, wherein one or more of the one or more drawers further includes a docking station for enabling charging and recharging of the mobile communication device, and the cell phone.

17. The medicine management and identification system, according to claim 1, wherein the periodic daily events of the day of the specific patient can include a chronologic arrangement of the following: 7:00 A.M.-9:00 A.M., 11:00

A.M.-1:00 P.M., Noon, 3:00 P.M.-5:00 P.M., 7:00 P.M.-9:00 P.M., 11:00 P.M.-Midnight, Midnight-6:00 A.M.

18. The medicine management and identification system, according to claim 1, wherein the preprinted Prescription/Supplements label is provided by one or more sheets of preprinted Prescription/Supplements labels, the one or more sheets of preprinted Prescription/Supplements labels, comprising:
   one or more preprinted Prescription/Supplements labels, wherein each preprinted Prescription/Supplements label includes an adhesive back having a peel-off membrane;
   the one or more preprinted Prescription/Supplements labels each bearing the one or more indicators preprinted thereon;
   whereby a user peels off one of the preprinted Prescription/Supplements labels and adheres the Prescription/Supplements label to a mateable mounting magnet of the plurality of mateable mounting magnets for removably attaching the preprinted Prescription/Supplements label to the medicine management chart.

19. The medicine management and identification system, according to claim 1, wherein the preprinted What's this for? label is provided by one or more sheets of preprinted What's this for? labels, comprising:
   one or more preprinted What's this for? labels, wherein each preprinted What's this for? label includes an adhesive back having a peel-off membrane;
   the one or more preprinted What's this for? label each bearing the one or more of known medical reasons for administering the actual medicine product preprinted thereon;
   whereby a user peels off one of the preprinted What's this for? labels and adheres the preprinted What's this for? label to a mateable mounting magnet for removably attaching to the medicine management chart.

20. The medicine management and identification system, according to claim 1, wherein any one or more of known medical reasons for administering the actual medicine product for taking the medicine product includes any one of the following: Acid reflux, Allergies, Alzheimer, Arthritis, Asthma, Autism, Anti-Anxiety, Acne, Appetite, Anemia, Anti-oxidant, Bedsores, Bedwetting, Bipolar, Bladder overactive, Bronchitis, Bursitis, Blood Pressure, Boils, Cholesterol, Cancer, Crohn's disease, Canker sore, COPD, Cramps, Cyst, Dehydration, Depression, Diabetes, Diarrhea, Diverticulitis, Dermatitis, Dyslexia, Digestive Health, Digestive relief, Eczema, Epilepsy, Eyes, Ear, Endometriosis, Fainting, Fibromyalgia, Fungus, Gallbladder, Gallstones, Gout, Gerd, Gas relief, Heart, Heartburn, Hemmorrhoids, Hepatisits, Hives, High Potassium, Headache, Hernia, Hyperglcemia, Iron deficiency, Irritable Bowel, Itching, Influenza, Joints, Kidney, Leukemia, Lupus, Liver, Lung, Menopause, Migraine, Mood, Mononucleosis, Memory, Mesothelioma, Multiple Sclerosis (MS), Myelodysplastic Syndromes (MDS), Nails, Obesity, Osteoarthritis, Osteomyelitis, Osteoporosis, Obsessive Compulsive Disorder (OCD), Pain, Parkinson's, Pink Eye, Pneumonia, Post Nasal Drip, Post-Traumatic Stress Disorder, Premenstrual Syndrome, Psoriasis, Prostrate, Psychosis, Probiotic, Ringworm, Rosacea, . . . Rash, S. Scabies, . . . , Sciatica, Schizophrenia, Shingles, Sinus, Sleep disorder, Staph infection (MRSA), Strop throat (*Streptococcus* Group A), Stomach, Sun Burn, Supplement, Skin, Tuberculosis, Thyroid, Ulcers, Urinary Tract, Infection, Urinary tract supplement, Vertigo, Warts, Water Retention, Weight Management, Yeast Infection.

21. The medicine management and identification system, according to claim 1, wherein at least one of the one or more mateable mounting storage containers is an actual medicine product daily organizer storage container adapted to receive the actual medicine product daily organizer.

22. The medicine management and identification system, according to claim 1, wherein the top wall is pivotally attached to the dosed exterior back wall for selectively providing access to a top open region wherein a removable tray is maintained.

23. The medicine management and identification system, according to claim 1, wherein the top wall of the medicine management cabinet opens to a top open region having four perimeter walls, wherein at least one of the perimeter walls of the top open region includes a docking station adapted and operative to recharge the cell phone or a mobile communication device.

24. The medicine management and identification system, according to claim 1, wherein the permanent exterior magnetic board is a mirror.

25. The medicine management and identification system, according to claim 1, wherein the medicine cabinet is manufactured with a custom plastic thermoform with an anti-microbial property adapted and operable to resist the growth of bacteria, fungi, and viruses.

26. The medicine management and identification system, according to claim 1, wherein each of the one or more drawers of the medicine management cabinet further includes an exterior surface and an interior surface, wherein each of the exterior surface and the interior surface of each of the one or more drawers of is covered with an anti-microbial extrusion laminated reinforced film.

27. The medicine management and identification system, according to claim 1, wherein at least one of the one or more mateable mounting storage containers is a container manufactured with transparent acrylic adapted and operable to contain one or more 8 inches by 11 inches sized document(s).

28. The medicine management and identification appeaatu system, according to claim 1, wherein the mounting means includes:
   a first series of one or more pairs of corresponding channeled mounting tracks integrally machined within the upstanding right side wall of the medicine management cabinet and the first side of the divider wall, wherein each of the pairs of corresponding channeled mounting tracks is adapted and operable for receiving a right marginal edge and a left marginal edge of the base floor plane of the one or more drawers; and
   a second series of one or more pairs of channeled mounting tracks integrally machined within the left upstanding side wall of the medicine management cabinet and the second side of the divider wall, wherein each of the pairs of corresponding channeled mounting tracks is adapted and operable for receiving the right marginal edge and the left marginal edge of the base floor plane of the one or more drawers.

29. The medicine management and identification apparatu system, according to claim 1, wherein the mobile communications device, further comprising:
   a preinstalled application including one or more computing devices, each of the one or more computing devices having one or more processors configured to:
   receive data, the data including the identification of the specific patient, the identification of the medical practitioner, a diagnosis of the specific patient, a time, a date; the medical regimen for the specific patient, the pharmaceutical names of the plurality of actual medicine products, the image of the medicine management chart, the indicators corresponding to the actual medicine products, the associated information corresponding to the actual medicine products;

store the data within the computing device;

retrieve the data;

identify the data;

use an identified captured image of the medicine management chart to maneuver into a printer for printing a copy of the identified captured image of the medicine management chart;

use the identified captured image to store in a memory of the one or more processors; and use the identified captured image to maneuver into the medicine management notebook.

30. The medicine management and identification system, according to claim 1, wherein the medicine cabinet includes the generally trapezoidal shape, wherein the medicine cabinet further, comprises:

the door configured having a length of about 23.00 inches, a width of about 17.00 inches, and a thickness of about ½ inch;

the left side wall and the right side wall each configured with a bottom base$_1$ of about 14½ inches, a top base$_2$ of about 11.00 inches, and a height of about 23⅞ inches;

the closed exterior back wall configured with a length of about 23¾ inches, a width of about 18.00 inches, and the thickness of about ¾ inch;

the top wall configured with a length of about 19½ inches, a width of about 12.00 inches, and having the thickness of about ¾ inch; and the open storage pocket configured with the length of about 23.00 inches having a slot opening width of about 1½ inches.

31. The medicine management and identification system, according to claim 30, wherein the one or more drawers, further comprises:

one or more top drawers, including:

the upstanding right side wall and the upstanding left side wall each having a height of about 3⅝ inches;

the right side wall including a right top edge having a width of about 3⅞ inches, and a right bottom edge having a width of about 5⅝ inches;

the left side wall including a left top edge having the width of about 3⅞ inches, and a left bottom edge having the width of about 5⅝ inches;

the upstanding rear wall having the height of about 3⅝ inches, and a length of about 8⅛ inches;

the base floor plane having a length of about 8⅝ inches, and the width of about 5⅝ inches;

the raised front wall includes the length of about 8⅛ inches, and a height of about 1⅜ inches so that a right front edge of the upstanding right side wall and a left front edge of the upstanding left side wall are each configured having an identical slope $S^1$;

one or more middle drawers, including:

the upstanding right side wall and the upstanding left side wall each having the height of about 3⅝ inches;

the upstanding right side wall having the right top edge having a width of about 6.00 inches, and the right bottom edge having a width of about 7½ inches;

the upstanding left side wall having the left top edge having the width of about 6.00 inches, and the left bottom edge having the width of about 7½ inches;

the upstanding rear wall having the height of about 3⅝ inches, and the length of about 8⅛ inches;

the base floor plane having the length of about 8⅝ inches, and the width of about 7½ inches;

the raised front wall includes the length of about 8⅛ inches, and the height of about 1½ inches so that a right front edge of the upstanding right side wall and a left front edge of the upstanding left side wall are each configured having the identical slope S;

one or more bottom drawers, including:

the upstanding right side wall and the upstanding left side wall each having the height of about 3⅝ inches;

the upstanding right side wall having the right top edge having a width of about 7⅞ inches, and the right bottom edge having the width of about 9.00 inches;

the upstanding left side wall having the left top edge having the width of about 7⅞ inches, and the left bottom edge having the width of about 9.00 inches;

the upstanding rear wall having the height of about 3⅝ inches, and the length of about 8⅛ inches;

the base floor plane having the length of about 8⅝ inches, and the width of about 7½ inches;

the raised front wall includes the length of about 8⅛ inches, and the height of about 1½ inches so that a right front edge of the upstanding right side wall and a left front edge of the upstanding left side wall are each configured having the identical slope $S^1$.

32. The medicine management and identification system, according to claim 1, wherein the medicine cabinet includes a generally rectangular shape, wherein the medicine cabinet further, comprises:

the door configured with a length of about 23.00 inches, a width of about 17.00 inches, and a thickness of about ½ inch;

the top wall configured with a width of about 18.00 inches, a length of about 11¾ inches, and the thickness of about ¾ inch;

the left side wall and the right side wall each configured with the length of about 23.00 inches, a width of about 9½ inches, and the thickness of about ½ inch;

the closed exterior back wall configured with a length of about 23¾ inches, a width of about 17⅜ inches, and the thickness of about ½ inch;

the bottom floor plane configured with a width of about 17⅜ inches, a length of about 9 W inches, and the thickness of about ½ inch; and the open storage pocket configured with a length of about 22.00 inches, the width of about 17⅜ inches having a slot opening width of about 1½ inches.

33. The medicine management and identification system, according to claim 32, wherein the one or more drawers, further comprises:

the upstanding right side wall and the upstanding left side wall each having a height of about 3¾ inches;

the upstanding right side wall having a right top edge having a width of about 4¾ inches and a right bottom edge having a width of about 6½ inches;

the upstanding left side wall having a left top edge having the width of about 4¾ inches and a left bottom edge having the width of about 6½ inches;

the upstanding rear wall having the height of about 3¾ inches, and a length of about 7¾ inches;

the base floor plane having a length of about 8¼ inches, and the width of about 6½ inches; and the raised front wall includes the length of about 7¾ inches, and a height of about 1⅜ inches so that a right front edge of the upstanding right side wall and a left front edge of the upstanding left side wall are each configured having an identical slope S.

34. The medicine management and identification system, according to claim 1, wherein the medicine management cabinet includes non-rigid walls having a generally rectangular shape configured to form a mini-medicine management cabinet, the mini-medicine management cabinet, comprising:

the door configured with a length of about 12¼ inches, a width of about 14¼ inches, and a thickness of about ¼ inch;

the left side wall and the right side wall configured each with the length of about 12¼ inches, a width of about 4¼ inches, and a thickness of about ¼ inch;

the closed exterior back wall configured with the length of about 12¼ inches, the width ($W^{301}$) of about 14¼ inches, and the thickness of about ¼ inch;

the top wall configured with the width of about 14¼ inches, a length of about 4¼ inches, the thickness of about ¼ inch;

the open storage pocket configured with a length of about 12.00 inches, a width of about 14.00 inches and having a slot opening width of about 1½ inches;

the one or more mateable mounting storage containers, wherein each of the mateable mounting storage containers is configured with a height of about 5½ inches, a width of about 6¼ inches, and an opening having a depth of about 1½ inches;

the one or more drawers, wherein each of the drawers including the upstanding rear wall with a height of about 3¾ inches, having a width of about 6.00 inches, a raised front wall having the height of about 3¾ inches, and the upstanding right side wall with the height of about 3¾ inches and a width of about 2.00 inches, and the upstanding left side wall with the height of about 3¾ inches and the width of about 2.00 inches, and a top wall plane and the base floor plane of the drawer configured with the width of about 6.00 inches and having a length of about 2.00 inches;

a locking means adapted and operable for selectively opening and closing the door, wherein, the locking means is a zipper.

35. The medicine management and identification system, according to claim 34 wherein the drawers are removably attached to an interior closed back wall by means of any one of the following: mateable mounting magnets, hook and loop.

36. A medicine management and identification kit, the medicine management and identification kit, comprising:

a medicine management and identification system, the medicine management and identification system comprising:

a portable rigid magnetic board, a periodic daily event color-code sheet, a plurality of medicine exemplar containers, one or more medicine management charts, a medicine management cabinet, a mounting platform, an actual medicine product daily organizer, a mobile communications device, a medicine management notebook, wherein:

the portable rigid magnetic board adapted and operable to act as a portable rigid magnetic board so as to receive and removably retain a plurality of mateable mounting magnets, the portable rigid magnetic board including two layers, a first layer including a thin washable exterior surface supported by a second layer including a ferromagnetic substrate, the ferromagnetic substrate is magnetically attractable having a magnetic flux, wherein the magnetic flux is passable therethrough the thin washable exterior surface;

the periodic daily event color-code sheet including one or more color-coded rows, wherein each color-coded row of the one or more color-coded rows is completely color shaded in a color preselected from a variety of different colors, wherein each color-coded row completely shaded in the color bears a viewing text corresponding to a periodic daily event of a day preselected from a number of different periodic daily events of the day preprinted thereon, for enabling for visually correlating the color with the periodic daily event of the day in a chronological arrangement at which time a specific patient is to be administered one or more of a plurality of actual medicine products of a medicine regimen prescribed for the specific patient by a medical practitioner;

the plurality of medicine exemplar containers, wherein each of a medicine exemplar container of the plurality of medicine exemplar containers includes a transparent body defining an interior cavity and a transparent sealing cap adapted and operatively to be read therethrough, the transparent sealing cap adapted and operative for releasably attaching to the transparent body via a sealing means for enabling selectively receiving, containing and removing of an exemplar of a corresponding actual medicine product of the plurality of actual medicine products therewthin each of the medicine exemplar containers, wherein each of the transparent bodies of the plurality of medicine exemplar containers includes a mateable mounting magnet of the plurality of mateable mounting magnets permanently attached thereon adapted and operable for removably attaching each of the medicine exemplar containers thereon the portable rigid magnetic board and remotely thereon a drawer provided inside of a medicine management cabinet, the drawer including a ferromagnetic element;

the one or more medicine management charts for use with the portable rigid magnetic board, each of the medicine management charts of the one or more medicine management charts includes associated information corresponding to each of the exemplars of each of the corresponding actual medicine products contained therewithin, each of the medicine management charts, comprising:

a front side and an underside;

wherein the front side includes one or more identification tiles, one or more vertical columns and one or more horizontal rows intersecting to arrange one or more periodic daily event matrices of tiles preprinted thereon the medicine management chart;

wherein the medicine management chart is removably attached to the portable rigid magnetic board by means of one or more medicine exemplar containers of the plurality of medicine exemplar containers including the mateable mounting magnet attached thereon so that the medicine management chart assembles visually and operatively against the portable rigid magnetic board; the underside is a blank sheet;

a first identification tile of the one or more identification tiles includes a medical practitioner identification tile, wherein the medical practitioner identification tile includes an area for removably attaching a medical practitioner identification card, wherein the medical practitioner identification card includes a meateable mounting magnet of the plurality of mateable mounting magnets for removably attaching the medical practitioner identification card thereon the area of the medical practitioner identification tile;

a second identification tile of the one or more identification tiles includes a patient identification tile for the specific patient, wherein the patient identification tile includes an area for removably attaching a patient identification card, wherein the patient identification card includes a mateable mounting magnet of the plurality of mateable mounting magnets for removably attaching the patient identification card thereon the area of the patient identification tile;

wherein each of a periodic daily event matrix of tiles of the plurality of matrices of tiles is completely shaded in the color preselected from the variety of different colors including the viewing text corresponding to the periodic daily event of the day preprinted thereon as depicted on the periodic daily event color-code sheet, wherein each of the periodic daily event matrix of tiles of the one or more periodic daily event matrices of tiles are arrayed in the chronological arrangement;

a plurality of header tiles;

a first header tile whose associated information is a first header preprinted text, Periodic Daily Event, heads a first row of each of the periodic daily event matrix of tiles of the plurality of periodic daily event matrices of tiles, wherein the first row includes an area bearing the viewing text of the periodic daily event preprinted thereon corresponding with the color of the periodic daily event matrix of tile;

wherein the first periodic daily event matrix of tiles is completely shaded with the first color which is yellow, and bearing the viewable text of the first periodic daily event of the day, which is Breakfast, preprinted thereon an area of the first row of the first periodic daily event matrix of tiles forming a Breakfast matrix of tiles;

the second periodic daily event matrix of tiles is completely shaded with the second color which is orange, and bearing the viewable text of the second periodic daily event of the day, which is Lunch, preprinted thereon the area of the first row of the second periodic daily event matrix of tiles forming a Lunch matrix of tiles;

the third periodic daily event matrix of tiles is completely shaded with the third color which is green, and bearing the viewable text of the third periodic daily event of the day which is Dinner, preprinted thereon the area of the first row of the third periodic daily event matrix of tiles forming a Dinner matrix of tiles;

the fourth periodic daily event matrix of tiles is completely shaded with the fourth color which is blue, and having the viewable text of the fourth periodic daily event of the day which is Bedtime, preprinted thereon the area of the first row of the fourth periodic daily event matrix of tiles forming a Bedtime matrix of tiles;

the fifth periodic daily event matrix of tiles is completely shaded with the fifth color, which is purple, and having the viewable text of the fifth periodic daily event of the day, which is As Needed, preprinted thereon the area of the first row of the fifth periodic daily event matrix of tiles forming an As Needed matrix of tiles;

a second header tile whose associated information is a second header preprinted text, Medicine/Supplement Exemplar, heads each of a second row of the periodic daily event matrix of tiles of the one or more periodic daily event matrices of tiles, the second row including one or more of Medicine/Supplement exemplar tiles, wherein each of the Medicine/Supplement exemplar tiles includes an area for removably attaching a medicine exemplar container of the plurality of medicine exemplar containers, each medicine exemplar container containing the exemplar to the corresponding actual medicine product selected from the plurality of actual medicine products therewithin so as to visually correctly identify and correlate the actual medicine product to be administered to the specific patient at the periodic daily event of the day depicted by the viewing text of the periodic daily event preprinted in the area of the first row;

a third header tile whose associated information is a third header preprinted text, Prescription/Supplements, heads each of a third row of the periodic daily event matrix of tiles of the one or more periodic daily event matrices of tiles, the third row including one or more of Prescription/Supplements tiles, wherein each of the Prescription/Supplements tiles of the one or more of Prescription/Supplements tiles is vertically aligned to an adjacent Medicine/Supplement tile of the second row, wherein each of the Prescription/Supplements tiles includes an area adapted to receive a preprinted Prescription/Supplements label whose associated information is one or more indicators preprinted thereon corresponding to the corresponding actual medicine product identified by the exemplar contained therewithin the medicine exemplar container releasably attached to the adjacent Medicine/Supplement tile of the second row, and corresponding to a second exemplar of the corresponding actual medicine product contained therewithin a corresponding remote medicine exemplar container maintained within the medicine management cabinet, the one or more indicators including a pharmaceutical name, a trade name, a dosage, a method of administration, and adverse reactions of the corresponding actual medicine product;

a fourth header tile whose associated information is a fourth header preprinted text, What's this for?, heads each of a fourth row of the periodic daily event matrix of tiles of the one or more periodic daily event matrices of tiles, the fourth row including one or more of What's this for? tiles, each of the What's this for? tiles of the one or more What's this for? tiles is vertically aligned to each of the Medicine/Supplement tiles of the second row, wherein each of the What's this for? tiles includes an area adapted to receive a preprinted What's this for? label whose associated information is one or more of known medical reasons for administering the actual medicine product preprinted thereon corresponding to the corresponding actual medicine product identified by the exemplar contained therewithin the medicine exemplar container releasably attached to each of the vertically aligned Medicine/Supplement tile of the second row, and corresponding to a second exemplar of the corresponding actual medicine product contained therewithin a corresponding remote medicine exemplar container maintained within the medicine management cabinet;

the medicine management cabinet, comprising:
- a housing defining an open interior region, the housing including an open front, a closed interior back wall, a closed exterior back wall, a top wall, a bottom floor plane, a right side wall, a left side wall, wherein the closed exterior back wall includes a permanently attached adjoining ferromagnetic wall adapted and operable to act as a permanent exterior magnetic board;
- a divider wall removably inserted within the open interior region positioned vertically within the open interior region forming two vertical open interior portions, a first vertical open interior portion, and a second vertical open interior portion;
- a door having a front planar surface and a rear planar surface, wherein the rear planar surface includes a ferromagnetic substrate therein adapted and operable for the rear planar surface to act as a magnetic inside door, the door extending from the bottom floor plane to the top wall and from the right side wall to the left side wall, the door being pivotally mounted to the housing and operable for selectively providing access to the open interior region thereof and covering the open front thereof;
- a locking means adapted and operable for selectively opening and closing the door;
- one or more mateable mounting storage containers wherein each of the one or more mateable mounting storage containers includes at least one of the mateable mounting magnets of the plurality of mateable mounting magnets adapted and operable for removably attaching and relocating one or more of the of mateable mounting storage containers to the magnetic inside door, or to the exterior permanent magnetic board;
- one or more mateable mounting hook devices adapted for enabling the display of a hanging medical apparatus, the one or more mateable mounting hook devices having at least one of the mateable mounting magnets of the plurality of mateable mounting magnets attached thereon adapted for removably attaching and relocating the one or more mateable mounting hook devices to the magnetic inside door or to the exterior permanent magnetic board;
- one or more drawers, wherein each drawer of the one or more drawers is slidably engaged within the medicine management cabinet via a mounting means, wherein each drawer includes an upstanding right side wall, an upstanding left side wall, an upstanding rear wall, a base floor plane, and a raised front wall upstanding from a front surface of the base floor plane, wherein the raised front wall includes a ferromagnetic layer;
- wherein a first drawer of the one or more drawers, wherein the first drawer includes the Breakfast label removably attached to the raised front wall of the first drawer via one of the mateable mounting magnets of the plurality of mateable mounting magnets to form a Breakfast drawer;
- a second drawer of the one or more drawers, wherein the second drawer includes the Lunch label removably attached to the raised front wall of the second drawer via one of the mateable mounting magnets of the plurality of mateable mounting magnets to form a Lunch drawer;
- a third drawer of the one or more drawers, wherein the third drawer includes the Dinner label removably attached to the raised front wall of the third drawer via one of the mateable mounting magnets of the plurality of mateable mounting magnets to form a Dinner drawer;
- a fourth drawer of the one or more drawers, wherein the fourth drawer includes the Bedtime label removably attached to the raised front wall of the fourth drawer via one of the mateable mounting magnets of the plurality of mateable mounting magnets to form a Bedtime drawer;
- a fifth drawer of the one or more drawers, wherein the fifth drawer includes the As Needed label removably attached to the raised front wall of the fifth drawer via one of the mateable mounting magnets of the plurality of mateable mounting magnets to form an As Needed drawer;
- one or more of the medicine exemplar containers of the plurality of medicine exemplar containers is removably attached onto the raised front wall of each of the drawers of the one or more drawers forming one or more remote medicine exemplar containers to visually identify and correlate the second exemplar contained therewithin with the corresponding actual medicine product contained in a corresponding actual medicine product container stored therewithin the drawer immediately behind the one or more remote medicine exemplar containers;
- a plurality of transferable malleable dividers, wherein one or more of a transferable malleable dividers of the plurality of transferable malleable dividers is configured to position within one or more drawers and operable for dividing the one or more drawers into two or more sections;
- an open storage pocket formed by a rectangular panel having a recess in a front portion thereof being permanently attached to a rear exterior surface of the top wall of the medicine management cabinet and an exterior bottom floor plane of the bottom floor plane of the medicine management cabinet such that the open storage pocket behind the closed exterior back wall of the medicine management cabinet is formed, an open slot being provided between the top wall and the bottom floor plane for enabling access to the open storage pocket, wherein the open storage pocket is adapted and operable to slidably receive and store the portable rigid magnetic board when having the medicine management chart removably attached thereon;
- a retractable handle integrally machined within the medicine management cabinet for enabling transport of the medicine management cabinet;
- at least four swivel wheels attached to the bottom floor plane of the medicine management cabinet for enabling 360 degree swiveling movement of each of the wheels and operable to turn the medicine management cabinet in a 360 degrees clockwise direction or a 360 degrees counter-clockwise direction;

the mounting platform, comprising:
- a support means for enabling the support of the portable rigid magnetic board having the medicine management chart removably attached thereon against sliding downwards due to gravitational force;

the actual medicine product daily organizer, comprising:
a generally flat housing including a uniform upwardly facing array of color shaded cubicles arranged in columns and rows;
wherein the rows of the color shaded cubicles sufficient in number for receiving doses of the actual medicine products at each of the periodic daily events of the day for each of seven days of a week, each of the seven days of the week arranged in columns over a preselected number of days;
wherein each of the color shaded cubicles includes an operable lid opening to a cavity, the operable lid adapted and operable for opening upwardly for receiving, containing, and removing of a dose of the actual medicine product as discerned from the Prescription/Supplement label corresponding to the corresponding actual medicine product identified by the exemplar contained therewithin the medicine exemplar container releasably attached to the adjacent Medicine/Supplement tile of the second row of the periodic daily event matrix of tiles;
wherein the operable lid is configured over the opening to the cavity and pivotally attached to an upper marginal edge of a rear side of each of the color shaded cubicles;
wherein each operable lid has an upwardly releasable locking means for selectively opening and closing the operable lid;
wherein each of the operable lids of the color shaded cubicles bearing the color of the periodic daily event of the day and each bearing the viewing text associated with the periodic daily event of the day as discerned from the periodic daily event code-sheet are arrayed in the chronological arrangement depicted on the periodic daily event color-code sheet, and the arrangement of the periodic daily event matrices of tiles within the medicine management chart, and the chronological arrangement of the one or more drawers within the medicine management cabinet, advising of the proper sequence and timing of manually opening each of the operable lids of the color shaded cubicles to receive the dosage of the corresponding actual medicine product, contain the corresponding actual medicine products, and gain access to the dosage of the corresponding actual medicine product for administration to the specific patient,
a second viewing text includes each day of the days of a week preprinted thereon;
wherein a first row of color shaded cubicles completely shaded in the first color, yellow, including the viewing text bearing the first periodic daily event of the day, Breakfast, preprinted thereon as depicted on the periodic daily event color-code sheet to form a Breakfast row including yellow color shaded cubicles;
a second row of color shaded cubicles of the one or more rows of color shaded cubicles is completely shaded in the second color, orange, including the viewable text bearing the second periodic daily event of the day, Lunch, preprinted thereon as depicted on the periodic daily event color-code sheet to form a per QS Lunch row of orange color shaded cubicles;
a third row of color shaded cubicles of the one or more rows of color shaded cubicles is completely shaded in the third color, green, including the text bearing the third periodic daily event of the day, Dinner, preprinted thereon as depicted on the periodic daily event color-code sheet to form a Dinner row of green color shaded cubicles;
a fourth row of color shaded cubicles of the one or more rows of color shaded cubicles is completely shaded in the fourth color, blue, including the text bearing the fourth periodic daily event of the day, Bedtime, preprinted thereon as depicted on the periodic daily event color-code sheet to form a Bedtime row of blue color shaded cubicles; and
a fifth row of color shaded cubicles of the one or more rows of color shaded cubicles is completely shaded in the fifth color, purple, including the text of the fifth periodic daily event of the day, As Needed, preprinted thereon as depicted on the periodic daily event color-code sheet to form an As Needed row of purple color shaded cubicles; and the mobile communications device, comprising:
one or more microprocessors configured to:
receive, identify, derive, store, retrieve, data input, input data via a user interface the data input including identification of the specific patient, identification of the medical practitioner of the specific patient, caregiver of the specific patient, date, year, one or more medicine management charts, periodic daily event color-code sheet, one or more captured images of the medicine management chart;
a mobile cell phone having a preinstalled camera for capturing a plurality of images of the medicine management chart;
the medicine management notebook, comprising:
a storage device for receiving, storing, and retrieving a copy of the identified image of the medicine management chart;
an instruction sheet for instructing the user, patient, family member, care giver, medical practitioner in the implementation of the medicine management and identification system;
one or more sheets of periodic daily event of the day labels, the one or more sheets of preprinted periodic daily event labels comprising:
one or more preprinted periodic daily event labels, wherein each preprinted periodic daily event label includes an adhesive back having a peel-off membrane;
a first preprinted periodic daily event label completely shaded in the first color, yellow, and includes the viewable text bearing the first periodic daily event of the day, Breakfast, preprinted thereon to form a Breakfast label;
a second preprinted periodic daily event label completely shaded in the second color, orange, and includes the viewable text of the second periodic daily event of the day, Lunch, preprinted thereon to form a Lunch label;
a third preprinted periodic daily event label completely shaded in the third color which is green and having the viewable text of the third periodic daily event of the day, Dinner, preprinted thereon to form a Dinner label;
a fourth preprinted periodic daily event label completely shaded in the fourth color which is blue and having the viewable text of the fourth periodic daily event of the day, Bedtime, preprinted thereon to form a Bedtime label; and a fifth preprinted periodic daily event label completely shaded in a fifth color which is to purple and having the viewable text of the fifth periodic daily event of the day,
    As Needed, preprinted thereon to form an As Needed label;
one or more sheets of Prescription/Supplement labels, the one or more sheets of Prescription/Supplements labels, comprising:
    one or more preprinted Prescription/Supplements labels, wherein each preprinted Prescription/Supplements label includes an adhesive back having a peel-off membrane, the preprinted Prescription/Supplements label whose associated information is one or more indicators preprinted thereon corresponding to a corresponding actual medicine product identified by the exemplar contained therewithin the medicine exemplar container releasably attached to the adjacent Medicine/Supplement tile of the second row, and corresponding to a second exemplar of the corresponding actual medicine product contained therewithin a corresponding remote medicine exemplar container maintained within the medicine management cabinet, the one or more indicators including a pharmaceutical name, a trade name, a dosage, a method of administration, and adverse reactions of the corresponding actual medicine product; and
one or more sheets of What's this for? labels, the one or more sheets of What's this for? labels comprising:
    one or more preprinted What's this for? labels, wherein each preprinted What's this for? label includes an adhesive back having a peel-off membrane;
    wherein each What's this for? label bears one or more of known medical reasons for administering the actual medicine product preprinted thereon to the specific patient.

37. The medicine management and identification kit, according to claim 36, further comprising:
    a mini-medicine management cabinet;
    a portable refrigeration unit;
    a plurality of band aides;
    an antiseptic tincture;
    an eye dropper;
    a syringe;
    a pill cutter;
    a measuring spoon;
    an ampule cutter;
    a pair of magnifying glasses;
    a bottle of aspirin;
    an epi-pen;
    a comb;
    antiseptic-wipes;
    disposable wipes;
    digital thermometer; and
    scissors.

38. A medicine management and identification method, the medicine management and identification method, comprising:
    receiving a medicine regimen from a medical practitioner of a specific patient, the medicine regimen including associated information of a plurality of actual medicine products;
    providing an instruction sheet for instructing the user, patient, family member, care giver, medical practitioner in the implementation of a medicine management and identification system;
    providing one or more sheets of periodic daily event of the day labels, the one or more sheets of periodic daily event of the day labels, comprising, one or more preprinted periodic daily event labels, wherein each preprinted periodic daily event label includes an adhesive back having a peel-off membrane, a first preprinted periodic daily event label is completely shaded in a first color, yellow, and includes a viewable text of a first periodic daily event of a day, Breakfast, preprinted thereon to form a Breakfast label; a second preprinted periodic daily event label completely shaded in a second color, orange, and includes the viewable text of a second periodic daily event of the day, Lunch, preprinted thereon to form a Lunch label; a third preprinted periodic daily event label completely shaded in a third color which is green and having the viewable text of a third periodic daily event of the day, Dinner, preprinted thereon to form a Dinner label; a fourth preprinted periodic daily event label completely shaded in a fourth color which is blue and having a viewable text of the fourth periodic daily event of the day, Bedtime, preprinted thereon to form a Bedtime label; and a fifth preprinted periodic daily event label completely shaded in a fifth color which is purple and having a viewable text of the a periodic daily event of the day, As Needed, preprinted thereon to form an As Needed label;
    providing one or more sheets of Prescription/Supplement labels, the one or more sheets of Prescription/Supplements labels each comprising, one or more preprinted Prescription/Supplements labels, wherein each preprinted Prescription/Supplements label includes an adhesive back having a peel-off membrane, wherein each preprinted Prescription/Supplements label whose associated information is one or more indicators preprinted thereon corresponding to a corresponding actual medicine product identified by an exemplar contained therewithin a medicine exemplar container releasably attached to a Medicine/Supplement tile of a medicine management chart, and corresponding to a second exemplar of the corresponding actual medicine product contained therewithin a corresponding remote medicine exemplar container maintained within a medicine management cabinet, the one or more indicators including a pharmaceutical name, a trade name, a dosage, a method of administration, and adverse reactions of the corresponding actual medicine product; and
    providing one or more sheets of Whats this for? labels, the one or more sheets of What's this for? labels comprising, one or more preprinted What's this for? labels, wherein each preprinted What's this for? label includes an adhesive back having a peel-off membrane, wherein each What's this for? label bears one or more of known medical reasons for administering the actual medicine product preprinted thereon to the specific patient;
    providing the medicine management and identification system, the medicine management and identification system, comprising:
        a portable rigid magnetic board, a periodic daily event color-code sheet, a plurality of medicine exemplar containers, one or more medicine management charts, a medicine management cabinet, a mounting platform, an actual medicine product daily organizer, a mobile communications device, a medicine management notebook, wherein: the portable rigid magnetic board adapted and operable to act as a portable rigid magnetic board so as to receive and removably retain a plurality of mateable mounting magnets, the portable rigid magnetic board including two layers, a first layer including a thin washable exterior surface supported by a second layer including a ferromagnetic substrate, the ferromagnetic substrate is magnetically attractable having a magnetic flux, wherein the magnetic flux is passable therethrough the thin washable exterior surface; the periodic daily event color-code sheet including one or more color-coded rows, wherein each color-coded row of the one or more color-coded rows is completely color shaded in a color preselected from a variety of different colors, wherein each color-coded row completely shaded in the color bears a viewing text corresponding to a periodic daily event of a day preselected from a number of different periodic daily events of the day preprinted thereon, for enabling for visually correlating the color with the periodic daily event of the day in a chronological arrangement at which time a specific patient is to be administered one or more of a plurality of actual medicine products of a medicine regimen prescribed for the specific patient by a medical practitioner; wherein a first color is yellow and a first periodic daily event of the day is Breakfast; a second color is orange and a second periodic daily event of the day is Lunch; a third color is green and the third periodic daily event of the day is Dinner; a fourth color is blue and a fourth periodic daily event of the day is Bedtime; a fifth color is purple and a fifth periodic daily event of the day is As Needed; the plurality of medicine exemplar containers, wherein each of a medicine exemplar container of the plurality of medicine exemplar containers includes a transparent body defining an interior cavity and a transparent sealing cap adapted and operatively to be read therethrough, the transparent sealing cap adapted and operative for releasably attaching to the transparent body via a sealing means for enabling selectively receiving, containing and removing of an exemplar of a corresponding actual medicine product of the plurality of actual medicine products therewthin each of the medicine exemplar containers, wherein each of the transparent bodies of the plurality of medicine exemplar containers includes a mateable mounting magnet of the plurality of mateable mounting magnets permanently attached thereon adapted and operable for removably attaching each of the medicine exemplar containers thereon the portable rigid magnetic board and remotely thereon a drawer provided inside of a medicine management cabinet, the drawer including a ferromagnetic element; the one or more medicine management charts for use with the portable rigid magnetic board, each of the medicine management chart of the one or more medicine management charts includes associated information corresponding to each of the exemplars of each of the corresponding actual medicine products contained therewithin, each of the malleable substrates, comprising: a front side and an underside; wherein the front side includes one or more identification tiles, one or more vertical columns and one or more horizontal rows intersecting to arrange one or more periodic daily event matrices of tiles preprinted thereon to form a medicine management chart; wherein the medicine management chart is removably attached to the portable rigid magnetic board by means of one or more medicine exemplar containers of the plurality of medicine exemplar containers including the mateable mounting magnet attached thereon so that the medicine management chart assembles visually and operatively against the portable rigid magnetic board; the underside is a blank sheet; a first identification tile of the one or more identification tiles includes a medical practitioner identification tile, wherein the medical practitioner identification tile includes an area for removably attaching a medical practitioner identification card, wherein the medical practitioner identification card includes a meateable mounting magnet of the plurality of mateable mounting magnets for removably attaching the medical practitioner identification card thereon the area of the medical practitioner identification tile; a second identification tile of the one or more identification tiles includes a patient identification tile for the specific patient, wherein the patient identification tile includes an area for removably attaching a patient identification card, wherein the patient identification card includes a mateable mounting magnet of the plurality of mateable mounting magnets for removably attaching the patient identification card thereon the area of the patient identification tile; wherein each of a periodic daily event matrix of tiles of the plurality of matrices of tiles is completely shaded in the color preselected from the variety of different colors including the viewing text corresponding to the periodic daily event of the day preprinted thereon as depicted on the periodic daily color-code sheet, wherein each of the periodic daily event matrix of tiles of the one or more periodic daily event matrices of tiles are arrayed in the chronological arrangement; a plurality of header tiles; a first header tile whose associated information is a first header preprinted text, Periodic Daily Event, heads a first row of each of the periodic daily event matrix of tiles of the plurality of periodic daily event matrices of tiles, wherein the first row includes an area bearing the viewing text of the periodic daily event preprinted thereon corresponding with the color of the periodic daily event matrix of tiles; a second header tile whose associated information is a second header preprinted text, Medicine/Supplement Exemplar, heads each of a second row of the periodic daily event matrix of tiles of the one or more periodic daily event matrices of tiles, the second row including one or more of Medicine/Supplement exemplar tiles, wherein each of the Medicine/Supplement exemplar tiles includes an area for removably attaching a medicine exemplar container of the plurality of medicine exemplar containers, each medicine exemplar container containing the exemplar to the corresponding actual medicine product selected from the plurality of actual medicine products therewithin so as to visually correctly identify and correlate the actual medicine product to be administered to the specific patient at the periodic daily event of the day depicted by the viewing text of the periodic daily event preprinted in the area of the first row; a third header tile whose associated information is a third header preprinted text, Prescription/Supplements, heads each of a third row of the periodic daily event matrix of tiles of the one or more periodic daily event matrices of tiles, the third row including one or more of Prescription/Supplements tiles, wherein each of the Prescription/Supplements tiles of the one or more of Prescription/Supplements tiles is vertically aligned to an adjacent Medicine/Supplement tile of the second row, wherein each of the Prescription/Supplements tiles includes an area adapted to receive a preprinted Prescription/Supplements label whose associated information is one or more indicators preprinted thereon corresponding to the corresponding actual medicine product identified by the exemplar contained therewithin the medicine exemplar container releasably attached to the adjacent Medicine/Supplement tile of the second row, and corresponding to a second exemplar of the corresponding actual medicine product contained therewithin a corresponding remote medicine exemplar container maintained within the medicine management cabinet, the one or more indicators including a pharmaceutical name, a trade name, a dosage, a method of administration, and adverse reactions of the corresponding actual medicine product; a fourth header tile whose associated information is a fourth header preprinted text, What's this for?, heads each of a fourth row of the periodic daily event matrix of tiles of the one or more periodic daily event matrices of tiles, the fourth row including one or more of What's this for? tiles, each of the What's this for? tiles of the one or more What's this for? tiles is vertically aligned to each of the Medicine/Supplement tiles of the second row, wherein each of the What's this for? tiles includes an area are adapted to receive a preprinted What's this for? label whose associated information is one or more of known medical reasons for administering the actual medicine product preprinted thereon corresponding to the corresponding actual medicine product identified by the exemplar contained therewithin the medicine exemplar container releasably attached to each of the vertically aligned Medicine/Supplement tile of the second row, and corresponding to a second exemplar of the corresponding actual medicine product contained therewithin a corresponding remote medicine exemplar container maintained within the medicine management cabinet; a first periodic daily event matrix of tiles is completely shaded with the first color which is yellow, and bearing the viewable text of the first periodic daily event of the day, which is Breakfast, preprinted thereon an area of the first row of the first periodic daily event matrix of tiles forming a Breakfast matrix of tiles; the second periodic daily event matrix of tiles is completely shaded with the second color which is orange, and bearing the viewable text of the second periodic daily event of the day, which is Lunch, preprinted thereon the area of the first row of the second periodic daily event matrix of tiles forming a Lunch matrix of tiles; the third periodic daily event matrix of tiles is completely shaded with the third color which is green, and bearing the viewable text of the third periodic daily event of the day which is Dinner, preprinted thereon the area of the first row of the third periodic daily event matrix of tiles forming a Dinner matrix of tiles; the fourth periodic daily event matrix of tiles is completely shaded with the fourth color which is blue, and having the viewable text of the fourth periodic daily event of the day which is Bedtime, preprinted thereon the area of the first row of the fourth periodic daily event matrix of tiles forming a Bedtime matrix of tiles; and the fifth periodic daily event matrix of tiles is completely shaded with the fifth color, which is purple, and having the viewable text of the fifth periodic daily event of the day, which is As Needed, preprinted thereon the area of the first row of the fifth periodic daily event matrix of tiles forming an As Needed matrix of tiles; the medicine management cabinet, comprising: a housing defining an open interior region, the housing including an open front, a closed interior back wall, a closed exterior back wall, a top wall, a bottom floor plane, a right side wall, a left side wall, wherein the closed exterior back wall includes a permanently attached adjoining ferromagnetic wall adapted and operable to act as a permanent exterior magnetic board; a divider wall removably inserted within the open interior region positioned vertically within the open interior region forming two vertical open interior portions, a first vertical open interior portion, and a second vertical open interior portion; a door having a front planar surface and a rear planar surface, wherein the rear planar surface includes a ferromagnetic substrate therein adapted and operable for the rear planar surface to act as a magnetic inside door, the door extending from the bottom floor plane to the top wall and from the right side wall to the left side wall, the door being pivotally mounted to the housing and operable for selectively providing access to the open interior region thereof and covering the open front thereof; a locking means adapted and operable for selectively opening and closing the door; one or more mateable mounting storage containers wherein each of the one or more mateable mounting storage containers includes at least one of the mateable mounting magnets of the plurality of mateable mounting magnets adapted and operable for removably attaching and relocating one or more mateable mounting storage containers to the magnetic inside door, or to the exterior permanent magnetic board; one or more mateable mounting hook devices adapted for enabling the display of a hanging medical apparatus, the one or more mateable mounting hook devices having at least one of the mateable mounting magnets of the plurality of mateable mounting magnets attached thereon adapted for removably attaching and relocating the one or more mateable mounting hook devices to the magnetic inside door or to the exterior permanent magnetic board; one or more drawers, wherein each drawer of the one or more drawers is slidably engaged within the medicine management cabinet via a mounting means, wherein each drawer includes an upstanding right side wall, an upstanding left side wall, an upstanding rear wall, a base floor plane, and a raised front wall upstanding from a front surface of the base floor plane, wherein the raised front wall includes a ferromagnetic layer; one or more of the medicine exemplar containers of the plurality of medicine exemplar containers is removably attached onto the raised front wall of each of the drawers of the one or more drawers forming one or more remote medicine exemplar containers to visually identify and correlate the second exemplar contained therewithin with the corresponding actual medicine product contained in a corresponding actual medicine product container stored therewithin the drawer immediately behind the one or more remote medicine exemplar containers; a first drawer of the one or more drawers, wherein a first drawer includes a Breakfast label removably attached to the raised front wall of the first drawer via one of the mateable mounting magnets of the plurality of mateable mounting magnets to form a Breakfast drawer; a second drawer of the one or more drawers, wherein the second drawer includes a Lunch label removably attached to the raised front wall of the second drawer via one of the mateable mounting magnets of the plurality of mateable mounting magnets to form a Lunch drawer; a third drawer of the one or more drawers, wherein the third drawer includes a Dinner label removably attached to the raised front wall of the third drawer via one of the mateable mounting magnets of the plurality of mateable mounting magnets to form a Dinner drawer; a fourth drawer of the one or more drawers, wherein the fourth drawer includes a Bedtime label removably attached to the raised front wall of the fourth drawer via one of the mateable mounting magnets of the plurality of mateable mounting magnets to form a Bedtime drawer; and a fifth drawer of the one or more drawers, wherein the fifth drawer includes an As Needed label removably attached to the raised front wall of the fifth drawer via one of the mateable mounting magnets of the plurality of mateable mounting magnets to form an As Needed drawer; a plurality of transferable malleable dividers, wherein one or more of a transferable malleable dividers of the plurality of transferable malleable dividers is configured to position within one or more drawers and operable for dividing the one or more drawers into two or more sections; an open storage pocket formed by rectangular panel having a recess in a front portion thereof being permanently attached to a rear exterior surface of the top wall of the medicine management cabinet and an exterior bottom floor plane of the bottom floor plane of the medicine management cabinet such that the open storage pocket behind the closed exterior back wall of the medicine management cabinet is formed, an open slot being provided between the top wall and the bottom floor plane for enabling access to the open storage pocket, wherein the open storage pocket is adapted and operable to slidably receive and store the portable rigid magnetic board when having the medicine management chart removably attached thereon; a retractable handle integrally machined within the medicine management cabinet for enabling transport of the medicine management cabinet; at least four swivel wheels attached to the bottom floor plane of the medicine management cabinet for enabling 360 degree swiveling movement of each of the wheels and operable to turn the medicine management cabinet in a 360 degrees clockwise direction or a 360 degrees counter-clockwise direction; the mounting platform, comprising: a support means for enabling the support of the portable rigid magnetic board having the medicine management chart removably attached thereon against sliding downwards due to gravitational force; the actual medicine product daily organizer, comprising: a generally flat housing including a uniform upwardly facing array of color shaded cubicles arranged in columns and rows; wherein the rows of the color shaded cubicles sufficient in number for receiving doses of the actual medicine products at each of the periodic daily events of the day for each of seven days of a week, each of the seven days of the week arranged in columns over a preselected number of days; wherein each of the color shaded cubicles includes an operable lid opening to a cavity, the operable lid adapted and operable for opening upwardly for receiving, containing, and removing of a dose of the actual medicine product as discerned from the Prescription/Supplement label corresponding to the corresponding actual medicine product identified by the exemplar contained therewithin the medicine exemplar container releasably attached to the adjacent Medicine/Supplement tile of the second row of the periodic daily event matrix of tiles; wherein the operable lid is configured over the opening to the cavity and pivotally attached to an upper marginal edge of a rear side of each of the color shaded cubicles; wherein each operable lid has an upwardly releasable locking means for selectively opening and closing the operable lid; wherein each of the operable lids of the color shaded cubicles bearing the color of the periodic daily event of the day and each bearing the viewing text associated with the periodic daily event of the day as discerned from the periodic daily event code-sheet are arrayed in the chronological arrangement depicted on the periodic daily event color-code sheet, and the arrangement of the periodic daily event matrices of tiles within the medicine management chart, and the chronological arrangement of the one or more drawers within the medicine management cabinet, advising of the proper sequence and timing of manually opening each of the operable lids of the color shaded cubicles to receive the dosage of the corresponding actual medicine product, contain the corresponding actual medicine products, and gain access to the dosage of the corresponding actual medicine product for administration to the specific patient; a second viewing text includes each day of the days of a week preprinted thereon; wherein a first row of color shaded cubicles completely shaded in the first color, yellow, including the viewing text bearing the first periodic daily event of the day, Breakfast, preprinted thereon as depicted on the periodic daily event color-code sheet to form a Breakfast row including yellow color shaded cubicles; a second row of color shaded cubicles of the one or more rows of color shaded cubicles is completely shaded in the second color, orange, including the viewable text bearing the second periodic daily event of the day, Lunch, preprinted thereon as depicted on the periodic daily event color-code sheet to form a Lunch row of orange color shaded cubicles; a third row of color shaded cubicles of the one or more rows of color shaded cubicles is completely shaded in the third color, green, including the text bearing the third periodic daily event of the day, Dinner, preprinted thereon as depicted on the periodic daily event color-code sheet to form a Dinner row of green color shaded cubicles; a fourth row of color shaded cubicles of the one or more rows of color shaded cubicles is completely shaded in the fourth color, blue, including the text bearing the fourth periodic daily event of the day, Bedtime, preprinted thereon as depicted on the periodic daily event color-code sheet to form a Bedtime row of blue color shaded cubicles; a fifth row of color shaded cubicles of the one or more rows of color shaded cubicles is completely shaded in the fifth color, purple, including the text of the fifth periodic daily event of the day, As Needed, preprinted thereon as depicted on the periodic daily event color-code sheet to form an As Needed row of purple color shaded cubicles; the mobile communications device, comprising: one or more microprocessors configured to: receive, identify, derive, store, retrieve, data input, via a user interface, the data input including identification of the specific patient, identification of the medical practitioner of the specific patient, caregiver of the specific patient, date, year, one or more medicine management charts, periodic daily event color-code sheet, one or more captured images of the medicine management chart; a mobile cell phone having a preinstalled camera for capturing a plurality of images of the medicine management chart; the medicine management notebook, comprising: a storage device for receiving, storing, and retrieving a copy of the identified captured image of the medicine management chart;

storing the actual medicine products into any one of the Breakfast drawer, the Lunch drawer, the Dinner drawer, the Bedtime drawer, the As Needed drawer, as ascertained from a corresponding Prescription/Supplement label on the medicine management chart;

removably attaching the patient identification card of the specific patient to the area of the patient identification tile of the medicine management chart;

removably attaching the medical practitioner identification card of a medical practitioner of the specific patient to the area of the medical practitioner tile of the medicine management chart;

preprinting a first Prescriptions/Supplements label including identifiers for a first exemplar and removably attaching the first Prescriptions/Supplements label to a first Prescriptions/Supplements tile of any one of the Breakfast matrix of tiles, Lunch matrix of tiles, Dinner matrix of tiles, Bedtime matrix of tiles, As Needed matrix of tiles, as ascertained by the medicine regimen of the specific patient;

preprinting a first What's this for? label including identifiers for the first exemplar and removably attaching the first What's this for? label to a first What's this for? tile of any one of the Breakfast matrix of tiles, the Lunch matrix of tiles, the Dinner matrix of tiles, the Bedtime matrix of tiles, the As Needed matrix of tiles, as ascertained by the medicine regimen of the specific patient;

providing a first exemplar corresponding to each of the actual medicine products;

placing the first exemplar of the corresponding actual medicine product into a first medicine exemplar container of the plurality of medicine exemplar containers;

removably attaching the first medicine exemplar container onto any one of a first Medicine/Supplement tile of the Breakfast matrix of tiles, the Lunch matrix of tiles, the Dinner matrix of tiles; the Bedtime matrix of tiles, the As Needed matrix of tiles, as ascertained from the corresponding first Prescriptions/Supplement label on the medicine management chart;

placing a second exemplar of the corresponding actual medicine product into a second medicine exemplar container of the plurality of exemplar containers forming a first remote medicine exemplar container;

removably attaching the first remote medicine exemplar container onto any one of the raised front walls of the Breakfast drawer, the Lunch drawer, the Dinner drawer, the Bedtime drawer, the As Needed drawer as ascertained by the indicators of the corresponding Prescriptions/Supplements label on the medicine management chart;

storing one or more actual medicine product containers in a corresponding drawer within the medicine management cabinet;

identifying a first actual medicine product by means of the first exemplar contained therewithin the first medicine exemplar container;

identifying the first actual medicine product a second time by means of the second exemplar contained in the first remote medicine exemplar container;

placing a dosage of the first actual medicine product into a first color shaded cubicle of the actual medicine product daily organizer in any one of the Breakfast row of yellow color shaded cubicles, the Lunch row of orange color shaded cubicles, the Dinner row of green color shaded cubicles, the Bedtime row of blue color shaded cubicles, the As Needed row of color shaded cubicles as ascertained by the indicators of the corresponding Prescription/Supplements label of the medicine management chart;

completing the medical management chart for the remainder of the actual medicine products of the medical regimen of the specific patient;

completing filling the dosages into each of the color shaded cubicles of the actual medicine product daily organizer for each of the actual medicine products as ascertained from the Prescription/Supplements labels of the medicine management chart;

filling the one or more mateable mounting storage containers with one or more auxiliary products, activating the mobile communications device;

activating the preinstalled camera for capturing a plurality of images, the images including, images at a time when the medicine management chart is completed, images at a time thereafter any changes made to the medicine management chart, images of the caregiver, images of the specific patient throughout a term of the medicine regimen;

taking the images by implementing the preinstalled camera;

storing the images within one or more microprocessors of the mobile communications device;

retrieving the images;

using the images to maneuver into a printer for printing a copy of the image of the medicine management chart;

storing the images within the medicine management notebook;

storing the images within a memory of the mobile communication device; and storing the images within a removable memory storage device.

\* \* \* \* \*